(12) United States Patent
Yu et al.

(10) Patent No.: US 9,855,338 B2
(45) Date of Patent: Jan. 2, 2018

(54) POLYGLUTAMATE-AMINO ACID CONJUGATES AND METHODS

(71) Applicant: NITTO DENKO CORPORATION, Osaka (JP)

(72) Inventors: Lei Yu, Oceanside, CA (US); Gang Zhao, Oceanside, CA (US); Sang Van, San Diego, CA (US); Sanjib Kumar Das, Oceanside, CA (US); Zhongling Feng, San Diego, CA (US); Xiaoli Fu, Vista, CA (US); Xinghe Wang, San Diego, CA (US); Yi Jin, Carlsbad, CA (US); Fu Chen, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 15/354,547

(22) Filed: Nov. 17, 2016

(65) Prior Publication Data
US 2017/0119889 A1    May 4, 2017

Related U.S. Application Data

(63) Continuation of application No. 11/566,141, filed on Dec. 1, 2006, now abandoned.

(60) Provisional application No. 60/742,291, filed on Dec. 5, 2005, provisional application No. 60/757,917, filed on Jan. 10, 2006, provisional application No. 60/790,735, filed on Apr. 10, 2006.

(51) Int. Cl.
| | | |
|---|---|---|
| A61K 31/00 | (2006.01) |
| A61K 47/42 | (2017.01) |
| A61K 49/00 | (2006.01) |
| A61K 31/337 | (2006.01) |
| A61K 49/14 | (2006.01) |
| A61K 31/704 | (2006.01) |
| A61K 31/4745 | (2006.01) |
| A61K 47/62 | (2017.01) |
| A61K 47/64 | (2017.01) |
| A61K 47/56 | (2017.01) |

(52) U.S. Cl.
CPC ............ *A61K 47/42* (2013.01); *A61K 31/337* (2013.01); *A61K 31/4745* (2013.01); *A61K 31/704* (2013.01); *A61K 49/0041* (2013.01); *A61K 49/0056* (2013.01); *A61K 49/146* (2013.01); *A61K 47/56* (2017.08); *A61K 47/62* (2017.08); *A61K 47/64* (2017.08)

(58) Field of Classification Search
None
See application file for complete search history.

(56) References Cited

U.S. PATENT DOCUMENTS

| | | |
|---|---|---|
| 4,675,381 A | 6/1987 | Bichon et al. |
| 4,738,843 A | 4/1988 | Oguchi et al. |
| 4,745,161 A | 5/1988 | Saudek et al. |
| 4,888,398 A | 12/1989 | Bichon et al. |
| 4,892,733 A | 1/1990 | Bichon et al. |
| 4,925,662 A | 5/1990 | Oguchi et al. |
| 4,976,962 A | 12/1990 | Bichon et al. |
| 5,087,616 A | 2/1992 | Myers et al. |
| 5,219,564 A | 6/1993 | Zalipsky et al. |
| 5,372,807 A | 12/1994 | Poiani et al. |
| 5,384,333 A | 1/1995 | Davis et al. |
| 5,385,738 A | 1/1995 | Yamashira et al. |
| 5,412,072 A | 5/1995 | Sakurai et al. |
| 5,439,686 A | 8/1995 | Desai et al. |
| 5,449,513 A | 9/1995 | Yokoyama et al. |
| 5,449,720 A | 9/1995 | Russell-Jones et al. |
| 5,455,027 A | 10/1995 | Zalipsky et al. |
| 5,470,510 A | 11/1995 | Willey et al. |
| 5,498,421 A | 3/1996 | Grinstaff et al. |
| 5,510,103 A | 4/1996 | Yokoyama et al. |
| 5,548,064 A | 8/1996 | Russell-Jones et al. |
| 5,660,822 A | 8/1997 | Poiani et al. |
| 5,693,751 A | 12/1997 | Sakurai et al. |
| 5,720,950 A | 2/1998 | Poiani et al. |
| 5,738,864 A | 4/1998 | Schacht et al. |
| 5,762,909 A | 6/1998 | Uzgiris |
| 5,770,222 A | 6/1998 | Unger et al. |
| 5,869,466 A | 2/1999 | Russell-Jones et al. |
| 5,871,710 A | 2/1999 | Bogdanov et al. |
| 5,871,747 A | 2/1999 | Gengoux-Sedlik et al. |
| 5,876,698 A | 3/1999 | Schmitt-Willich et al. |
| 5,900,228 A | 5/1999 | Meade et al. |
| 5,929,198 A | 7/1999 | Tang |
| 5,965,118 A | 10/1999 | Duncan et al. |
| 5,977,163 A | 11/1999 | Li et al. |
| 5,980,862 A | 11/1999 | Meade et al. |
| 5,981,564 A | 11/1999 | Pagé et al. |

(Continued)

FOREIGN PATENT DOCUMENTS

| | | |
|---|---|---|
| CN | 14448420 | 10/2003 |
| EP | 0517740 | 12/1992 |

(Continued)

OTHER PUBLICATIONS

Alm, et al., "Effects of topically applied PGF2 alpha and its isopropylester on normal and glaucomatous human eyes," *Prog. Clin. Biol. Res.*, (1989) 312:447-458.

(Continued)

*Primary Examiner* — James Rogers
(74) *Attorney, Agent, or Firm* — Knobbe, Martens, Olson & Bear, LLP

(57) ABSTRACT

Various biodegradable polyglutamate-amino acids comprising recurring units of the general formulae (I) and (II) are prepared. Such polymers are useful for variety of drug, biomolecule and imaging agent delivery applications.

24 Claims, 29 Drawing Sheets

(56) References Cited

U.S. PATENT DOCUMENTS

| | | |
|---|---|---|
| 5,985,916 A | 11/1999 | Duncan et al. |
| 6,004,763 A | 12/1999 | Gengoux et al. |
| 6,030,941 A | 2/2000 | Summerton et al. |
| 6,096,331 A | 8/2000 | Desai et al. |
| 6,136,846 A | 10/2000 | Rubinfeld et al. |
| 6,143,817 A | 11/2000 | Hallam et al. |
| 6,229,009 B1 | 5/2001 | Lambert et al. |
| 6,235,264 B1 | 5/2001 | Uzgiris |
| 6,251,866 B1 | 6/2001 | Prakash et al. |
| 6,262,107 B1 | 7/2001 | Li et al. |
| 6,306,865 B1 | 10/2001 | Pendergast et al. |
| 6,326,021 B1 | 12/2001 | Schwendeman et al. |
| 6,358,919 B1 | 3/2002 | Kanie et al. |
| 6,391,336 B1 | 5/2002 | Royer |
| 6,395,254 B1 | 5/2002 | Sinn et al. |
| 6,441,025 B2 | 8/2002 | Li et al. |
| 6,441,026 B1 | 8/2002 | Bissery |
| 6,497,901 B1 | 12/2002 | Royer |
| 6,506,405 B1 | 1/2003 | Desai et al. |
| 6,515,017 B1 | 2/2003 | Li et al. |
| 6,517,824 B1 | 2/2003 | Kohn et al. |
| 6,521,209 B1 | 2/2003 | Meade et al. |
| 6,528,061 B1 | 3/2003 | Phalipon et al. |
| 6,537,579 B1 | 3/2003 | Desai et al. |
| 6,630,486 B1 | 10/2003 | Royer |
| 6,673,347 B1 | 1/2004 | Offord et al. |
| 6,692,734 B2 | 2/2004 | Stewart et al. |
| 6,693,083 B2 | 2/2004 | Prakash et al. |
| 6,713,045 B1 | 3/2004 | Meade et al. |
| 6,716,452 B1 | 4/2004 | Piccaiello et al. |
| 6,730,699 B2 | 5/2004 | Li et al. |
| 6,749,868 B1 | 6/2004 | Desai et al. |
| 6,753,006 B1 | 6/2004 | Desai et al. |
| 6,762,188 B1 | 7/2004 | Pendergast et al. |
| 6,855,695 B2 | 2/2005 | Lin et al. |
| 6,884,817 B2 | 4/2005 | Li et al. |
| 6,939,538 B2 | 9/2005 | Prescott et al. |
| 6,962,707 B2 | 11/2005 | Schenk |
| 6,995,245 B2 | 2/2006 | Pool |
| 7,060,724 B2 | 6/2006 | Li et al. |
| 7,067,618 B1 | 6/2006 | Kato et al. |
| 7,070,797 B2 | 7/2006 | Pardee et al. |
| 7,153,864 B2 | 12/2006 | Bhatt et al. |
| 7,166,733 B2 | 1/2007 | Nowotnik et al. |
| 7,317,070 B1 | 1/2008 | Ponnusamy |
| 2001/0028876 A1 | 10/2001 | Uzgiris et al. |
| 2001/0028877 A1 | 10/2001 | Uzgiris |
| 2001/0041189 A1 | 11/2001 | Xu |
| 2002/0016285 A1 | 2/2002 | Bhatt et al. |
| 2002/0077279 A1 | 6/2002 | Kumar et al. |
| 2002/0077290 A1 | 6/2002 | Bhatt et al. |
| 2002/0123609 A1 | 9/2002 | Frechet et al. |
| 2002/0183243 A1 | 12/2002 | Bhatt et al. |
| 2002/0187202 A1 | 12/2002 | Goswami et al. |
| 2002/0197261 A1 | 12/2002 | Li et al. |
| 2003/0049253 A1 | 3/2003 | Li et al. |
| 2003/0054977 A1 | 3/2003 | Kumar et al. |
| 2003/0073617 A1 | 4/2003 | Li et al. |
| 2003/0113335 A1 | 6/2003 | Li et al. |
| 2003/0114363 A1 | 6/2003 | Li et al. |
| 2003/0114397 A1 | 6/2003 | Li et al. |
| 2003/0114518 A1 | 6/2003 | Li et al. |
| 2003/0124055 A1 | 7/2003 | Li et al. |
| 2003/0124143 A1 | 7/2003 | Phalipon |
| 2003/0130170 A1 | 7/2003 | Li et al. |
| 2003/0130178 A1 | 7/2003 | Li et al. |
| 2003/0130341 A1 | 7/2003 | Li et al. |
| 2003/0134793 A1 | 7/2003 | Li et al. |
| 2003/0147807 A1 | 8/2003 | Li et al. |
| 2003/0166507 A1 | 9/2003 | Li et al. |
| 2003/0170201 A1 | 9/2003 | Kataoka et al. |
| 2003/0181359 A1 | 9/2003 | Bebbington et al. |
| 2003/0195152 A1 | 10/2003 | Suarato et al. |
| 2003/0211973 A1 | 11/2003 | Bhatt et al. |
| 2003/0216289 A1 | 11/2003 | Bhatt et al. |
| 2003/0224971 A1 | 12/2003 | Kumar et al. |
| 2003/0232968 A1 | 12/2003 | Li et al. |
| 2004/0018960 A1 | 1/2004 | Li et al. |
| 2004/0043030 A1 | 3/2004 | Griffiths et al. |
| 2004/0047835 A1 | 3/2004 | Bianco |
| 2004/0121954 A1 | 6/2004 | Xu |
| 2004/0136911 A1 | 7/2004 | Uzgiris et al. |
| 2004/0151690 A1 | 8/2004 | Nakanishi et al. |
| 2004/0170563 A1 | 9/2004 | Meade |
| 2004/0198638 A1 | 10/2004 | Li et al. |
| 2005/0118718 A1 | 6/2005 | Bae et al. |
| 2005/0152842 A1 | 7/2005 | Li et al. |
| 2005/0187147 A1 | 8/2005 | Newman et al. |
| 2005/0214375 A1 | 9/2005 | Nakanishi et al. |
| 2005/0266067 A1 | 12/2005 | Sengupta et al. |
| 2005/0271585 A1 | 12/2005 | Uzgiris et al. |
| 2005/0276783 A1 | 12/2005 | Giralt Lledo et al. |
| 2006/0013800 A1 | 1/2006 | Le Buanec et al. |
| 2006/0046967 A1 | 3/2006 | Satyam |
| 2006/0067910 A1 | 3/2006 | Kitagawa et al. |
| 2006/0088592 A1 | 4/2006 | Choi et al. |
| 2006/0111273 A1 | 5/2006 | Li et al. |
| 2006/0135404 A1 | 6/2006 | Li et al. |
| 2006/0205674 A2 | 9/2006 | Satyam |
| 2007/0128118 A1 | 6/2007 | Yu et al. |
| 2007/0148125 A1 | 6/2007 | Kataoka et al. |
| 2008/0051603 A1 | 2/2008 | McKennon et al. |
| 2008/0181852 A1 | 7/2008 | Yu et al. |
| 2008/0253969 A1 | 10/2008 | Yu et al. |
| 2008/0279777 A1 | 11/2008 | Van et al. |
| 2008/0279778 A1 | 11/2008 | Van et al. |
| 2008/0279782 A1 | 11/2008 | Van et al. |
| 2009/0226393 A1 | 9/2009 | Wang et al. |
| 2010/0093935 A1 | 4/2010 | Van et al. |
| 2011/0144315 A1 | 6/2011 | Wang et al. |
| 2011/0224148 A1 | 9/2011 | Ahmadian et al. |
| 2012/0052015 A1 | 3/2012 | Yu et al. |

FOREIGN PATENT DOCUMENTS

| | | |
|---|---|---|
| EP | 0693288 | 1/1996 |
| EP | 0526503 | 6/1997 |
| EP | 0832851 | 4/1998 |
| EP | 1031354 | 8/2000 |
| EP | 1279405 | 1/2003 |
| EP | 1514560 | 3/2005 |
| EP | 1580216 | 9/2005 |
| EP | 1695991 | 8/2006 |
| EP | 1 969 031 | 9/2008 |
| EP | 2 077 290 | 7/2009 |
| JP | 5-178986 | 7/1993 |
| JP | 2001288097 | 10/2001 |
| TW | 2008-04461 | 1/2008 |
| WO | WO 97/33552 | 9/1997 |
| WO | WO 99/43311 | 9/1999 |
| WO | WO 99/49901 | 10/1999 |
| WO | WO 00/63409 | 10/2000 |
| WO | WO 00/78791 | 12/2000 |
| WO | WO 01/26693 | 4/2001 |
| WO | WO 01/70275 | 9/2001 |
| WO | WO 02/26241 | 4/2002 |
| WO | WO 02/087497 | 11/2002 |
| WO | WO 02/087498 | 11/2002 |
| WO | WO 03/017923 | 3/2003 |
| WO | WO 03/041642 | 5/2003 |
| WO | WO 03/055935 | 7/2003 |
| WO | WO 2004/039869 | 5/2004 |
| WO | WO 2004/099375 | 11/2004 |
| WO | WO 2005/056641 | 6/2005 |
| WO | WO 2005/079861 | 9/2005 |
| WO | WO 2005/110013 | 11/2005 |
| WO | WO 2005/121181 | 12/2005 |
| WO | WO 2006/041613 | 4/2006 |
| WO | WO 2006/042146 | 4/2006 |
| WO | WO 2006/060797 | 6/2006 |
| WO | WO 2007/067417 | 6/2007 |
| WO | WO 2008/094834 | 8/2008 |
| WO | WO 2008/141107 | 11/2008 |
| WO | WO 2008/141110 | 11/2008 |

(56) References Cited

FOREIGN PATENT DOCUMENTS

| WO | WO 2008/141111 | 11/2008 |
|---|---|---|
| WO | WO 2009/111271 | 9/2009 |
| WO | WO 2009/141823 | 11/2009 |
| WO | WO 2010/029760 | 3/2010 |
| WO | WO 2010/045370 | 4/2010 |
| WO | WO 2011/075483 | 6/2011 |
| WO | WO 2011/113733 | 9/2011 |
| WO | WO 2012/027204 | 3/2012 |

OTHER PUBLICATIONS

Asano, et al., "Fusibility of Poly(n-carboxy α-Amino Acid Anhydride) Materials Treated under Pressure-Heat Conditions and in Vitro-in Vivo Degradation of Hot-Pressed Materials," *J. Macromol. Sci-Chem.*, (1984) A21(5):561-582.
Beverung, et al., "Adsorption dynamics of L-glutamic acid copolymers at a heptane/water interface," *Biophysical Chemistry*, 70(2):121-132 (1998).
Blout, et al., "Polypeptides. III. The Synthesis of High Molecular Weight Poly-(-benzyl-L-glutamates," *J. Am. Chem. Soc.*, (1956) 78(5):941-946 (1956).
Bourke, et al., "Polymers derived from the amino acid L-tyrosine: polycarbonates, polyarylates and copolymers with poly(ethylene glycol)," *Adv. Drug Del. Rev.*, (2003) 55:447-466.
Brannon-Peppas, et al., "Nanoparticle and targeted systems for cancer therapy," *Adv. Drug Del. Rev.*, (2004) 56:1649-1659.
Bulte, et al., "Magnetic resonance microscopy and histology of the CNS," *Trends in Biotechnology*, (2002) 20(8):S24-S28.
Bundgaard, et al., "Design of Prodrugs," *Elsevier Science Publishing Company*, New York, NY, (1985) [Table of Contents Only].
Caravan, et al., "Gadolinium(III) Chelates as MRI Contrast Agents: Structure, Dynamics, and Applications," *Chem. Rev.*, (1999) 99:2293-2352.
Constantinides, et al., "Formulation Development and Antitumor Activity of a Filter-Sterilizable Emulsion of Paclitaxel," *Pharmaceutical Research*, (2000) 17(2):175-182.
Damascelli, et al., "Intraarterial chemotherapy with polyoxyethylated castor oil free paclitaxel, incorporated in albumin nanoparticles (ABI-007): Phase I study of patients with squamous cell carcinoma of the head and neck and anal canal: preliminary evidence of clinical activity," *Cancer*, (2001) 92(10):2592-2602.
Dekie, et al., "Poly-L-glutamic acid derivatives as vectors for gene therapy," *J. Control Release*, (2000) 65(1-2):187-202.
De Winne, et al., "Succinoylated Poly[N-(2-Hydroxyethyl)-L-Glutamine] Derivatives for Drug Delivery," *Journal of Bioactive and Compatible Polymers*, (2004) 19:439-452.
De Winne, et al., "Dendritic Poly-[N-(2-Hydroxyethyl)-L-Glutamine]as Potential Drug Carrier," *Journal of Bioactive and Compatible Polymers*, (2004) 19:367-382.
De Winne, et al., "Synthesis and in vitro evaluation of macromolecular antitumour derivatives based on phenylenediamine mustard," *Eur. J. Pharm Sci.*, (2005) 24(2-3):159-68.
Dubruel, et al., "Poly-L-glutamic Acid Derivatives as Multifunctional Vecotrs for Gene Delivery.Part A. Dynthesis and Physicochemical Evaluation," *Biomacromolecules*, (2003) 4(5):1168-1176.
Dubruel, et al., "Poly-L-glutamic Acid Derivatives as Multifunctional Vecotrs for Gene Delivery.Part B. Biological Evaluation," *Biomacromolecules*, (2003) 4(5):1177-1183.
Duncan, Ruth, "The Dawning era of polymer therapeutics," *Nature Reviews Drug Discovery*, (2003) 2:347-360.
Feng, et al., "Antitumor activity of nexil in preclinical animal tumor models," *Nitto Denko Technical Corporation, Abstract #2319 presented at 99th AACR Annual Meeting conference* Apr. 12-16, 2008 in San Diego, CA.
Fingl, et al., "The Pharmacological Basis of Therapeutics," *Macmillan Publishing Co.*, New York, NY, (1975) [Table of Contents Only].

Greene, et al., "Protective Groups in Organic Synthesis," 3rd Ed., *John Wiley & Sons*, New York, NY, (1999) [Table of Contents Only].
Haag, et al., "Polymer Therapeutics: Concept and Application," *Angew. Chem. Int. Ed.*, (2006) 45: 1198-1215.
He, et al., "Evaluation of membranes of copolypeptide of γ-benzyl L-glutamate and L-glutamic acid for the permeability of anticancer drugs," *Journal of Membrane Science*, (1997) 130(1-2):17-21.
Heller, et al., "Poly(ortho esters): synthesis, characterization, properties and uses," *Adv. Drug Del. Rev.*, (2002) 54:1015-1039.
Helmus, et al., "Surface analysis of a series of copolymers of L-glutamic acid and L-leucine," *Journal of Colloid and Interface Science*, (1982) 89(2):567-570.
Higuchi, et al., "Pro-drugs as Novel Delivery Systems," *A.C.S. Symposium Series, American Chemical Society*, (1975) 14: [Table of Contents Only].
Hoes, et al., "Optimization of macromolecular prodrugs of the antitumor antibiotic adriamycin," *J. of Controlled Release*, (1985) 2:205-213.
Hoste, et al., "New derivatives of polyglutamic acid as drug carrier systems," *J. of Controlled Release*, (2000) 64:53-61.
Huh, et al., "Structure and ion permeability of poly(L-glutamic acid) membranes prepared under a high electric field," *Sen'i Gakkaishi*, 52(3):148-151(1996).
Ibrahim, et al., "Phase I and pharmacokinetic study of ABI-007, a Cremophor-free, protein-stabilized, nanoparticle formulation of paclitaxel," *Clin. Cancer Res.*, (2002) 8:1038-1044.
Joshi, "Microparticulates for ophthalmic drug delivery," *J. Ocul. Pharmacol.*, (1994) 10:29-45.
Kelner, et al., "Tailor-made polymers for local drug delivery: release of macromolecular model drugs from biodegradable hydrogels based on poly(ethylene oxide)," *J.Control Release*, (2005) 101:13-20.
Kumar, et al., "Polyanhydrides: an overview," *Adv. Drug Del. Rev.*, (2002) 54:889-910.
Lauffer, et al., "Preparation and Water Relaxation Properties of Proteins Labeled with Paramagnetic Metal Chelates," *Magn. Reson. Imaging*, (1985) 3:11-16.
Lazar, et al., "Biological effect of basic polyglutamic acid derivatives," *Acta Physiologica Academiae Scientiarum Hungaricae*, (1972) 41(2):113-123.
Lazar, et al., "The experimental production of hemorrhagic lesions in the rat adrenal, liver, and lung by basic polyglutamic acid derivative," *Research in Experimental Medicine*, (1972) 159(1):58-64.
Li, et al., "Complete Regression of Well-established tumors using a novel water-soluble poly(L-glutamic acid)-paclitaxel conjugate," *Cancer Research*, (1998) 58:2404-09.
Li, Chun, "Poly(L-glutamic acid)-anticancer drug conjugates," *Adv. Drug Del. Rev.*, (2002) 54: 695-713.
Line, et al., "Targeting tumor angiogenesis: comparison of peptide and polymer-peptide conjugates," *Journal of Nuclear Medicine*, (2005) 46:1552-1560.
Lonikar, et al., "Block copolymers of polysaccharides and polyamino acid," *Polymer Preprints*, (1990) 31(1):640-641.
Lu, et al., "Poly(L-glutamic acid) Gd(III)-DOTA Conjugate with a Degradable Spacer for Magnetic Resonance Imaging," *Bioconjugate Chem.*, (2003) 14:715-719.
Matsumura, et al., "Phase I clinical trial and pharmacokinetic evaluation of NK911, a micelle-encapsulated doxorubicin," *British Journal of Cancer*, (2004) 91:1775-1781.
Mayer, et al., "Efficacy of a novel hydrogel formulation in human volunteers," *Ophthalmologica*, (1996)210: 101-103.
Mita, et al., "Phase I study of paclitaxel administered weekly for patients with advanced solid malignancies," *Cancer Chemother Pharmacol.*, (2009) 64:287-295.
Mitra, et al., "Polymeric conjugates of mono- and bi-cyclic alphaVbeta3 binding peptides for tumor targeting," *Journal of Controlled Release*, (2006) 114:175-183.
Monks, et al., "Feasibility of a high-flux anticancer drug screen using a diverse panel of cultured human tumor cell lines," *J. Natl. Cancer Inst.*, (1991) 83:757-766.

(56) References Cited

OTHER PUBLICATIONS

Mordenti, "Intraocular pharmacokinetics and safety of a humanized monoclonal antibody in rabbits after intravitreal administration of a solution or a PLGA microsphere formulation," *Toxicol. Sci.*, (1999) 52:101-106.

Nagata, et al., "Copper Ion Complex Formation of a Dicarboxylic Acid-Containing Polypeptied." *Polymer Journal, Society of Polymer Science*, Tokyo, JP, (1994) 26(1):43-48.

Nakanishi, et al., "Development of the polymer micelle carrier system for doxorubicin," *Journal of Controlled Release*, (2001) 74:295-302.

Panyam, et al., "Biodegradable nanoparticles for drug and gene delivery to cells and tissue." *Adv. Drug Deilv. Rev.*, (2003) 55:329-347.

Pechar, et al., "Poly(ethylene glycol) Multiblock Copolymer as a Carrier of Anti-Cancer Drug Doxorubicin," *Bioconjugate Chem.*, (2000) 11(2):131-139.

Pemawansa, et al., "Macromolecular complexes of helical sodium poly (alpha,L-glutamate) (PGNA) with copolymers (block and random) of ethylene oxide (EO) and propylene oxide (PO)," *Polymer Preprints*, (2000) 41(1): 965-966.

Remington, *Remington's Pharmaceutical Sciences*, 18th Ed., Mack Publishing Co., Easton, PA (1990) [Table of Contents Only].

Rigbi, et al., "Inhibition of trypsin by copolymers of glutamic acid and other amino acids," *Biochemistry*, (1964) 3(5):629-636.

Roche, "Bioreversible Carriers in Drug Design: Theory and Application," *Pergamon Press*, (1987) 14-21.

Rowland, et al., "Suppression of tumour growth in mice by a drug antibody conjugate using a novel approach to linkage," *Nature*, (1975) 255:487-488.

Sengupta, et al., "Temporal targeting of tumour cells and neovasculature with a nanoscale delivery system," *Nature*, (2005) 436:568-572.

Shedden, et al., "Efficacy and tolerability of timolol maleate ophthalmic gel-forming solution versus timolol ophthalmic solution in adults with open-angle glaucoma or ocular hypertension: a six-month, double-masked, multicenter study," *Clin. Ther.*, (2001) 23(3):440-450.

Sidman, et al., "Biodegradable, implantable sustained release systems based on glutamic acid copolymers," *Journal of Membrane Science*, (1980) 7(3):277-291.

Sidman, et al., "Controlled release of macromolecules and pharmaceuticals from synthetic polypeptides based on glutamic acid," *Biopolymers*, (1983) 22(1): 547-556.

Sirlin, et al., "Gadolinium-DTPA-Dextran: A Macromolecular MR Blood Pool Contrast Agent," *Academic Radiology*, (2004) 11:1361-1369.

Sparreboom, et al., "Cremophor EL-mediated Alteration of Paclitaxel Distribution in Human Blood: Clinical Pharmacokinetic Implications," *Cancer Research*, (1999) 59:1454-1457.

Srivastava, et al., "Synthetic substituted enzymes: Part III Glutamic acid copolymers with lysozyme-like activity," *Experientia*, (1970) 26(1):11-12.

Tadros, et al., "Z-protected glutamic acid-based biodegradable thermoplastic and thermosetting polyesters: synthesis and characterization," *Journal of Applied Polymer Science*, (1999) 73(6):869-879.

Thunemann, et al., "Maghemite nanoparticles protectively coated with poly(ethylene imine) and Poly (ethylene oxide)-block-poly(glutamic acid)," *American Chemical Society*, (2006) 22(5):2351-2357.

Uhrich, et al., "Polymeric Systems for Controlled Drug Release," *Chem. Rev.*, (1999) 99:3181-3198.

Vega, et al., "Targeting doxorubicin to epidermal growth factor receptors by site specific conjugation of C225 to poly(L-glutamic acid) through a polyethylene glycol spacer," *Pharm. Res.*, (2003) 20: 826-832.

Wang, et al., "Pharmacokinetics and tissue distribution of nexil, a novel macromolecular formulation of paclitaxel, in nu/nu mice bearing nci-460 lung cancer xenografts," *Nitto Denko Technical Corporation Abstract #5738 presented at 99th AACR Annual Meeting conference* Apr. 12-16, 2008 in San Diego, CA.

Wang, et al., "Pharmacokinetics and tissue distribution of a novel macromolecular formulation of paclitaxel in nu/nu mice bearing NCI-460 lung cancer xenografts," *Nitto Denko Technical Corporation Abstract #2917 presented at 100th AACR Annual Meeting conference* Apr. 18-22, 2009 in Denver, CO.

Wani, et al., "Plant antitumor agents. VI. The isolation and structure of taxol, a novel antileukemic and antitumor agent from Taxus brevifolia," *J. Am. Chem. Soc.*, (1971) 93(9):2325-2327.

Weinmann, et al., "Tissue-specific MR contrast agents," *Eur. J. Radiology*, (2003) 46: 33-44.

Wen, et al., "Synthesis and Characterization of Poly(L-glutamic acid) Gadolinium Chelate: A New Biodegradable MRI Contrast Agent," *Bioconjugate Chem.*, (2004) 15:1408-1415.

Williams, et al., "Biometric Diels-Alder Cyclizations for the Construction of the Brevianamide, Paraherquamide, Sclerotiamide and VM55599 Ring Systems," *Journal Am. Chem. Soc.*, (1998) 120(5): 1090-1091.

Ye, et al., "Poly($\gamma$, L-glutamic acid)-cisplatin conjugate effectively inhibits human breast tumor xenografted in nude mice," *Biomaterials*, 27:5958-5965 (2006).

International Search Report and the Written Opinion dated Mar. 19, 2009 for PCT Application No. PCT/US2008/052094 filed Jan. 25, 2008.

International Search Report and the Written Opinion dated Mar. 27, 2009 for PCT Application No. PCT/US2008/059677 filed Apr. 8, 2008.

International Search Report and the Written Opinion dated Mar. 9, 2009 for PCT Application No. PCT/US2008/063114 filed May 8, 2008.

International Search Report and the Written Opinion dated Apr. 23, 2009 for PCT Application No. PCT/US2008/063126 filed May 8, 2008.

International Search Report and the Written Opinion dated Apr. 24, 2009 for PCT Application No. PCT/US2008/063128 filed May 8, 2008.

International Search Report and the Written Opinion dated Jul. 29, 2009 for PCT Application No. PCT/US2009/035335 filed Feb. 26, 2009.

International Search Report and the Written Opinion dated Apr. 29, 2011 for PCT Application No. PCT/US2011/027773 filed Mar. 9, 2011.

Office Action dated May 13, 2011 for U.S. Appl. No. 12/019,612.
Office Action dated Oct. 25, 2011 for U.S. Appl. No. 12/019,612.
Office Action dated Sep. 8, 2011 for European Patent Application No. 08 728 317.2.
Office Action dated Apr. 6, 2011 for Chinese Patent Application No. 200880007747.2.
Office Action dated Oct. 27, 2011 for U.S. Appl. No. 12/117,601, filed May 8, 2008.
Office Action dated Nov. 4, 2011 for European Patent Application No. 08 795 840.1, filed May 8, 2008.
Office Action dated Jun. 1, 2011 for Chinese Patent Application No. 200880015368.8, filed May 8, 2008.
Office Action dated May 6, 2011 for Australian Patent Application No. 2006322254.
Office Action dated May 10, 2012 for Australian Patent Application No. 2006322254.
Office Action dated Mar. 2, 2010 for Chinese Patent Application No. 200680045816.X.
Office Action dated Jan. 30, 2012 for Chinese Patent Application No. 201010565701.

Van, et al., "Synthesis, characterization, and biological evaluation of poly(L-$\gamma$-glutamyl-glutamine)-paclitaxel nanoconjugate," *International Journal of Nanomedicine* 2010:5 825-837.

Cai, et al., "Pharmacokinetics and Disposition of a Localized Lymphatic Polymeric Hyaluronan Conjugate of of Cisplatin in Rodents," *J Pharm Sci.*, (2010) 99(6):2664-2671.

Cisplatin.org, "Cisplatin", online: http:www.cisplatin.org.

Feng, et al., "Preclinical efficacy studies of a novel nanoparticle-based formulation of paclitaxel that out-performs Abraxane," *Cancer Chemother Pharmacol* (2010) 65:923-930.

(56) References Cited

OTHER PUBLICATIONS

Hornback, et al., "Organic Chemistry" (1998): 50.

Nishiyama, et al., "Novel cisplatin-incorporated polymeric micelles can eradicate solid tumors in mice," *Cancer Research*, (2003) 63:8977-8983.

Nishiyama, et al., "Preparation and characterization of size-controlled polymeric micelle containing cis-dichlorodiammineplatinum(II) in the core," *Journal of Controlled Release*, (2001) 74:83-94.

Paraskar, et al., "Rationally engineered polymeric cisplatin nanoparticles for improved antitumor efficacy," *Nanotechnology*, (2011) 22(26):265101 Epub.

Scagliotti, et al., "Phase II Study of Premetrexed with and Without folic acid and vitamin B12 as front-line therapy in malignant pleural meothelioma" *J. Clin. Oncol.* (2003) 21(8): 1556-1561.

Schaefer, "Metal-Based Drugs," *Properties of Paramagnetic Metals in MRI*, (1997) vol. 4, No. 3, 159-171.

Tansey, et al., "Synthesis and characterization of branched poly(L-glutamic acid) as a biodegradable drug carrier", (2004), *J. Controlled Release*, 94: 39-51.

Uchino, et al., "Cisplatin-incorporating polymeric micelles (NC-6004) can reduce nephrotoxicity and neurotoxicity of cisplatin in rats," *British Journal of Cancer*, (2005) 93:678-687.

Yang, et al., "Effect of molecular weight of PGG-paclitaxel conjugates on in vitro and in vivo efficacy," J. Control. Release (2012), doi:10.1016/j.jconrel.2012.04.010.

International Search Report and the Written Opinion dated May 4, 2007 for PCT Application No. PCT/US2006/045915 filed Dec. 1, 2006.

Poly-(γ-L-aspartyl-glutamine)-poly-L-glutamic acid

| Compound | HPLC (time) | LC-MS (time) | Mass-detected by LC-MS |
| --- | --- | --- | --- |
| 2'-PTX-Glu | ~ 32 min | ~6.2 min | 982 |
| 7-PTX-Glu | ~35 min | ~6.4 min | 982 |

The same HPLC column and conditions for both compounds.
The same LC-MS column and conditions for both compounds.

PGA-97-G-27

POLYGLUTAMATE-AMINO ACID CONJUGATES AND METHODS

This application is a continuation of U.S. Ser. No. 11/566,141, filed Dec. 1, 2006, which claims priority to U.S. Provisional Application No. 60/742,291, filed on Dec. 5, 2005; U.S. Provisional Application No. 60/757,917, filed on Jan. 10, 2006; and U.S. Provisional Application No. 60/790,735, filed on Apr. 10, 2006; all of which are incorporated herein by reference in their entireties.

BACKGROUND OF THE INVENTION

Field of the Invention

This invention relates generally to biocompatible water-soluble polymers with pendant functional groups and methods for making them, and particularly to polyglutamate amino acid conjugates useful for a variety of drug, biomolecule and imaging agent delivery applications.

Description of the Related Art

A variety of systems have been used for the delivery of drugs, biomolecules, and imaging agents. For example, such systems include capsules, liposomes, microparticles, nanoparticles, and polymers.

A variety of polyester-based biodegradable systems have been characterized and studied. Polylactic acid (PLA), polyglycolic acid (PGA) and their copolymers polylactic-co-glycolic acid (PLGA) are some of the most well-characterized biomaterials with regard to design and performance for drug-delivery applications. See Uhrich, K. E.; Cannizzaro, S. M.; Langer, R. S. and Shakeshelf, K. M. "Polymeric Systems for Controlled Drug Release." Chem. Rev. 1999, 99, 3181-3198 and Panyam J, Labhasetwar V. "Biodegradable nanoparticles for drug and gene delivery to cells and tissue." Adv Drug Deliv Rev. 2003, 55, 329-47. Also, 2-hydroxypropyl methacrylate (HPMA) has been widely used to create a polymer for drug-delivery applications. Biodegradable systems based on polyorthoesters have also been investigated. See Heller, J.; Barr, J.; Ng, S. Y.; Abdellauoi, K. S. and Gurny, R. "Poly(ortho esters): synthesis, characterization, properties and uses." Adv. Drug Del. Rev. 2002, 54, 1015-1039. Polyanhydride systems have also been investigated. Such polyanhydrides are typically biocompatible and may degrade in vivo into relatively non-toxic compounds that are eliminated from the body as metabolites. See Kumar, N.; Langer, R. S. and Domb, A. J. "Polyanhydrides: an overview." Adv. Drug Del. Rev. 2002, 54, 889-91.

Amino acid-based polymers have also been considered as a potential source of new biomaterials. Poly-amino acids having good biocompatibility have been investigated to deliver low molecular-weight compounds. A relatively small number of polyglutamic acids and copolymers have been identified as candidate materials for drug delivery. See Bourke, S. L. and Kohn, J. "Polymers derived from the amino acid L-tyrosine: polycarbonates, polyarylates and copolymers with poly(ethylene glycol)." Adv. Drug Del. Rev., 2003, 55, 447-466.

Administered hydrophobic anticancer drugs and therapeutic proteins and polypeptides often suffer from poor bio-availability. Such poor bio-availability may be due to incompatibility of bi-phasic solutions of hydrophobic drugs and aqueous solutions and/or rapid removal of these molecules from blood circulation by enzymatic degradation. One technique for increasing the efficacy of administered proteins and other small molecule agents entails conjugating the administered agent with a polymer, such as a polyethylene glycol ("PEG") molecule, that can provide protection from enzymatic degradation in vivo. Such "PEGylation" often improves the circulation time and, hence, bio-availability of an administered agent.

PEG has shortcomings in certain respects, however. For example, because PEG is a linear polymer, the steric protection afforded by PEG is limited, as compared to branched polymers. Another shortcoming of PEG is that it is generally amenable to derivatization at its two terminals. This limits the number of other functional molecules (e.g. those helpful for protein or drug delivery to specific tissues) that can be conjugated to PEG.

Polyglutamic acid (PGA) is another polymer of choice for solubilizing hydrophobic anticancer drugs. Many anti-cancer drugs conjugated to PGA have been reported. See Chun Li. "Poly(L-glutamic acid)-anticancer drug conjugates." Adv. Drug Del. Rev., 2002, 54, 695-713. However, none are currently FDA-approved.

Paclitaxel, extracted from the bark of the Pacific Yew tree (Wani et al. "Plant antitumor agents. VI. The isolation and structure of taxol, a novel antileukemic and antitumor agent from *Taxus brevifolia.*" *J Am Chem Soc.* 1971, 93, 2325-7), is a FDA-approved drug for the treatment of ovarian cancer and breast cancer. However, like other anti-cancer drugs, pacilitaxel suffers from poor bio-availability due to its hydrophobicity and insolubility in aqueous solution. One way to solubilize pacilitaxel is to formulate it in a mixture of Cremophor-EL and dehydrated ethanol (1:1, v/v) (Sparreboom et al. "Cremophor EL-mediated Alteration of Pacitaxel Distribution in Human Blood: Clinical Pharmacokinetic Implications." *Cancer Research* 1999, 59, 1454-1457). This formulation is currently commercialized as Taxol® (Bristol-Myers Squibb). Another method of solubilizing paclitaxel is by emulsification using high-shear homogenization (Constantinides et al. "Formulation Development and Antitumor Activity of a Filter-Sterilizable Emulsion of Paclitaxel." Pharmaceutical Research 2000, 17, 175-182). Recently, polymer-paclitaxel conjugates have been advanced in several clinical trials (Ruth Duncan "The Dawning era of polymer therapeutics." *Nature Reviews Drug Discovery* 2003, 2, 347-360). More recently, paclitaxel has been formulated into nano-particles with human albumin protein and has been used in clinical studies (Damascelli et al. "Intraarterial chemotherapy with polyoxyethylated castor oil free paclitaxel, incorporated in albumin nanoparticles (ABI-007): Phase II study of patients with squamous cell carcinoma of the head and neck and anal canal: preliminary evidence of clinical activity." *Cancer.* 2001, 92, 2592-602, and Ibrahim et al. "Phase I and pharmacokinetic study of ABI-007, a Cremophor-free, protein-stabilized, nanoparticle formulation of paclitaxel." *Clin Cancer Res.* 2002, 8, 1038-44). This formulation is currently commercialized as Abraxane® (American Pharmaceutical Partners, Inc.).

Magnetic resonance imaging (MRI) is an important tool in diagnosis and staging of disease because it is non-invasive and non-irradiating (see Bulte et al. "Magnetic resonance microscopy and histology of the CNS." *Trends in Biotechnology* 2002, 20, S24-S28). Although images of tissues can be obtained, MRI with contrast agents significantly improves its resolution. However, paramagnetic metal ions suitable for MRI contrast agents are often toxic. One of the methods to reduce toxicity is to chelate these metal ions with polydentate molecules such as diethylenetriamine pentaacetate molecules (DTPA). Gd-DTPA was approved by FDA in 1988 for clinical uses, and it is currently commercialized as Magnevist®. Other Gd-chelates were approved by FDA and commercialized, and many others are under development (see Caravan et al. "Gadolinium(III) Chelates as MRI Contrast Agents: Structure, Dynamics, and Applications." *Chem. Rev.* 1999, 99, 2293-2352).

However, Gd-DTPA is not ideal for targeting tumor tissues because it lacks specificity. When Gd-DTPA is administered via IV injection, it spontaneously and rapidly diffuses into extravascular space of the tissues. Thus, large amounts of contrast agents are usually required to produce reasonable contrast images. In addition, it is quickly eliminated via kidney filtration. To avoid the diffusion and the filtration, macromolecular MRI contrast agents have been developed (see Caravan et al. "Gadolinium(III) Chelates as MRI Contrast Agents: Structure, Dynamics, and Applications." *Chem. Rev.* 1999, 99, 2293-2352. These macromolecular-MRI contrast agents include protein-MRI chelates (see Lauffer et al. "Preparation and Water Relaxation Properties of Proteins Labeled with Paramagnetic Metal Chelates." *Magn. Reson. Imaging* 1985, 3, 11-16), polysaccharide-MRI chelates (see Sirlin et al. "Gadolinium-DTPA-Dextran: A Macromolecular MR Blood Pool Contrast Agent." *Acad Radiol.* 2004, 11, 1361-1369), and polymer-MRI chelates (see Lu et al. "Poly(L-glutamic acid) Gd(III)-DOTA Conjugate with a Degradable Spacer for Magnetic Resonance Imaging." *Bioconjugate Chem.* 2003, 14, 715-719, and Wen et al. "Synthesis and Characterization of Poly(L-glutamic acid) Gadolinium Chelate: A New Biodegradable MRI Contrast Agent." *Bioconjugate Chem.* 2004, 15, 1408-1415.

Recently, tissue-specific MRI contrast agents have been developed (see Weinmann et al. "Tissue-specific MR contrast agents." *Eur. J. Radiol.* 2003, 46, 33-44). However, tumor-specific MRI contrast agents have not been reported in clinical applications. Nano-size particles have been reported to target tumor-tissues via an enhanced permeation and retention (EPR) effect (see Brannon-Peppas et al. "Nanoparticle and targeted systems for cancer therapy." *ADDR* 2004, 56, 1649-1659).

SUMMARY OF THE INVENTION

Relatively hydrophobic imaging agents and drugs (such as certain hydrophobic anti-cancer drugs, therapeutic proteins and polypeptides) often suffer from poor bioavailability. It is believed that this problem is due at least in part to the poor solubility of these imaging agents and drugs in aqueous systems. Certain enzymatically degradable drugs also suffer from poor bioavailability because they are degraded relatively rapidly in the circulatory system, resulting in rapid elimination from the body.

The inventors have discovered a series of novel polyglutamate-amino acids that are capable of conjugating to a number of agents, such as imaging agents and/or drugs. In certain embodiments, the polymers and the resulting conjugates preferentially accumulate in certain tissues (e.g., tumor tissues), and thus are useful for delivering drugs (e.g., anticancer drugs) and/or imaging agents to specific parts of the body (e.g., tumors). In certain embodiments, the polymers and the resulting polymer conjugates form nanoparticles that effectively solubilize the imaging agent and/or drug in aqueous systems by dispersing it at a molecular level, thereby increasing functionality and/or bioavailability.

An embodiment provides a polymer conjugate comprising a recurring unit of the formula (I) and a recurring unit of the formula (II) as set forth below, wherein: each n is independently 1 or 2; each $A^1$ is oxygen or $NR^5$; each $A^2$ is oxygen; $R^1$ and $R^2$ are each independently selected from the group consisting of $C_{1-10}$ alkyl, $C_{6-20}$ aryl, ammonium, alkali metal, a polydentate ligand, a polydentate ligand precursor with protected oxygen atoms, and a compound that comprises an agent; wherein the agent is selected from the group consisting of an anticancer drug, a targeting agent, an optical imaging agent, and a magnetic resonance imaging agent; wherein at least one of $R^1$ and $R^2$ is a group that comprises an agent; $R^3$ and $R^4$ are each independently selected from the group consisting of hydrogen, ammonium, and an alkali metal; wherein the polymer conjugate comprises an amount of the agent in the range of about 1 to about 50% (weight/weight) based on the mass ratio of the agent to the polymer conjugate; $R^5$ is hydrogen or $C_{1-4}$ alkyl; and wherein the amount of the agent, the percentage of the recurring unit of the formula (I) and the percentage of the recurring unit of the formula (II) are selected to provide a polymer conjugate solubility that is greater than that of a comparable polyglutamic acid conjugate that comprises substantially the same amount of the agent, the polymer conjugate solubility being greater when a tested polymer conjugate solution, comprising at least 5 mg/mL of the polymer conjugate in 0.9 wt. % aqueous NaCl at about 22° C., has greater optical clarity over a broader pH range than that of a comparable tested polyglutamic acid conjugate solution.

Another embodiment provides a method of making the polymer conjugate described above, comprising dissolving or partially dissolving a polymeric reactant in a solvent to form a dissolved or partially dissolved polymeric reactant; and reacting the dissolved or partially dissolved polymeric reactant with a second reactant, wherein the second reactant comprises at least one selected from the group consisting of the polydentate ligand, the polydentate ligand precursor with protected oxygen atoms and the compound that comprises the agent.

Another embodiment provides a pharmaceutical composition comprising the polymer conjugate described herein, and further comprising at least one selected from a pharmaceutically acceptable excipient, a carrier, and a diluent.

Another embodiment provides a method of treating or ameliorating a disease or condition comprising administering an effective amount of the polymer conjugate described herein to a mammal in need thereof.

Another embodiment provides a method of diagnosing a disease or condition comprising administering an effective amount of the polymer conjugate described herein to a mammal.

These and other embodiments are described in greater detail below.

DETAILED DESCRIPTION OF THE PREFERRED EMBODIMENTS

Figure 1:
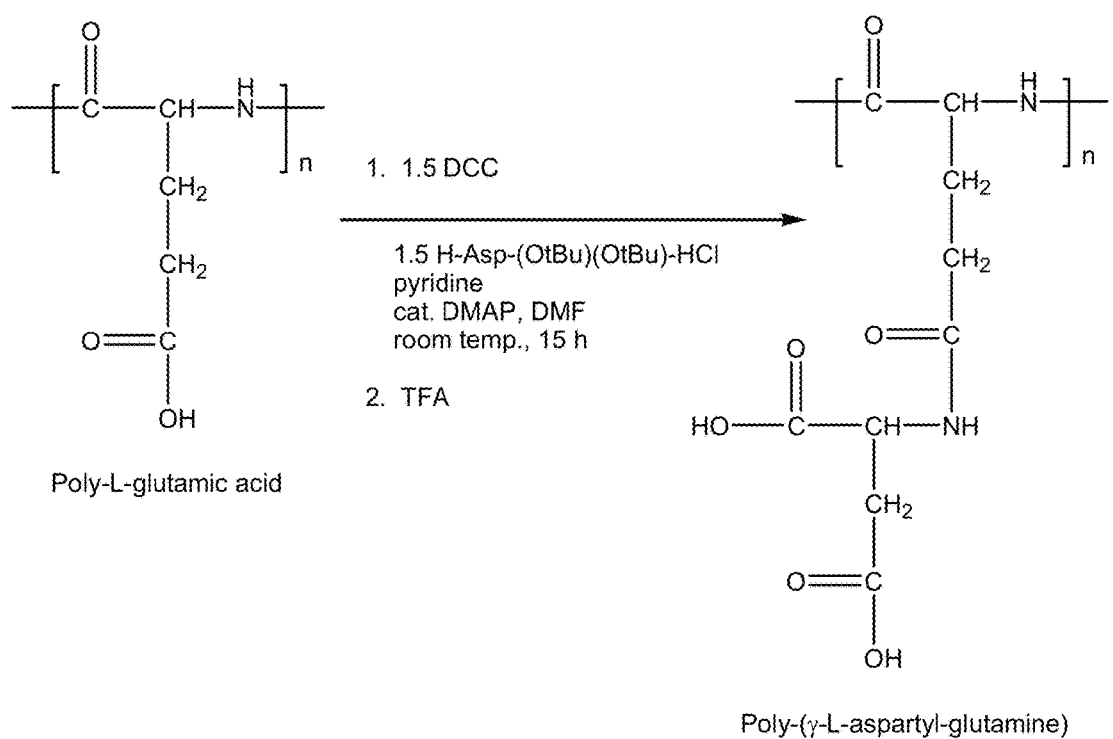
FIG. 1 illustrates a reaction scheme for the preparation of poly-(γ-L-aspartyl glutamine).

The term "ester" is used herein in its ordinary sense, and thus includes a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

The term "amide" is used herein in its ordinary sense, and thus includes a chemical moiety with formula —$(R)_n$—C(O)NHR' or —$(R)_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be included in an amino acid or a peptide molecule attached to drug molecule as described herein, thereby forming a prodrug.

Any amine, hydroxy, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein in its entirety.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Wherever a substituent is described as being "optionally substituted" that substitutent may be substituted with one of the above substituents.

A "paramagnetic metal chelate" is a complex wherein a ligand is bound to a paramagnetic metal ion. Examples include, but are not limited to, 1,4,7,10-Tetraazacyclododecane-1,4,7,10-tetraacetic acid (DOTA)-Gd(III), DOTA-Yttrium-88, DOTA-Indium-111, diethylenetriaminepentaacetic acid (DTPA)-Gd(III), DTPA-yttrium-88, DTPA-Indium-111.

A "polydentate ligand" is a ligand that can bind itself through two or more points of attachment to a metal ion through, for example, coordinate covalent bonds. Examples of polydentate ligands include, but are not limited to, diethylenetriaminepentacetic acid (DTPA), tetraazacyclododecane-1,4,7,10-tetraacetic acid (DOTA), (1,2-ethanediyldinitrilo)tetraacetate (EDTA), ethylenediamine, 2,2'-bipyridine (bipy), 1,10-phenanthroline (phen), 1,2-bis(diphenylphosphino)ethane (DPPE), 2,4-pentanedione (acac), and ethanedioate (ox).

A "polydentate ligand precursor with protected oxygen atoms" is a polydentate ligand comprising oxygen atoms, such as the single-bonded oxygen atoms of carboxyl groups, that are protected with suitable protecting groups. Suitable protecting groups include, but are not limited to, lower alkyls, benzyls, and silyl groups.

An embodiment provides a polymer conjugate comprising a recurring unit of the formula (I) and a recurring unit of the formula (II):

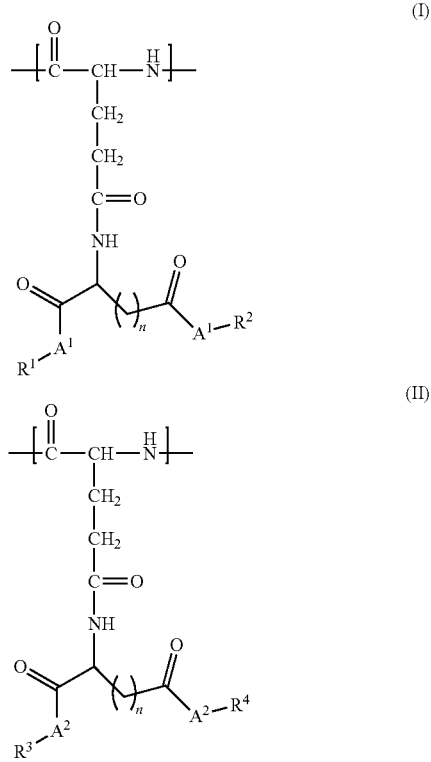

wherein each n is independently 1 or 2, each $A^1$ is oxygen or $NR^5$, each $A^2$ is oxygen, $R^1$ and $R^2$ are each independently selected from the group consisting of optionally substituted $C_{1-10}$ alkyl, optionally substituted $C_{6-20}$ aryl, ammonium, alkali metal, a polydentate ligand, a polydentate ligand precursor with protected oxygen atoms, and a compound that comprises an agent. Examples of alkali metal include lithium (Li), sodium (Na), potassium (K), rubidium (Rb), and cesium (Cs). In an embodiment, the alkali metal is sodium.

The agent may comprise any number of active compounds. For instance, the agent may be selected from the group consisting of an anticancer drug, a targeting agent, an optical imaging agent, and a magnetic resonance imaging agent. At least one of the $R^1$ and $R^2$ groups is a group that comprises the agent. The recurring unit of formula (II) may or may not comprise an agent. In an embodiment, $R^3$ and $R^4$ are each independently selected from the group consisting of hydrogen, ammonium, and an alkali metal. In another embodiment, $R^5$ is either a hydrogen atom or a $C_{1-4}$ alkyl group.

The amount of agent present in the polymer conjugate can vary over a wide range. In an embodiment, the polymer conjugate comprises an amount of the agent in the range of about 1 to about 50% (weight/weight) based on the mass ratio of the agent to the polymer conjugate. In another embodiment, the polymer conjugate comprises an amount of the agent in the range of about 5 to about 40% (weight/weight) based on the mass ratio of the agent to the polymer conjugate. In another embodiment, the polymer conjugate comprises an amount of the agent in the range of about 10 to about 30% (weight/weight) based on the mass ratio of the agent to the polymer conjugate.

It has now been found that the amount of the agent and the percentage amounts of the recurring units of the formula (I) and formula (II) may be selected to advantageously control the solubility of the resulting polymer conjugate. For example, in preferred embodiments, the amount of the agent and the percentage amounts of the recurring units of the formula (I) and formula (II) are selected so that the polymer conjugate is soluble (or insoluble) at a particular pH and/or pH range of interest. In some embodiments, the molecular weight of the polymer is also selected to control solubility. Examples provided below illustrate control over solubility by appropriate selection of the amount of the agent, the percentage amounts of the recurring units of the formula (I) and formula (II), and molecular weight. Those skilled in the art, informed by the guidance provided herein, can use routine experimentation to identify suitable amounts of the agent and percentage amounts of the recurring units of the formula (I) and formula (II) that result in a polymer conjugate with desired solubility characteristics. Such control over solubility may be advantageous, depending on the application. For example, embodiments of the polymer conjugates provided herein may be used to provide improved delivery of otherwise poorly soluble anticancer drugs to selected tissues, preferably reducing undesired side effects, and/or may reduce the frequency at which a subject needs to take the anticancer drug.

The amount of the agent and the percentage amounts of the recurring units of the formula (I) and formula (II) are preferably selected to provide a polymer conjugate solubility that is greater than that of a comparable polyglutamic acid conjugate that comprises substantially the same amount of the same agent. In an embodiment, the polymer conjugate solubility is greater than that of a comparable polyglutamic acid conjugate. Solubility is measured by forming a polymer conjugate solution comprising at least 5 mg/mL of the polymer conjugate in 0.9 wt. % aqueous NaCl at about 22° C., and determining the optical clarity. Optical clarity may be determined turbidimetrically, e.g., by visual observation or by appropriate instrumental methods known to those skilled in the art. Comparison of the resulting solubility to a similarly formed polyglutamic acid conjugate solution shows improved solubility as evidenced by greater optical clarity over a broader range of pH values. Thus, a polymer conjugate solubility is greater than that of a comparable polyglutamic acid conjugate that comprises substantially the same amount of the agent when a tested polymer conjugate solution, comprising at least 5 mg/mL of the polymer conjugate in 0.9 wt. % aqueous NaCl at about 22° C., has greater optical clarity over a broader pH range than that of a comparable tested polyglutamic acid conjugate solution. Those skilled in the art will understand that a "comparable" polyglutamic acid conjugate is a control material in which the polymeric portion of the conjugate has a molecular weight that is approximately the same as that of the subject polymer conjugate (comprising a recurring unit of the formula (I) and a recurring unit of the formula (II)) to which it is being compared.

The polymer conjugate can contain one or more chiral carbon atoms. The chiral carbon (which may be indicated by an asterisk *) can have the rectus (right handed) or the sinister (left handed) configuration, and thus the recurring unit may be racemic, enantiomeric or enantiomerically enriched. The symbols "n" and "*" (designating a chiral carbon), as used elsewhere herein, have the same meaning as specified above, unless otherwise stated.

Polymers comprising a recurring unit of the formula (I) and a recurring unit of the formula (II) are copolymers comprising two or more different recurring units of the formula (I) and the formula (II). Further, polymers comprising a recurring unit of the formula (I) and a recurring unit of the formula (II) may be copolymers that comprise other recurring units that are not of the formula (I) and not of the formula (II). The number of recurring units of the formula (I) and recurring units of formula (II) in the polymer is not limited, but is preferably in the range of from about 50 to about 5,000, and more preferably from about 100 to about 2,000.

A broad variety of other recurring units may be included in the polymer conjugate with the recurring unit of formula (I) and the recurring unit of formula (II). In an embodiment, the polymer conjugate further comprises a recurring unit of the formula (III):

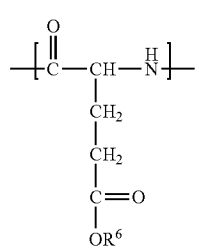

(III)

wherein the $R^6$ group is hydrogen, ammonium, or an alkali metal. When the $R^6$ group is hydrogen, then the recurring unit of the formula (III) is a recurring unit of glutamic acid.

The compound that comprises the agent may be conjugated to the polymer in many different ways. In one embodiment, the compound that comprises the agent can be directly attached to the recurring unit. In another embodiment, the compound that comprises the agent further comprises a linker group. A linker group is a group that attaches the agent (or the compound that comprises the agent) to the polymer. The linker group may be relatively small. For instance, the linker group may comprise an amine, an amide, an ether, an ester, a hydroxyl group, a carbonyl group, or a thiol group. Alternatively, the linker group may be relatively large. For instance, the linker group may comprise an alkyl group, an alkoxy group, an aryl group, an aryl($C_{1-6}$ alkyl) group, a heteroaryl group, or a heteroaryl ($C_{1-6}$ alkyl) group.

The agent may comprise any type of active compound. In an embodiment, the agent may be an optical imaging agent. In a preferred embodiment, the optical imaging agent is one or more selected from the group consisting of an acridine dye, a coumarine dye, a rhodamine dye, a xanthene dye, cyanine dye, and a pyrene dye. For instance, specific optical imaging agents may include Texas Red, Alexa Fluor® dye, BODIPY® dye, Fluorescein, Oregon Green® dye, and Rhodamine Green™ dye, which are commercially available or readily prepared by methods known to those skilled in the art.

In another embodiment, the agent comprises an anticancer drug. In an embodiment, the anticancer drug may be selected from the group consisting of a taxane, camptothecin, and doxorubicin. When the agent comprises a taxane, it is preferable that the taxane is paclitaxel or docetaxel. Paclitaxel may be conjugated to the recurring unit of formula (I) or the recurring unit of formula (II) at the oxygen atom via the C2'-carbon of the paclitaxel. Alternatively or in addition, paclitaxel may be conjugated to the recurring unit of formula (I) or the recurring unit of formula (II) at the oxygen atom via the C7-carbon of the paclitaxel.

In another embodiment, the agent comprises a magnetic resonance imaging agent. In an embodiment, the magnetic resonance imaging agent comprises a paramagnetic metal compound. For example, the magnetic resonance imaging agent may comprise a Gd(III) compound. In such an instance, the Gd(III) compound may be:

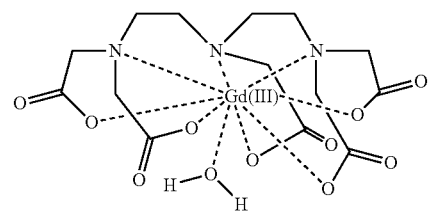

In another embodiment, the agent comprises a polydentate ligand. In an embodiment, the polydentate ligand may be capable of reaction with a paramagnetic metal to form a magnetic resonance imaging agent. For example, the polydentate ligand may comprise several carboxylic acid and/or carboxylate groups. In an embodiment, the polydentate ligand comprises a compound of the following structure:

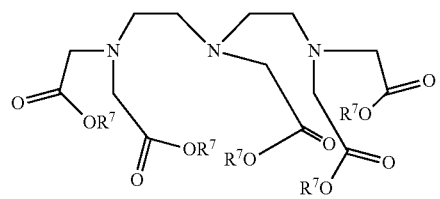

wherein each $R^7$ is independently hydrogen, ammonium, or an alkali metal.

In another embodiment, the agent comprises a polydentate ligand precursor. In such an embodiment, the oxygen atoms of the polydentate ligand are protected by a suitable protecting group. Suitable protecting groups include, but are not limited to, lower alkyls, benzyls, and silyl groups. One example of a polydentate ligand precursor having protecting groups is provided as follows:

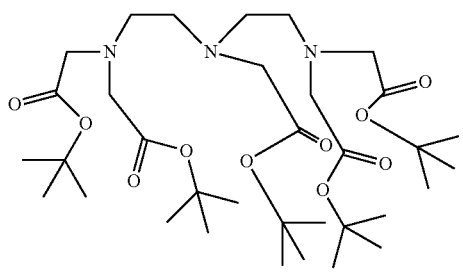 [SMILES: CC(C)(C)OC(=O)CN(CCN(CC(=O)OC(C)(C)C)CC(=O)OC(C)(C)C)CCN(CC(=O)OC(C)(C)C)CC(=O)OC(C)(C)C]

The percentage of recurring units of formula (I) in the polymer conjugate, based on the total number of recurring units, may vary over a wide range. In an embodiment, the polymer may comprise about 1 mole % to about 99 mole % of the recurring unit of formula (I), based on the total moles of recurring units of formulae (I) and (II). In another embodiment, the polymer may comprise about 1 mole % to about 50 mole % of the recurring unit of formula (I) based on the total moles of recurring units of formulae (I) and (II). In another embodiment, the polymer may comprise about 1 mole % to about 30 mole % of the recurring unit of formula (I) based on the total moles of recurring units of formulae (I) and (II). In another embodiment, the polymer may comprise about 1 mole % to about 20 mole % of the recurring unit of formula (I) based on the total moles of recurring units of formulae (I) and (II). In another embodiment, the polymer may comprise about 1 mole % to about 10 mole % of the recurring unit of formula (I) based on the total moles of recurring units of formulae (I) and (II).

In addition to recurring units of the formulae (I) and (II), the polymer conjugate may comprise a variety of other recurring units. For example, in an embodiment, the polymer conjugate comprises recurring units of the formula (III). The percentage of recurring units of formula (I), based on the total number of recurring units in a polymer conjugate comprising recurring units of formulae (I), (II), and (III), may vary over a wide range. In an embodiment, the polymer conjugate may comprise about 1 mole % to about 99 mole % of the recurring unit of formula (I) based on the total moles of recurring units of formulae (I), (II) and (III). In another embodiment, the polymer conjugate may comprise about 1 mole % to about 50 mole % of the recurring unit of formula (I) based on the total moles of recurring units of formulae (I), (II) and (III). In another embodiment, the polymer conjugate may comprise about 1 mole % to about 30 mole % of the recurring unit of formula (I) based on the total moles of recurring units of formulae (I), (II) and (III). In another embodiment, the polymer conjugate may comprise about 1 mole % to about 20 mole % of the recurring unit of formula (I) based on the total moles of recurring units of formulae (I), (II) and (III). In another embodiment, the polymer conjugate may comprise about 1 mole % to about 10 mole % of the recurring unit of formula (I) based on the total moles of recurring units of formulae (I), (II) and (III).

In an embodiment, at least one n in the recurring unit of formula (I) and the recurring unit of formula (II) is 1. In another embodiment, at least one n in the recurring unit of formula (I) and the recurring unit of formula (II) is 2.

In an embodiment, the amount of the agent, the percentage of the recurring unit of the formula (I) and the percentage of the recurring unit of the formula (II) in the polymer conjugate are selected to provide a polymer conjugate solubility that is greater than that of a comparable polyglutamic acid conjugate that comprises substantially the same amount of the agent. The range of pH values over which the polymer conjugate, comprising recurring units of the formula (I) and formula (II), has greater solubility than that of a comparable polyglutamic acid conjugate may be narrow or broad. As noted above, solubility is measured by forming a polymer conjugate solution comprising at least 5 mg/mL of the polymer conjugate in 0.9 wt. % aqueous NaCl at about 22° C., and determining the optical clarity. In an embodiment, the polymer conjugate is soluble over a pH range of at least about three pH units. In another embodiment, the polymer conjugate is soluble over a pH range of at least about 8 pH units. In another embodiment, the polymer conjugate is soluble over a pH range of at least about 9 pH units. In another embodiment, the pH range over which the polymer conjugate is soluble includes at least one pH value in the range of about 2 to about 5, e.g., at pH=2, pH=3, pH=4 and/or pH=5. Preferably, the pH range over which the polymer conjugate is soluble is broader than the pH range over which the comparable polyglutamic acid conjugate is soluble. For example, in an embodiment, the polymer conjugate is soluble over a pH range that is at least about one pH unit broader, preferably at least about two pH units broader, than the pH range over which the comparable polyglutamic acid conjugate is soluble.

The amount of polymer conjugate placed in solution to measure solubility can also vary greatly. In one embodiment, solubility is measured when the tested polymer conjugate solution comprises at least about 5 mg/mL of the polymer conjugate. In another embodiment, solubility is measured when the tested polymer conjugate solution comprises at least about 10 mg/mL of the polymer conjugate. In another embodiment, solubility is measured when the tested polymer conjugate solution comprises at least about 25 mg/mL of the polymer conjugate. In another embodiment, solubility is measured when the tested polymer conjugate solution comprises at least about 100 mg/mL of the polymer conjugate. In another embodiment, solubility is measured when the tested polymer conjugate solution comprises at least about 150 mg/mL of the polymer conjugate. Those skilled in the art will understand that the comparable polyglutamic acid conjugate is tested at about the same concentration as that of the tested polymer conjugate.

Polymers comprising a recurring unit of the formula (I) and a recurring unit of the formula (II) may be prepared in various ways. In an embodiment, a polymeric reactant is dissolved or partially dissolved in a solvent to form a dissolved or partially dissolved polymeric reactant. The dissolved or partially dissolved polymeric reactant is then reacted with a second reactant to form an intermediate product or, in some embodiments, a polymer comprising a recurring unit of the formula (I) and a recurring unit of the formula (II).

The polymeric reactant may comprise any suitable material capable of forming a polymer comprising a recurring unit of the formula (I) and a recurring unit of the formula (II). In an embodiment, the polymeric reactant comprises a recurring unit of the formula (IV):

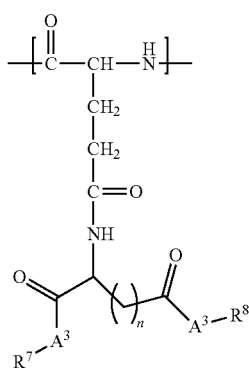

(IV)

wherein each n is independently 1 or 2, each $A^3$ is oxygen, and $R^7$ and $R^8$ are each independently selected from the group consisting of hydrogen, ammonium, and an alkali metal.

In an embodiment, the polymeric reactant may comprise a recurring unit of formula (V):

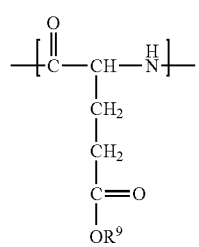

(V)

wherein $R^9$ is hydrogen, ammonium, or an alkali metal.

The second reactant may be a variety of compounds. In an embodiment, the second reactant comprises at least one selected from the group consisting of a polydentate ligand, a polydentate ligand precursor with protected oxygen atoms, and a compound that comprises an agent. In an embodiment, the second reactant may comprise a substituent. The substituent may be selected from the group consisting of hydroxy and an amine.

In an embodiment, the second reactant comprises a compound that comprises an agent. The agent may be any active compound. For instance, the compound that comprises the agent may be selected from the group consisting of an anticancer drug, a targeting agent, an optical imaging agent, and a magnetic resonance imaging agent. In an embodiment, the optical imaging agent may be selected from the group consisting of an acridine dye, a coumarine dye, a rhodamine dye, a xanthene dye, cyanine dye, and a pyrene dye. In another embodiment, the anticancer drug can be selected from the group consisting of a taxane, camptothecin, and doxorubicin. In a preferred embodiment, the anticancer drug may comprise taxane, and the taxane may be selected from the group consisting of paclitaxel and docetaxel.

Paclitaxel may be conjugated to the polymer in a number of ways. In an embodiment, paclitaxel is conjugated to the recurring unit of formula (I) at the oxygen atom attached to the C2'-carbon. In another embodiment, paclitaxel is conjugated to the recurring unit of formula (I) at the oxygen atom attached to the C7-carbon.

In an embodiment, the compound that comprises the agent comprises a magnetic resonance imaging agent. In another embodiment, the magnetic resonance imaging agent comprises a paramagnetic metal compound. Preferably, the compound that comprises the agent comprises a Gd(III) compound. For example, the compound that comprises the agent may comprise the following structure:

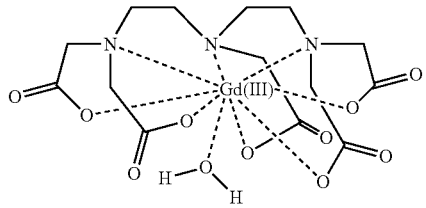

In an embodiment, a polydentate ligand may be conjugated to the polymer. Any suitable polydentate ligand may be used. In an embodiment, the polydentate ligand may be capable of reaction with a paramagnetic metal to form a magnetic resonance imaging agent. For example, the polydentate ligand may comprise several carboxylic acid and/or carboxylate groups. For example, a polydentate ligand of the following structure may be conjugated to the polymer:

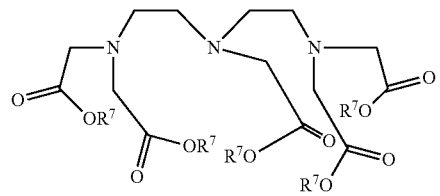

wherein each $R^7$ is independently hydrogen, ammonium, or an alkali metal.

In another embodiment, a polydentate ligand precursor having protecting groups may be conjugated to the polymer. Such a precursor has its oxygen atoms protected by a suitable protecting group(s). Suitable protecting groups include, but are not limited to, lower alkyls, benzyls, and silyl groups. One example of a polydentate ligand precursor having protecting groups is provided as follows:

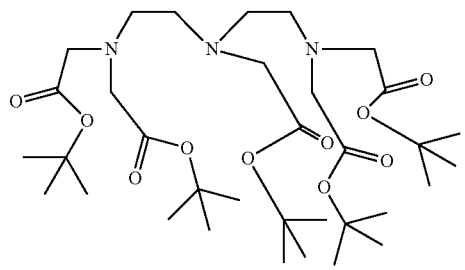 [SMILES: CC(C)(C)OC(=O)CN(CCN(CC(=O)OC(C)(C)C)CC(=O)OC(C)(C)C)CCN(CC(=O)OC(C)(C)C)CC(=O)OC(C)(C)C]

In an embodiment, a method of making the polymer conjugate comprises reacting the dissolved or partially dissolved polymeric reactant with the second reactant in the presence of a coupling agent. Any suitable coupling agent may be used. In an embodiment, the coupling agent is selected from the group consisting of 1-ethyl-3-(3-dimethylaminopropyl)-carbodiimide (EDC), 1,3-dicyclohexyl carbodiimide (DCC), 1,1'-carbonyl-diimidazole (CDI), N,N'-disuccinimidyl carbonate (DSC), N-[(dimethylamino)-1H-1,2,3-triazolo-[4,5-b]pyridine-1-yl-methylene]-N- methylmethanaminium hexafluorophosphate N-oxide (HATU), 2-[(1H-benzotriazol-1-yl)-1,1,3,3-tetramethylaminium hexafluorophosphate (HBTU), 2-[(6-chloro-1H-benzotriazol-1-yl)-1,1,3,3-tetramethylaminium hexafluorophosphate (HCTU), benzotriazole-1-yl-oxy-tris-pyrrolidino-phosphonium hexafluorophosphate (PyBOP®), bromo-tris-pyrrolidino-phosphonium hexafluorophosphate (PyBroP®), 2-[(1H-benzotriazol-1-yl)-1,1,3,3-tetramethylaminium tetrafluoroborate (TBTU), and benzotriazol-1-yl-oxy-tris-(dimethylamino)phosphonium hexafluorophosphate (BOP).

Any suitable solvent that allows the reaction to take place may be used. In an embodiment, the solvent may be a polar aprotic solvent. For instance, the solvent may be selected from the group consisting of N,N-dimethylformamide (DMF), dimethyl sulfoxide (DMSO), N-methyl-2-pyridone (NMP), and N,N-dimethylacetamide (DMAc).

In another embodiment, the reaction may further comprise reacting the dissolved or partially dissolved polymeric reactant in the presence of a catalyst. Any catalyst that promotes the reaction may be used. In an embodiment, the catalyst may comprise 4-dimethylaminopyridine (DMAP).

In an embodiment, a polymer comprising a recurring unit of the formula (I) and a recurring unit of the formula (II) can be produced starting with polyglutamic acid and an amino acid such as asparatic and/or glutamic acid. Alternatively, in another embodiment, the polymer may be created by first converting the starting polyglutamic acid material into its salt form. The salt form of polyglutamic can be obtained by reacting polyglutamic acid with a suitable base, e.g., sodium bicarbonate. An amino acid moiety can be attached to the pendant carboxylic acid group of the polyglumatic acid. The weight average molecular weight of the polyglutamic acid is not limited, but is preferably from about 10,000 to about 500,000 daltons, and more preferably from about 25,000 to about 300,000 daltons. Such a reaction may be used to create poly-(γ-L-aspartyl-glutamine) or poly-(γ-L-glutamyl-glutamine).

In an embodiment, the amino acid is protected by a protecting group before attachment to the polyglutamic acid. One example of a protected amino acid moiety suitable for this reaction is L-aspartic acid di-t-butyl ester hydrochloride, shown below:

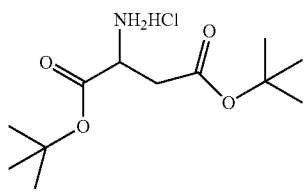

L-aspartic acid di-t-butyl ester hydrochloride

Reaction of the polyglutamic acid with the amino acid may take place in the presence of any suitable solvent. In an embodiment, the solvent can be an aprotic solvent. In a preferred embodiment, the solvent is N,N'-dimethylformamide.

In an embodiment, a coupling agent such as EDC, DCC, CDI, DSC, HATU, HBTU, HCTU, PyBOP®, PyBroP®, TBTU, and BOP can be used. In other embodiments, polyglutamic acid and an amino acid can be reacted using a catalyst (e.g., DMAP).

After completion of the reaction, if the oxygen atoms of the amino acid are protected, the protecting groups can be removed using known methods such as using a suitable acid (e.g., trifluoroacetic acid). If desired, the salt form of the polymer obtained from reacting polyglutamic acid with the amino acid can be formed by treating the acid form of the polymer with a suitable base solution, e.g., sodium bicarbonate solution.

The polymer may be recovered and/or purified by methods known to those skilled in the art. For example, the solvent may be removed by suitable methods, for instance, rotary evaporation. Additionally, the reaction mixture may be filtered into an acidic water solution to induce precipitation. The resultant precipitate can then be filtered, and washed with water.

In an embodiment, a polymer comprising a recurring unit of the formula (I) and a recurring unit of the formula (II) can also include a recurring unit of formula (III) as set forth above. One method for forming a polymer comprising recurring units of the formulae (I), (II), and (III) is by starting with polyglutamic acid and reacting it with an amino acid such as asparatic and/or glutamic acid, in an amount that is less than 1.0 equivalents of the amino acid based on polyglutamic acid. For example, in one embodiment, 0.7 equivalents of an amino acid based on the polyglutamic acid can be reacted with polyglutamic acid, so that about 70% of the recurring units of the resulting polymer comprise the amino acid. As discussed above, the oxygen atoms of the amino acid can be protected using a suitable protecting group. In an embodiment, the amino acid may be L-aspartic acid or L-glutamic acid. In another embodiment, the oxygen atoms of the amino acid can be protected with t-butyl groups. If the oxygen atoms of the amino acid are protected, the protecting groups can be removed using known methods such as a suitable acid (e.g., trifluoroacetic acid).

Conjugation of a group comprising an agent, a polydentate ligand, and/or a polydentate ligand precursor with protected oxygen atoms to the polymer acid or its salt form may be carried out in various ways, e.g., by covalently bonding the group comprising an agent, a polydentate ligand, and/or a polydentate ligand precursor with protected oxygen atoms to various polymers. One method for conjugating the aforementioned groups to the polymer obtained from polyglutamic acid and/or salt is by using heat (e.g, heat from using a microwave method). Alternatively, conjugation may take place at room temperature. Appropriate solvents, coupling agents, catalysts, and/or buffers as generally known to those skilled in the art and/or as described herein may be used to form the polymer conjugate. As with polyglutamic acid, both the salt or acid form of the polymer obtained from polyglutamic acid and/or salt and an amino acid can be used as starting material for forming the polymer conjugate.

Suitable agents that can be conjugated to the polymer obtained from polyglutamic acid and/or salt and an amino acid include but are not limited to optical agents, anticancer drugs, targeting agents, magnetic resonance imaging agents (e.g, paramagnetic metal compounds), polydentate ligands, and polydentate ligand precursors with protected oxygen atoms.

In one embodiment, the polymer obtained from polyglutamic acid and/or salt and an amino acid can be conjugated to an optical agent. In an embodiment, the optical agent can be Texas Red-$NH_2$.

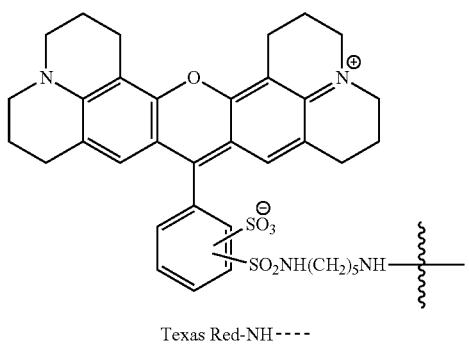

Texas Red-NH----

In one particular embodiment, a polymer comprising at least one recurring unit of the formula (I) and at least one recurring unit of the formula (II) may be reacted with DCC, Texas Red-$NH_2$ dye, pyridine, and 4-dimethylaminopyridine. The mixture is heated using a microwave method. In an embodiment, the reaction is heated up to a temperature in the range of about 100°-150° C. In another embodiment, the time the materials are heated ranges from 5 to 40 minutes. If desired, the reaction mixture can be cooled to room temperature. Suitable methods known to those skilled in the art can be used to isolate and/or purify the polymer conjugate. For instance, reaction mixture can be filtered into an acidic water solution. Any precipitate that forms can then be filtered and washed with water. Optionally, the precipitate can be purified by any suitable method. For example, the precipitate can be transferred into acetone and dissolved, and the resulting solution can be filtered again into a sodium bicarbonate solution. If desired, the resulting reaction solution can be dialyzed in water using a cellulose membrane and the polymer can be lyophilized and isolated.

Conjugates comprising the Texas Red dye may be used to deliver an imaging agent to a selected tissue, as exemplified in the examples below. The polymers described above may be formed into nanoparticles in aqueous solution, e.g., as exemplified below.

In one embodiment, the polymer obtained from polyglutamic acid and/or salt and an amino acid can be conjugated to an anticancer drug. In an embodiment, the anticancer drug can be a taxane, camptothecin, and/or doxorubicin. In a preferred embodiment, the anticancer drug is a taxane such as paclitaxel or docetaxel.

In an embodiment, the antitumor drug conjugated to the polymer is paclitaxel. In an embodiment, paclitaxel may be joined to the polymer at the C2'-oxygen atom. In another embodiment, the paclitaxel may be joined to the polymer at the C7-oxygen atom. In another embodiment, the polymer chain comprises paclitaxel that is coupled to the polymer only by the C2'-oxygen atom. In still another embodiment, the polymer chain comprises paclitaxel that is coupled to the polymer only by the C7-oxygen atom. In yet another embodiment, the polymer comprises both C2'-conjugated paclitaxel groups and C7-conjugated paclitaxel groups.

The anti-cancer drug can be conjugated to the polymer obtained from polyglutamic acid and/or salt and an amino acid using the methods described above with respect to Texas-Red.

In an embodiment, paclitaxel, preferably in the presence of a coupling agent (e.g, EDC and/or DCC) and a catalyst (e.g, DMAP), can be reacted with the polymer obtained from polyglutamic acid and/or salt and an amino acid in a solvent (e.g, an aprotic solvent such as DMF). Additional agents, such as pyridine or hydroxybenzotriazole may be used. In one embodiment, the reaction may take place over the period of 0.5-2 days. Suitable methods known to those skilled in the art can be used to isolate and/or purify the polymer conjugate. For example, the reaction mixture can be poured into an acidic solution to form a precipitate. Any precipitate that forms can then be filtered and washed with water. Optionally, the precipitate can be purified by any suitable method. For example, the precipitate can be transferred into acetone and dissolved, and the resulting solution can be filtered again into a sodium bicarbonate solution. If desired, the resulting reaction solution can be dialyzed in water using a cellulose membrane and the polymer can be lyophilized and isolated. The content of paclitaxel in the resulting polymer may be determined by UV spectrometry.

Alternatively, the compound comprising the agent can be reacted with an amino acid such as glutamic and/or aspartic acid in which the compound comprising the agent is coupled (e.g., covalently bonded) to the amino acid. The amino acid-agent compound can then be reacted with polyglutamic acid or its salt to form the polymer conjugate. In one embodiment, paclitaxel is reacted with glutamic acid to form a compound in which the paclitaxel is covalently bonded to the pendant carboxylic acid group of the glumatic acid. The glutamic acid-paclitaxel compound can then be reacted with polyglutamic acid or its salt to form the polymer conjugate. In one embodiment, paclitaxel is reacted with aspartic acid to form a compound in which the paclitaxel is covalently bonded to the pendant carboxylic acid group of the aspartic acid. The aspartic acid-paclitaxel compound can then be reacted with polyglutamic acid or its salt to form the polymer conjugate. If desired, the paclitaxel coupled to the amino acid by the C2'-oxygen can be separated from the paclitaxel coupled to the amino acid by the C7-oxygen using known separation methods (e.g, HPLC).

After formation of the polymer conjugate, any free amount of agent not covalently bonded to the polymer may also be measured. For example, thin layer chromatography (TLC) may be used to confirm the substantial absence of free paclitaxel remaining in the compositions of polymers conjugated to paclitaxel.

In one embodiment, the polymer obtained from polyglutamic acid and/or salt and an amino acid can be conjugated to a polydentate ligand. Suitable polydentate ligands include but are not limited to diethylenetriaminepentacetic acid (DTPA), tetraazacyclododecane-1,4,7,10-tetraacetic acid (DOTA), (1,2-ethanediyldinitrilo)tetraacetate (EDTA), ethylenediamine, 2,2'-bipyridine (bipy), 1,10-phenanthroline (phen), 1,2-bis(diphenylphosphino)ethane (DPPE), 2,4-pentanedione (acac), and ethanedioate (ox). Appropriate solvents, coupling agents, catalysts, and/or buffers as generally known to those skilled in the art and/or described herein may be used to form the polymer conjugate. In another embodiment, the polymer obtained from polyglutamic acid and/or salt and an amino acid can be conjugated to a polydentate ligand precursor with protected oxygen atoms. As with polyglutamic acid, both the salt or acid form of the polymer obtained from polyglutamic acid and/or salt and an amino acid can be used as starting material for forming the polymer conjugate.

In an embodiment, the polydentate ligand comprises DTPA. In one embodiment, the polydentate ligand such as DTPA (with or with protected oxygen atoms), preferably in the presence of a coupling agent (e.g, DCC) and a catalyst (e.g, DMAP), can be reacted with the polymer obtained from polyglutamic acid and/or salt and an amino acid in a solvent (e.g, an aprotic solvent such as DMF). If protecting groups are present, removal can achieved using suitable methods. For example, the polymer conjugate with the polydentate ligand precursor with protected oxygen atoms such as DTPA with oxygen atoms protected by t-butyl groups can be treated with acid such as trifluoroacetic acid. After removal of the protecting groups, the acid can be removed by rotary evaporation. In one embodiment, DTPA can be treated with a suitable base to remove the hydrogen atoms on the carboxylic acid —OH groups. In some embodiments, the base is sodium bicarbonate.

In one embodiment, the polymer obtained from polyglutamic acid and/or salt and an amino acid can be conjugated to a magnetic resonance imaging agent. In an embodiment, the magnetic resonance imaging agent comprises a Gd(III) compound. One method for forming the magnetic resonance imaging agent is by reacting a paramagnetic metal with the polymer conjugate comprising a polydentate ligand. Suitable paramagnetic metals include but are not limited to Gd(III), Indium-111, and Yttrium-88. For example, a polymer conjugate comprising DTPA can be treated with Gd(III) in a buffer solution for a period of several hours. Suitable methods known to those skilled in the art can be used to isolate and/or purify the polymer conjugate. For instance, the resulting reaction solution can be dialyzed in water using a cellulose membrane and the polymer can be lyophilized and isolated. The amount of paramagnetic metal may be quantified by inductively coupled plasma-optical emission spectroscopy (ICP-OES) measurement.

The polymer conjugates may be used to deliver an imaging agent and/or a drug to a selected tissue, e.g., as exemplified in the examples below. The polymers described above may be formed into nanoparticles in aqueous solution, e.g., as exemplified below. Conjugates comprising a polymer and a drug may be formed into nanoparticles in a similar manner. Such nanoparticles may be used to preferentially deliver a drug to a selected tissue.

Pharmaceutical Compositions

In some embodiments, prodrugs, metabolites, stereoisomers, hydrates, solvates, polymorphs, and pharmaceutically acceptable salts of the compounds disclosed herein (e.g., the polymer conjugate and/or the agent that it comprises) are provided.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds disclosed herein (e.g., the polymer conjugate and/or the agent that it comprises) can be used alone, in combination with other compounds disclosed herein, or in combination with one or more other agents active in the therapeutic areas described herein.

In another aspect, the present disclosure relates to a pharmaceutical composition comprising one or more physiologically acceptable surface active agents, carriers, diluents, excipients, smoothing agents, suspension agents, film forming substances, and coating assistants, or a combination thereof; and a compound (e.g., the polymer conjugate and/or the agent that it comprises) disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetatemethacrylate copolymer as a derivative of polyvinyl may be used as suspension agents; and plasticizers such as ester phthalates and the like may be used as suspension agents.

The term "pharmaceutical composition" refers to a mixture of a compound disclosed herein (e.g., the polymer conjugate and/or the agent that it comprises) with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" refers to chemical compounds diluted in water that will dissolve the compound of interest (e.g., the polymer conjugate and/or the agent that it comprises) as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. The term "physiologically acceptable" refers to a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds (e.g., the polymer conjugate and/or the agent that it comprises) can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few hours or weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the active compound into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein (e.g., the polymer conjugate and/or the agent that it comprises) can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

The following examples are provided for the purposes of further describing the embodiments described herein, and do not limit the scope of the invention.

Materials:

Poly-L-glutamate sodium salts with different molecular weights (average molecular weights of 41,400 (PGA(97k)), 17,600 (PGA(44k)), 16,000 (PGA(32k)), and 10,900 (PGA (21k)) daltons based on multi-angle light scattering (MALS)); 1,3-dicyclohexyl carbodiimide (DCC); N-(3-dimethylaminopropyl)-N'-ethylcarbodiimide hydrochloride (EDC); hydroxybenzotriazole (HOBt); pyridine; 4-dimethylaminopyridine (DMAP); N,N'-dimethylformamide (DMF); gadolinium-acetate; chloroform; and sodium bicarbonate were purchased from Sigma-Aldrich Chemical company. Poly-L-glutamate was converted into poly-L-glutamic acid using 2 N hydrochloric acid solution. Trifluoroacetic acid (TFA) was purchased from Bioscience. Omniscan™ (gadodiamide) was purchased from GE healthcare.

L-Aspartic acid β-t-butyl α-t-butyl ester hydrochloride (H-Asp(OtBu)-OtBu.HCl), L-glutamic acid di-t-butyl ester hydrochloride (H-Glu(OtBu)-OtBu.HCl), N-α-CBZ-L-glutamic acid α-benzyl ester (Z-Glu-OBzl) were purchased from Novabiochem (La Jolla, Calif.). Paclitaxel was purchased from PolyMed (Houston, Tex.). $^3$H-paclitaxel was purchased from Moravek Biochemicals, Inc. Sulforhodamine B dye for cytotoxic MTT test (cell viability) was purchased from Molecular Imaging Products Company (Michigan). The chemical p-NH$_2$-Bn-DPTA-penta (tBu ester) was purchased from Macrocyclics (Dallas, Tex.). Texas Red® cadaverine (Texas Red-NH$_2$ dye) was purchased from Molecular Probe. Bovine serum was purchased from Sigma. It was centrifuged at 10,000 rpm to remove any particulate matter.

$^1$H NMR was obtained from Joel (400 MHz), and particle sizes were measured by ZetaIPals (Brookhaven Instruments Corporation). Microwave chemistry was carried out in Biotage. Molecular weights of polymers were determined by size exclusion chromatography (SEC) combined with a multi-angle light scattering (MALS) (Wyatt Corporation) detector:

SEC-MALS Analysis Conditions:

| | |
|---|---|
| HPLC system: | Agilent 1200 |
| Column: | Shodex SB 806M HQ (exclusion limit for Pullulan is 20,000,000, particle size: 13 micron, size (mm) ID × Length; 8.0 × 300) |
| Mobile Phase: | 1 × DPBS or 1% LiBr in DPBS (pH 7.0) |
| Flow Rate: | 1 ml/min |
| MALS detector: | DAWN HELEOS from Wyatt |
| DRI detector: | Optilab rEX from Wyatt |
| On-line Viscometer: | ViscoStar from Wyatt |
| Software: | ASTRA 5.1.9 from Wyatt |
| Sample Concentration: | 1-2 mg/ml |
| Injection volume: | 100 μl | dn/dc value of polymer: 0.185 was used in the measurement.
BSA was used as a control before actual samples are run.

Using the system and conditions described above (hereinafter, referred to as the Heleos system with MALS detector), the average molecular weight of the starting polymers (poly-L-glutamate sodium salts average molecular weights of 41,400, 17,600, 16,000, and 10,900 daltons reported by Sigma-Aldrich using their system with MALS) were experimentally found to be 49,000, 19,800, 19,450, and 9,400 daltons, respectively.

The content of paclitaxel in polymer-paclitaxel conjugates was estimated by UV/Vis spectrometry (Lambda Bio 40, PerkinElmer) based on a standard curve generated with known concentrations of paclitaxel in methanol ($\lambda$=228 nm).

Synthesis of poly-L-glutamate-paclitaxel conjugates (PGA-PTX) was carried out as reported in previous literature. See Li et al. "Complete Regression of Well-established tumors using a novel water-soluble poly(L-glutamic acid)-paclitaxel conjugate." *Cancer Research* 1998, 58, 2404-2409, the contents of which are herein incorporated by reference in its entirety. The amount of paclitaxel in PGA (97k)-PTX-20 and PGA(32k)-PTX-20, prepared from polyglutamic acid with average molecular weights of 49,000 and 19,450 daltons, respectively, was quantified by UV spectrometry at $\lambda$=229 nm as 20% by weight to weight. By lowering the amount of paclitaxel, 10% by weight to based on total weight was obtained for PGA(97k)-PTX-10 from polyglutamic acid with average molecular weights of 49,000 daltons.

Example 1

A poly-($\gamma$-L-aspartyl-glutamine) was prepared according to the general scheme illustrated in FIG. 1 as follows:

Polyglutamic acid (0.75 g), average molecular weight of 49,000 daltons based on the Heleos system with MALS detector, was partially added into 100 mL dichloromethane (DCM). DCC (8.7 mL, 1 M in DCM) was added and stirred for 20 minutes. DCM was then removed by rotary evaporation, and the residue was dissolved with DMF (80 mL). H-asp(OtBu)-(OtBu) (2.44 g), pyridine (4 mL), and DMAP (0.1 g) were added and the reaction mixture was stirred at room temperature for 15-24 hours. The reaction mixture was filtered into an acidic water solution (500 mL, pH <2 based on pH paper). A white precipitate formed, and was filtered and washed with water. The white precipitate was then dissolved in acetone (100 mL). The solution was filtered through a 0.2-μm filter, and the acetone was removed by rotary evaporation. The structure of the intermediate polymer was confirmed via $^1$H-NMR by the presence of the peak for the O-tBu group at 1.4 ppm.

The intermediate polymer was treated with 95% trifluoroacetic acid (TFA) in DCM for 5-8 hours. DCM was then added until a precipitate formed. The solvent was removed, and the residue was washed with more DCM. The residue was placed under vacuum to remove the DCM. The residue was re-dissolved in methanol and water and then dialyzed using semi-membrane cellulose (molecular weight cut-off 10,000 daltons) in reverse-osmosis water (4 time water changes) overnight. Poly-($\gamma$-L-aspartyl-glutamine) was substantially optically transparent at pH 7 in water after dialysis. Poly-($\gamma$-L-aspartyl-glutamine) (1.2 g) was obtained as white powder after being lyophilized. The polymer was confirmed via $^1$H-NMR by the disappearance of a peak for the O-tBu group at 1.4 ppm.

Example 2

Figure 2:
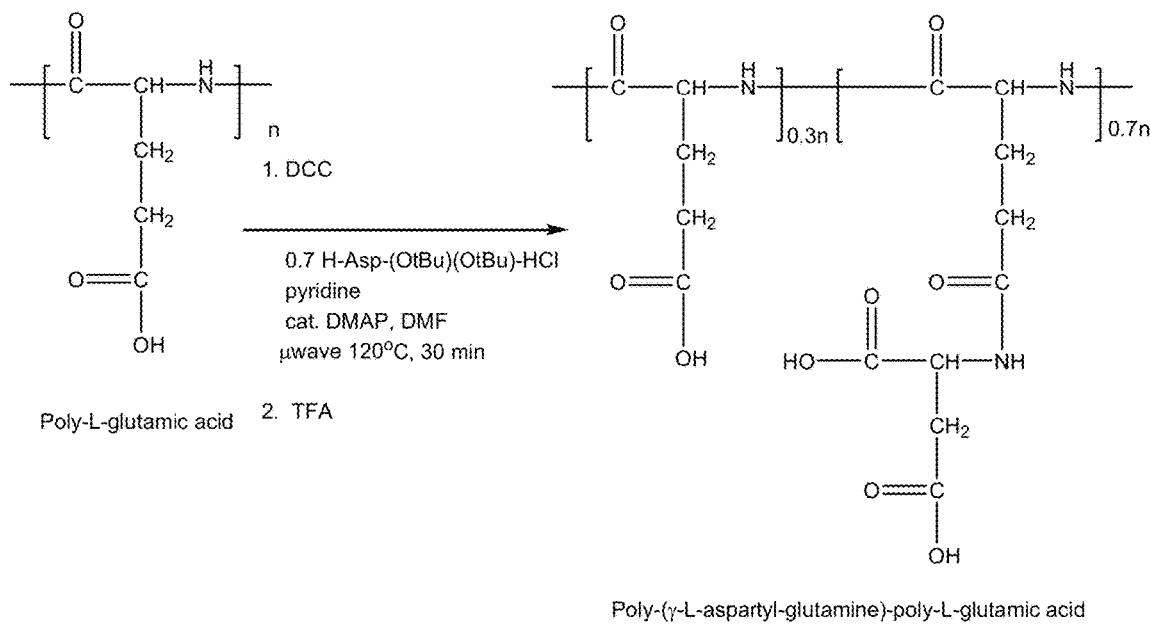
FIG. 2 illustrates a reaction scheme for the preparation of poly-(γ-L-aspartyl glutamine)-poly-L-glutamic acid.

A poly-($\gamma$-L-aspartyl-glutamine)-poly-L-glutamic acid was prepared according to the general scheme illustrated in FIG. 2 as follows:

Polyglutamic acid with an average molecular weight of 49,000 daltons based on the Heleos system with MALS detector (0.075 g) was partially dissolved in DMF (3 mL). DCC (130 mg), H-asp(OtBu)-(OtBu) (0.11 g), pyridine (200 μL), and DMAP (0.010 g) were then added. The reaction was carried out using a microwave method at 120° C. for 30 minutes. The reaction was then cooled to room temperature. Completion of reaction was followed by monitoring the complete disappearance of H-asp(OtBu)-(OtBu) using thin-layer-column (TLC, $R_f$ in ethylacetate=0.4). Upon completion, the reaction mixture was filtered into an acidic water solution (150 mL, pH <2 based on pH paper). A white precipitate formed, and was filtered and washed with water. The white precipitate was then dissolved in acetone (50 mL). The solution was filtered into a sodium bicarbonate solution (0.5 M) and dialyzed using semi-membrane cellulose (molecular weight cut-off 10,000 daltons) in reverse-osmosis water (4 time water changes) overnight. The intermediate polymer ester obtained was white after being lyophilized. The polymer structure was confirmed via $^1$H-NMR by the presence of a peak for the O-tBu group at 1.4 ppm.

The intermediate polymer was then treated with 95% trifluoroacetic acid (TFA) in DCM for 5 hours. DCM was added until a precipitate formed. The solvent was then removed, and the residue was washed with additional DCM. The residue was placed under vacuum to remove the DCM. The residue was then re-dissolved in methanol and water and dialyzed using semi-membrane cellulose (molecular weight cut-off 10,000 daltons) in reverse-osmosis water (4 time water changes) overnight. Poly-($\gamma$-L-aspartyl-glutamine)-poly-L-glutamic acid (0.10 g) was obtained as white powder after being lyophilized. The polymer structure was confirmed via $^1$H-NMR by the disappearance of the peak for the O-tBu group at 1.4 ppm.

Example 3

Figure 3:
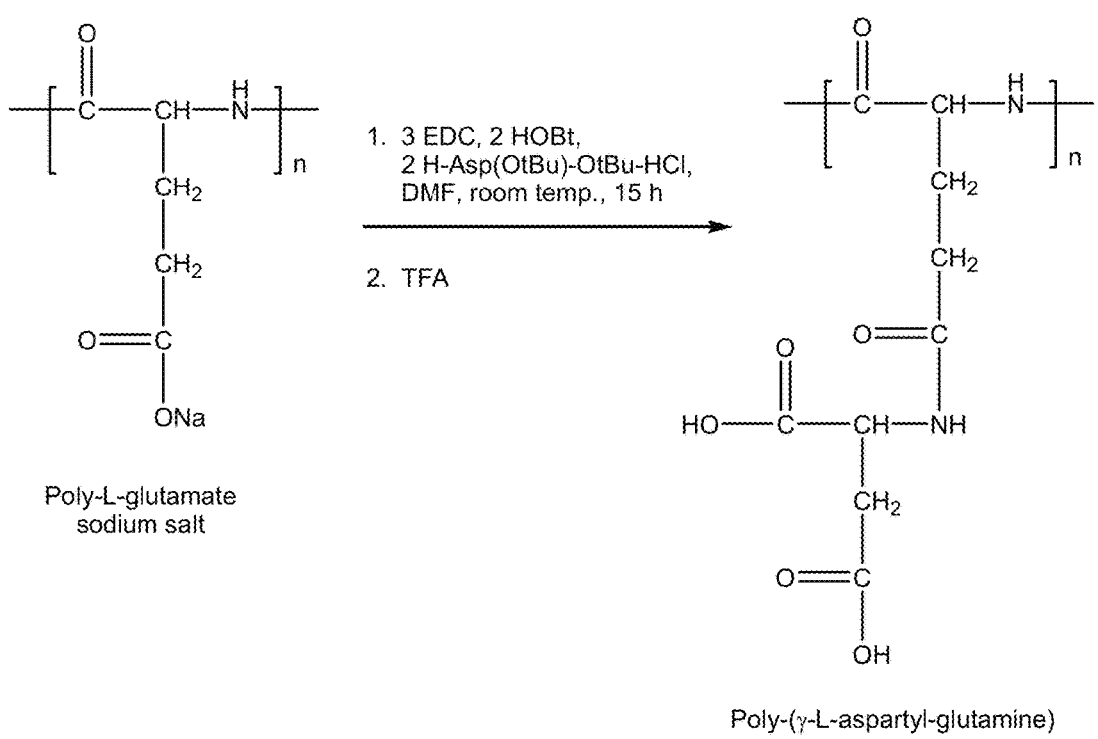
FIG. 3 illustrates another reaction scheme for the preparation of poly-(γ-L-aspartyl glutamine).

A poly-($\gamma$-L-aspartyl-glutamine) was prepared according to the general scheme illustrated in FIG. 3 as follows:

Polyglutamate sodium salt (10.0 g) with an average molecular weight of 49,000 daltons based on the Heleos system with MALS detector, EDC (33.8 g), HOBt (15.9 g), and H-asp(OtBu)-(OtBu)-HCl (32.0 g) were mixed in DMF (700 mL). The reaction mixture was stirred at room temperature for 15-24 hours, and then poured into a water solution (3 L). A white precipitate formed, and was filtered and washed with water. The intermediate polymer was then freeze-dried. The structure of the intermediate polymer was confirmed via $^1$H-NMR by the presence of a peak for the O-tBu group at 1.4 ppm.

The intermediate polymer was treated with TFA (200 mL) for 5 hours. Then, the TFA was partially removed by rotary evaporation. Water was added to the residue and the residue was dialyzed using semi-membrane cellulose (molecular weight cut-off 10,000 daltons) in reverse-osmosis water (4 time water changes) overnight. Poly-($\gamma$-L-aspartyl-glutamine) was transparent at pH 7 in water after dialysis. Poly-($\gamma$-L-aspartyl-glutamine) (15.0 g) was obtained as white powder after being lyophilized. The polymer structure was confirmed via $^1$H-NMR by the disappearance of the peak for the O-tBu group at 1.4 ppm. The average molecular weight of poly-($\gamma$-L-aspartyl-glutamine) was measured and found to be 99,400 daltons.

Examples 3a-3b

Synthesis of poly-($\gamma$-L-aspartyl-glutamine) from starting polyglutamate sodium salts with different average molecular weights (19,800 and 9,400 daltons based on the Heleos system with MALS detector) was carried out using the procedure in Example 3, and the average molecular weight of the poly-(γ-L-aspartyl-glutamine) resulting polymers were measured and found to be 39,700, and 17,700 daltons, respectively.

Example 4

Figure 4:
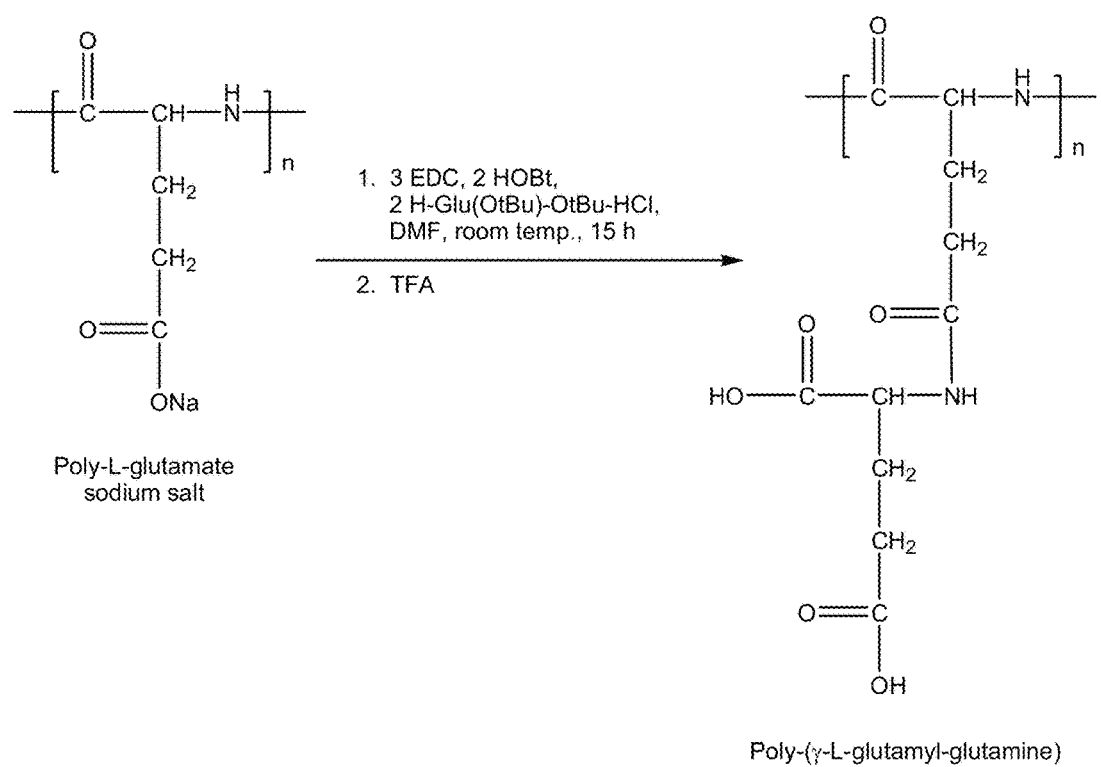
FIG. 4 illustrates a reaction scheme for the preparation of poly-(γ-L-glutamyl glutamine).

A poly-(γ-L-glutamyl-glutamine) was prepared according to the general scheme illustrated in FIG. 4 as follows:

Polyglutamate sodium salt (0.40 g) having an average molecular weight of 19,800 daltons based on the Heleos system with MALS detector, EDC (1.60 g), HOBt (0.72 g), and H-glu(OtBu)-(OtBu)-HCl (1.51 g) were mixed in DMF (30 mL). The reaction mixture was stirred at room temperature for 15-24 hours and then was poured into distilled water solution (200 mL). A white precipitate formed and was filtered and washed with water. The intermediate polymer was then freeze-dried. The intermediate polymer structure was confirmed via $^1$H-NMR by the presence of a peak for the O-tBu group at 1.4 ppm.

The intermediate polymer was treated with TFA (20 mL) for 5-8 hours. The TFA was then partially removed by rotary evaporation. Water was added to the residue and the residue was dialyzed using semi-membrane cellulose (molecular weight cut-off 10,000 daltons) in reverse-osmosis water (4 time water changes) overnight. Poly-(γ-L-glutamyl-glutamine) was transparent at pH 7 in water after dialysis. Poly-(γ-L-glutamyl-glutamine) (0.6 g) was obtained as white powder after being lyophilized. The polymer structure was confirmed via $^1$H-NMR by the disappearance of the peak for the O-tBu group at 1.4 ppm. The average molecular weight of poly-(γ-L-glutamyl-glutamine) was measured and found to be 38,390 daltons.

Examples 4a-4c

Synthesis of poly-(γ-L-glutamyl-glutamine) from poly-L-glutamate sodium salts with different average molecular weights (49,000, 19,450, and 10,900 based on the Heleos system with MALS detector) was carried out using the procedure in Example 4. The molecular weights of their poly-(γ-L-glutamyl-glutamine) polymers were measured and found to be 110,800, 37,400, and 19,800 daltons, respectively.

Example 5

Figure 5:
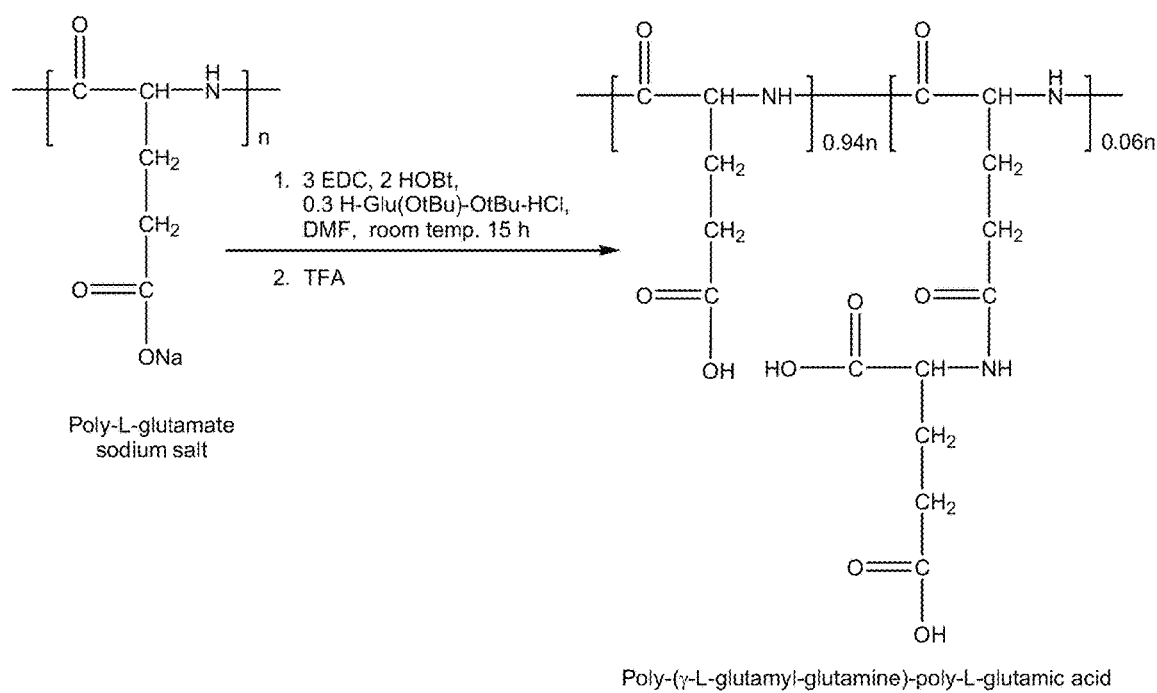
FIG. 5 illustrates a reaction scheme for the preparation of poly-(γ-L-glutamyl glutamine)-poly-L-glutamic acid.

A poly-(γ-L-glutamyl-glutamine)-poly-L-glutamic acid was prepared according to the general scheme illustrated in FIG. 5 as follows:

Polyglutamate sodium salt (0.50 g) having average molecular weight of 49,000 daltons based on the Heleos system with MALS detector, EDC (0.26 g), HOBt (0.11 g), and H-glu(OtBu)-(OtBu)-HCl (0.05 g) were mixed in DMF (30 mL). The reaction mixture was stirred at room temperature for 15-24 hours and poured into a water solution (500 mL). A white precipitate formed, and was filtered and washed with water. The intermediate polymer was freeze-dried. The intermediate polymer structure was confirmed via $^1$H-NMR by the presence of a peak for the O-tBu group at 1.4 ppm.

The intermediate polymer was treated with TFA (20 mL) for 5-8 hours. The TFA was partially removed by rotary evaporation. Water was added to the residue and the residue was dialyzed using semi-membrane cellulose (molecular weight cut-off 10,000 daltons) in reverse-osmosis water (4 time water changes) overnight. Poly-(γ-L-glutamyl-glutamine)-poly-L-glutamic acid was transparent at pH 7 in water after dialysis. Poly-(γ-L-glutamyl-glutamine)-poly-L-glutamic acid (0.25 g) was obtained as a white powder after being lyophilized. The polymer structure was confirmed via $^1$H-NMR by the disappearance of the peak for the O-tBu group at 1.4 ppm. The average molecular weight of poly-(γ-L-glutamyl-glutamine) was measured found to be 57,400 daltons.

Example 6

Figure 6:
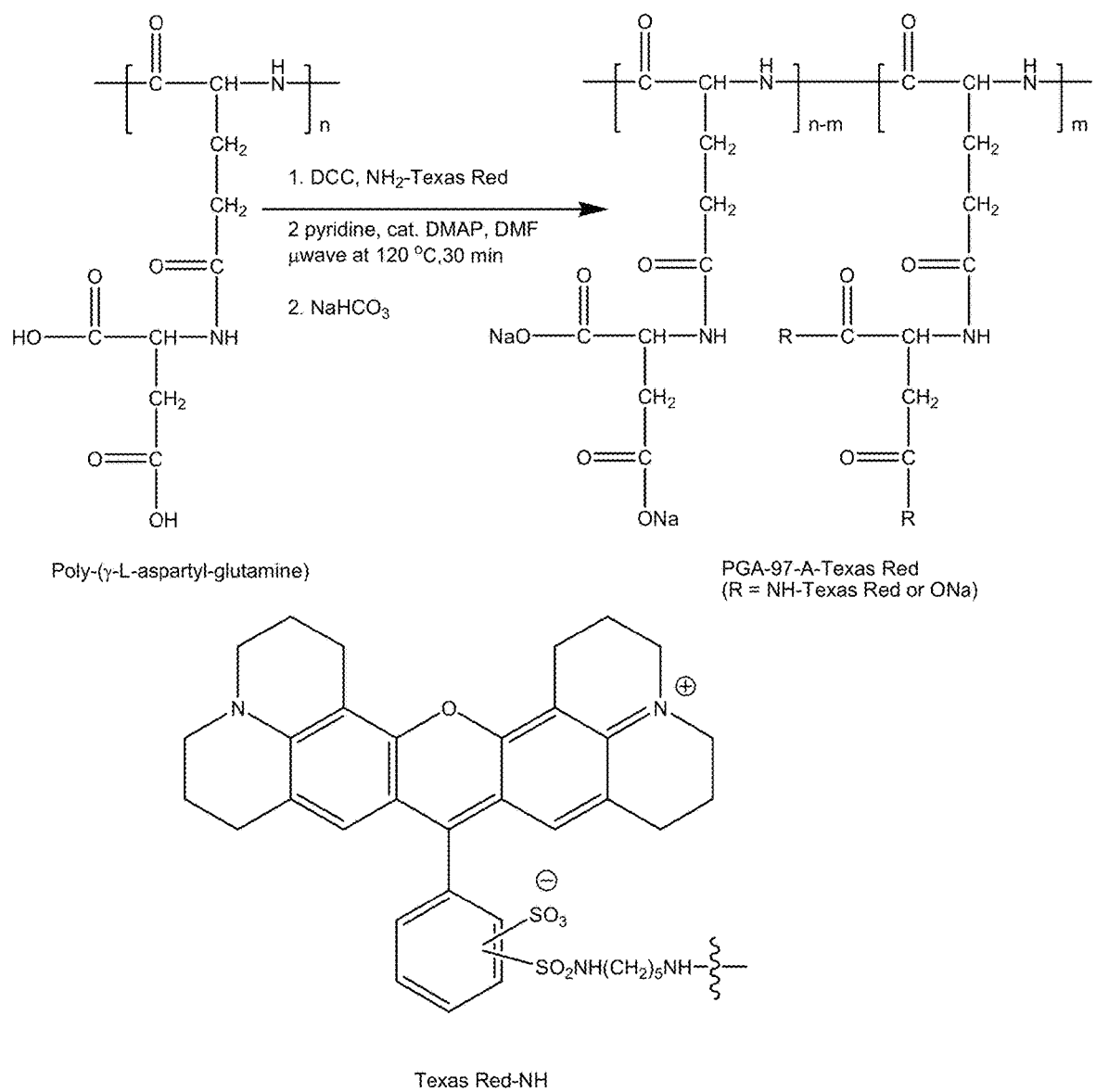
FIG. 6 illustrates a reaction scheme for the preparation of PGA-97-A-Texas Red.

A polymer conjugate referred to herein as PGA-97-A-Texas Red was prepared according to the general scheme illustrated in FIG. 6 as follows:

Poly-(γ-L-aspartyl-glutamine) average molecular weight of 99,400 daltons (100 mg) was partially dissolved in DMF (3 mL). Anhydrous DCC (130 mg), Texas Red-NH$_2$ dye (15 mg), pyridine (200 µL), and DMAP (10 mg) were added. The reaction was carried out using a microwave method at 120° C. for 30 minutes. The reaction was then cooled to room temperature. The reaction mixture was filtered into acidic water solution (200 mL, pH <2 based on pH paper). A purple precipitate formed, and was filtered and washed with water. The purple precipitate was then dissolved in acetone (50 mL). The solution was filtered into sodium bicarbonate solution (0.5 M) and dialyzed using semi-membrane cellulose (molecular weight cut-off 10,000 daltons) in reverse-osmosis water (4 time water changes) overnight. The polymer PGA-97-A-Texas Red (80 mg) was obtained as a purple solid after being lyophilized.

Example 7

Figure 7:
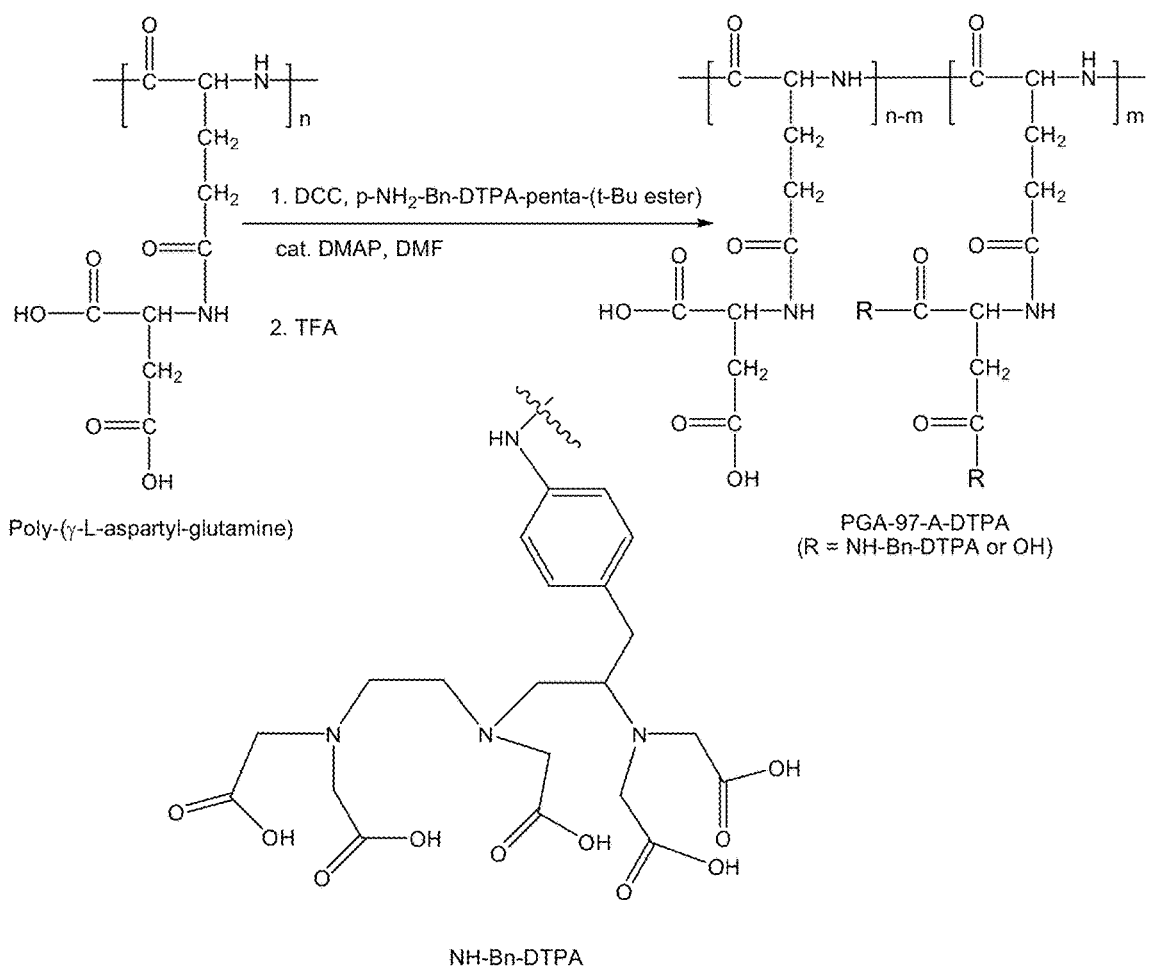
FIG. 7 illustrates a reaction scheme for the preparation of PGA-97-A-DTPA.

A polymer conjugate referred to herein as PGA-97-A-DTPA was prepared according to the general scheme illustrated in FIG. 7 as follows:

Poly-(γ-L-aspartyl-glutamine) average molecular weight of 99,400 daltons (100 mg) was dissolved in DMF (5 mL). DCC (200 mg) was then added into the solution. A solution of p-NH$_2$-Bn-DTPA-penta-(tBu ester) (400 mg) in DMF (5 mL) was also added into the reaction mixture. Anhydrous pyridine (300 µL) and the catalyst DMAP (20 mg) were then added. The reaction mixture was stirred and heated up to 120° C. for 30 minutes under microwave conditions. The reaction mixture was then cooled to room temperature, and some precipitate formed. The precipitate was filtered, and the supernatant was acidified to a pH of about 2 with diluted hydrochloric acid in water. The solution containing intermediate polymer was dialyzed in water for 2 days with cellulose membrane (molecular weight cutoff 10,000 daltons), and the intermediate polymer was lyophilized. The intermediate polymer structure was confirmed by $^1$H-NMR.

The intermediate polymer was treated with TFA for 4 hours. The TFA was then removed by rotary evaporation. The residue was dissolved in water and the solution was dialyzed in water with cellulose membrane (molecular weight cutoff-10,000 daltons). The polymer was then lyophilized. The PGA-97-A-DTPA structure was confirmed by $^1$H-NMR.

Example 8

Figure 8:
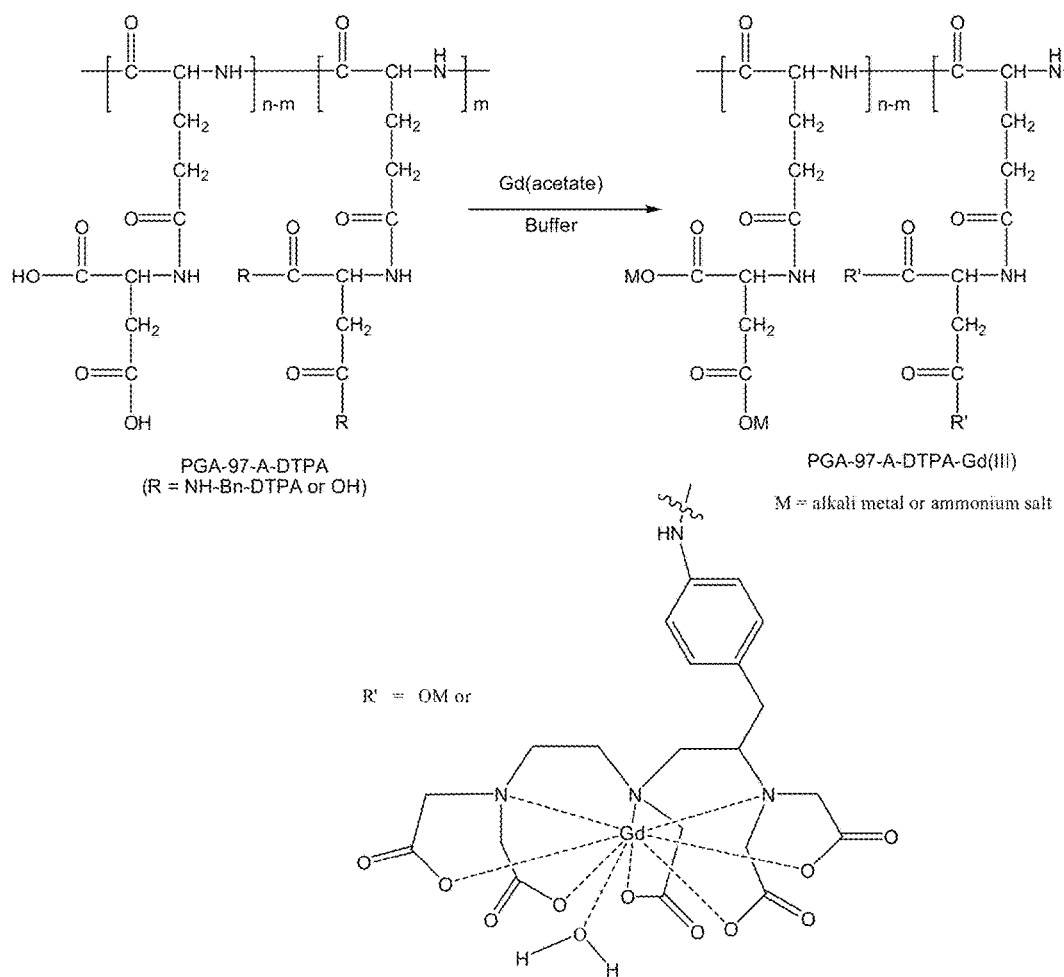
FIG. 8 illustrates a reaction scheme for the preparation of PGA-97-A-DTPA-Gd(III).

A polymer conjugate referred to herein as PGA-97-A-DTPA-Gd(III) was prepared according to the general scheme illustrated in FIG. 8 as follows:

PGA-97-A-DTPA obtained from Example 7 was treated with Gd(III)-acetate in buffer for 4 hours. The reaction solution was dialyzed in water with cellulose membrane (molecular weight cutoff-10,000 daltons) for 3 days and lyophilized to obtain the polymer (86 mg). The amount of Gd(III) was quantified by inductively coupled plasma-optical emission spectroscopy (ICP-OES) measurement. The amount of Gd(III) present was found to be 7% by weight to weight of the polymer based on Gadolinium ICP standards (Ricca Chemical Company, Arlington, Tex. (Cat No. PGD1KN-500)).

Example 9

Figure 9:
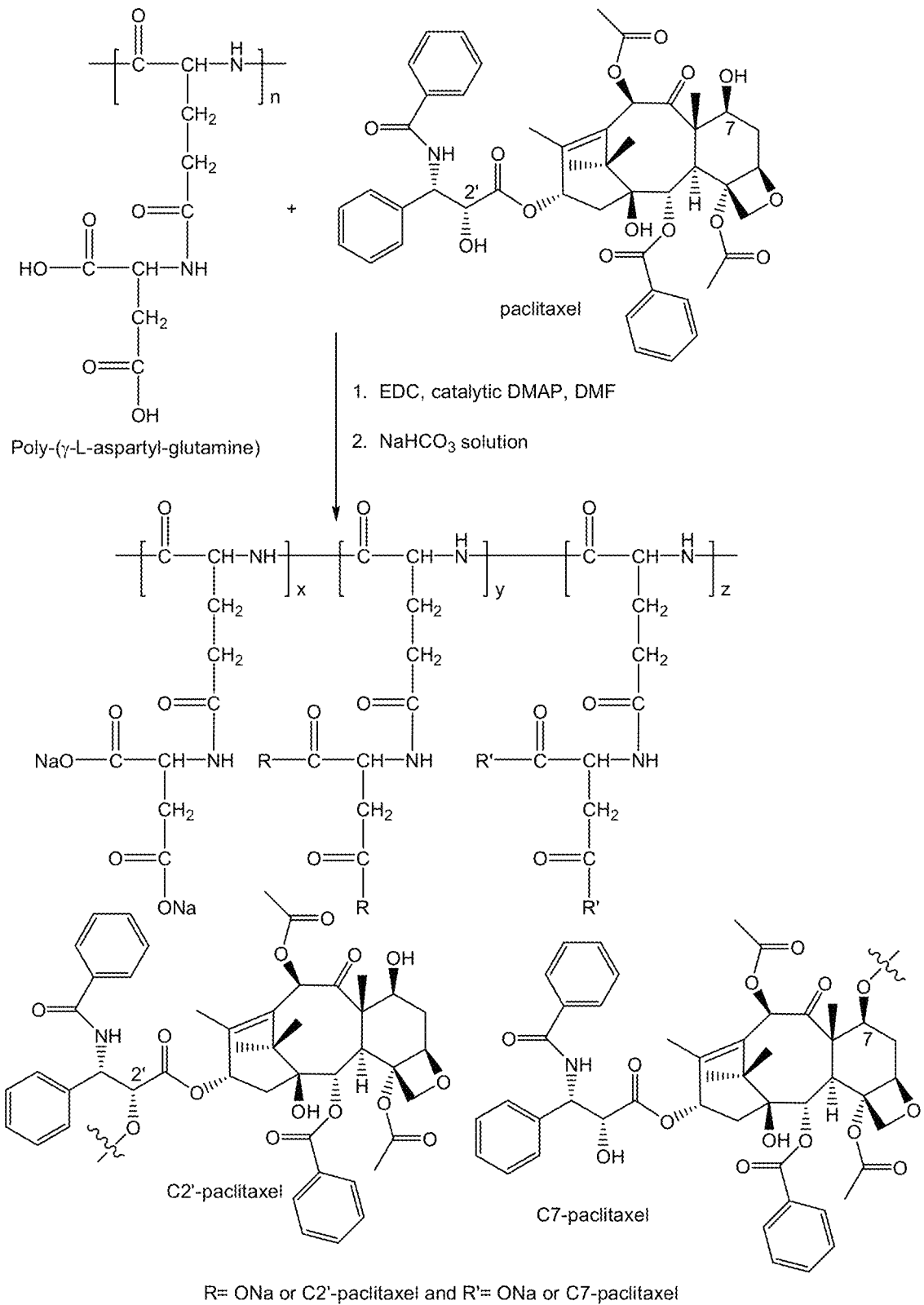
FIG. 9 illustrates a general reaction scheme for the preparation of PGA-A-PTX.

A polymer conjugate referred to herein as PGA-97-A-10 was prepared according to the general scheme illustrated in FIG. 9 as follows:

Poly-(γ-L-aspartyl-glutamine)-average molecular weight of 99,400 daltons (351 mg) was partially dissolved in DMF (40 mL). DCC (120 mg) and paclitaxel (44 mg) were added, respectively, into the mixture. DMF (10 mL) and a catalytic amount of DMAP (100 mg) were then added into the mixture. The reaction mixture was stirred at room temperature for 1 day. Completion of the reaction was verified by TLC which confirmed the absence of free paclitaxel. The mixture was poured into chloroform (300 mL) and a precipitate formed. The residue was obtained after filtration and was then re-dissolved in methanol. Precipitation was induced by adding a 0.2 N aqueous hydrochloric solution and the residue was isolated after centrifugation at 10,000 rpm. The residue was then re-dissolved in 0.5M sodium bicarbonate solution. The polymer solution was dialyzed in deionized water using a cellulose membrane (cut-off 10,000 daltons) in reverse-osmosis water (4 time water changes) for 1 day. A clear solution was obtained and freeze-dried. PGA-97-A-10 (340 mg) was obtained and confirmed by $^1$H NMR. The content of paclitaxel in PGA-97-A-10 was determined by UV spectrometry as 10% by weight to weight. The absence of free paclitaxel was also confirmed by TLC.

Example 10

A polymer conjugate referred to herein as PGA-97-A-20 was prepared according to the general scheme illustrated in FIG. 9 as follows:

Poly-(γ-L-aspartyl-glutamine)-average molecular weight of 99,400 daltons (750 mg) was partially dissolved in DMF (50 mL). EDC (450 mg) and paclitaxel (210 mg) were added, respectively, into the mixture. DMAP (100 mg), acting as a catalyst, was added into the mixture. The reaction mixture was stirred at room temperature for 1 day. Completion of the reaction was verified by TLC. The mixture was poured into a 0.2 N aqueous hydrochloric acid solution (300 mL). A precipitate formed and was collected after centrifugation at 10,000 rpm. The residue was then re-dissolved in a sodium bicarbonate solution 0.5 M NaHCO$_3$ solution. The polymer solution was dialyzed in deionized water using a cellulose membrane (cut-off 10,000 daltons) in reverse-osmosis water (4 time water changes) for 1 day. A clear solution was obtained and freeze-dried. PGA-97-A-20 (700 mg) was obtained and the structure confirmed by $^1$H NMR. The content of paclitaxel in PGA-97-A-20 was determined by UV spectrometry as 20% by weight to weight.

Examples 10a-10b

Synthesis of polymer conjugates referred to herein as PGA-44-A-20 and PGA-21-A-20 from poly-(γ-L-aspartyl-glutamine) polymers with average molecular weights of 39,700 and 17,700 daltons, respectively, was carried out using the procedure in Example 10. The content of paclitaxel in the polymers was determined by UV spectrometry as 20% by weight to weight.

Example 10c

Synthesis of a polymer conjugate referred to herein as PGA-44-A-19 from poly-(γ-L-aspartyl-glutamine) with average molecular weight of 39,700 was carried out using the procedure in Example 10, with a modification of adding a mixture of paclitaxel and $^3$H-paclitaxel instead of adding just paclitaxel. The content of paclitaxel in the polymer was determined by UV spectrometry as 19% by weight to weight.

Example 11

Figure 10:
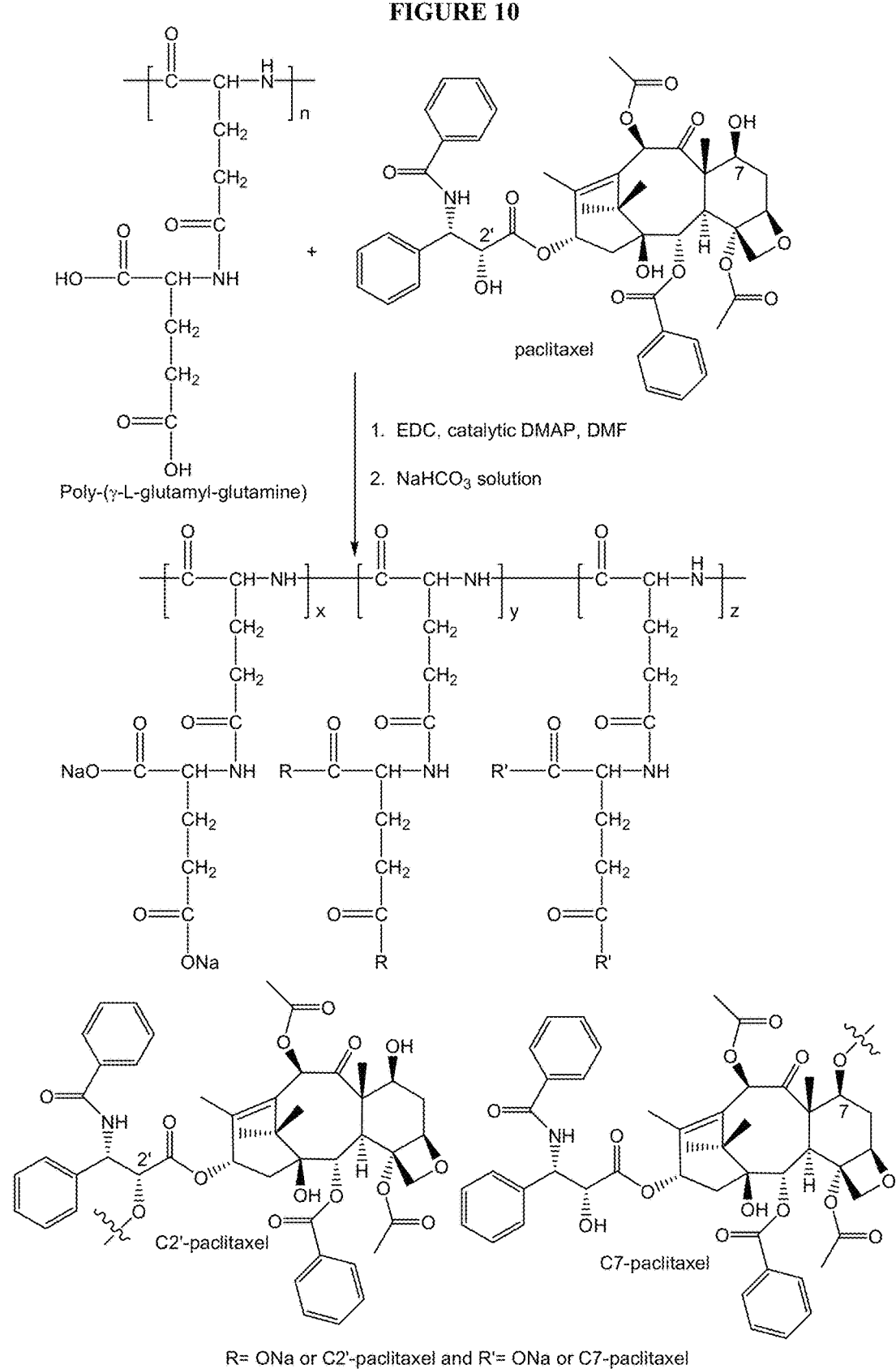
FIG. 10 illustrates a general reaction scheme for the preparation of PGA-G-PTX.

A polymer conjugate referred to herein as PGA-97-G-20 was prepared according to the general scheme illustrated in FIG. 10 as follows:

Poly-(γ-L-glutamyl-glutamine)-average molecular weight of 110,800 daltons (1.0 g was partially dissolved in DMF (55 mL). EDC (600 mg) and paclitaxel (282 mg) were added, respectively, into the mixture. DMAP (300 mg), acting as a catalyst, was added into the mixture. The reaction mixture was stirred at room temperature for 1 day. Completion of the reaction was verified by TLC. The mixture was poured into diluted 0.2N hydrochloric acid solution (300 mL). A precipitate formed and was collected after centrifugation at 10,000 rpm. The residue was then re-dissolved in sodium bicarbonate solution 0.5 M NaHCO$_3$ solution. The polymer solution was dialyzed in deionized water using a cellulose membrane (cut-off 10,000 daltons) in reverse-osmosis water (4 time water changes) for 1 day. A clear solution was obtained and freeze-dried. PGA-97-A-20 (1.1 g) was obtained and confirmed by $^1$H NMR. The content of paclitaxel in PGA-97-G-20 was determined by UV spectrometry as 20% by weight to weight.

Examples 11a-11c

Synthesis of polymer conjugates referred to herein as PGA-44-G-20, PGA-32-G-20, and PGA-21-G-20 from poly-(γ-L-glutamyl-glutamine) polymers with average molecular weights of 38,390, 37,400, and 19,800 daltons, respectively, was carried out using the procedure in Example 11. The content of paclitaxel in each of the polymers was determined by UV spectrometry as 20% by weight to weight. By increasing the amount of paclitaxel, higher loading of paclitaxel was achieved. For instance, PGA-32-G-40 was prepared from poly-(γ-L-glutamyl-glutamine) polymers having an average molecular weight of 37,400 daltons and using the procedure of Example 11. The content of paclitaxel was determined by UV spectrometry and found to be 40% weight to weight.

Examples 12a-12c

Synthesis of polymer conjugates referred to herein as PGA-97-G-24, PGA-32-G-19, PGA-21-G-19 from poly-(γ-L-glutamyl-glutamine) polymers with average molecular weights of 110,800, 37,400, and 19,800 daltons, respectively, was carried out using the procedure in Example 11, with a modification of adding a mixture of paclitaxel and $^3$H-paclitaxel instead of adding just paclitaxel. The content of paclitaxel in PGA-97-G-24, PGA-32-G-19, PGA-21-G-19 was determined by UV spectrometry as 24%, 19% and 19%, by weight to weight, respectively.

Example 13

Synthesis of C2'-PTX-Glu Protected and C7-PTX-Glu Protected

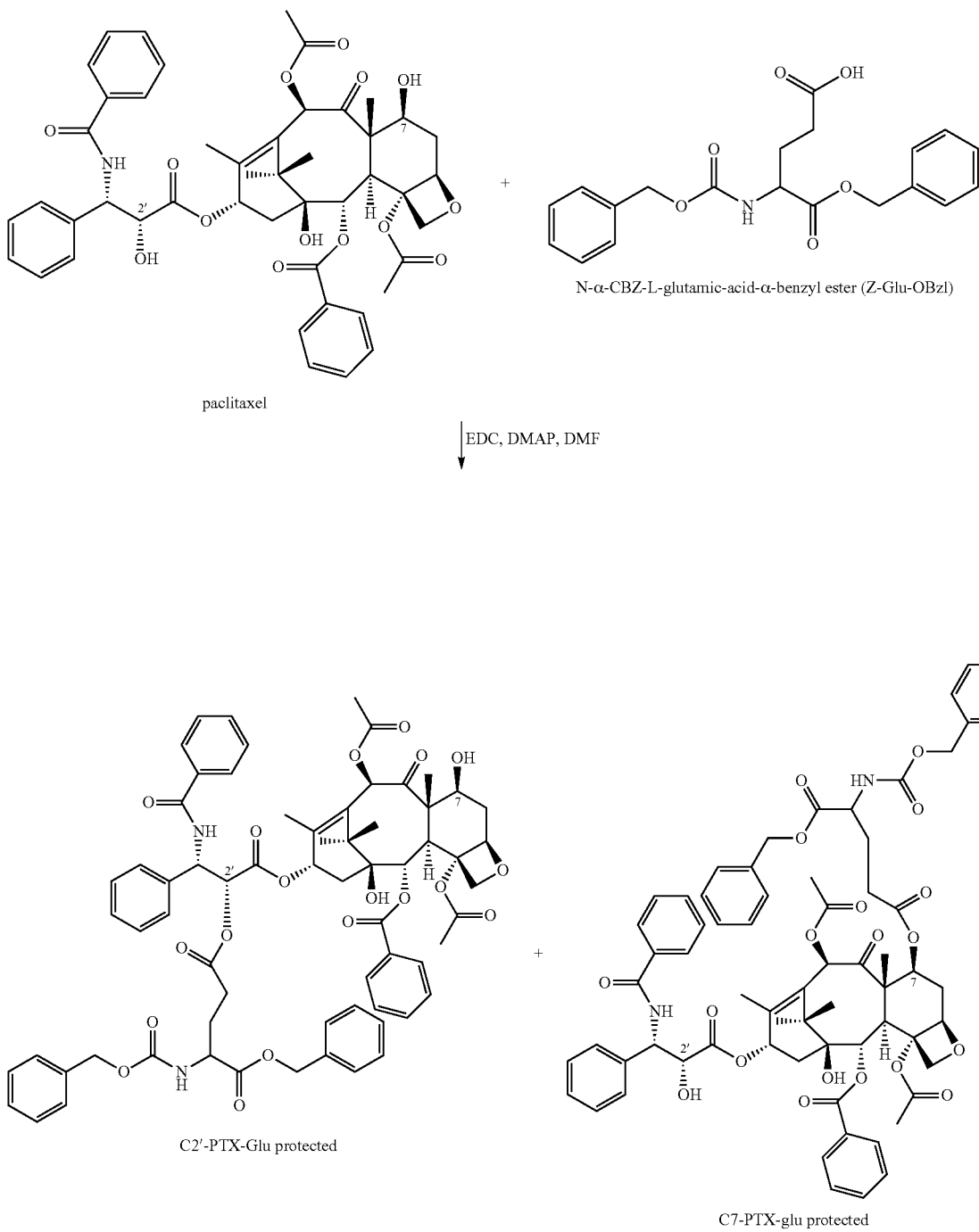

Z-Glu-OBzl (2.6 g), paclitaxel (2.0 g), EDC (1.5 g), and DMAP (300 mg) were mixed in DMF (20 mL) and stirred for 15 hours. Measurement by TLC showed no free paclitaxel left in the mixture. The mixture was then poured into 0.2N aqueous hydrochloric acid (100 mL) and organic product was extracted into ethylacetate (two times×50 mL). The organic phases were combined and washed with 0.5 M sodium bicarbonate solution (100 mL). The organic phase was then dried with anhydrous sodium sulfate. The ethylacetate was removed by rotary evaporation, and the products were purified by silica gel chromatography (hexane:ethylacetate, 1:1). $^1$H-NMR confirmed the resulting products were C2'-PTX-Glu protected (2.2 g) and C7-PTX-glu protected (0.42 g).

Example 13a

Synthesis of C2'-PTX-Glu

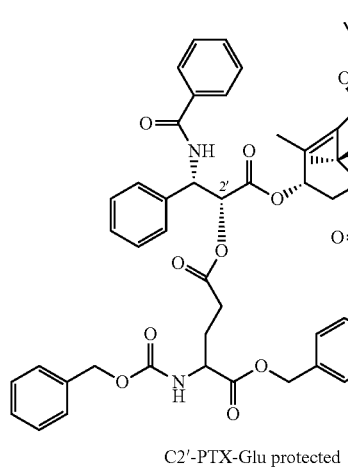

C2'-PTX-Glu protected

C2'-PTX-Glu

Example 13b

Synthesis of C7-PTX-Glu

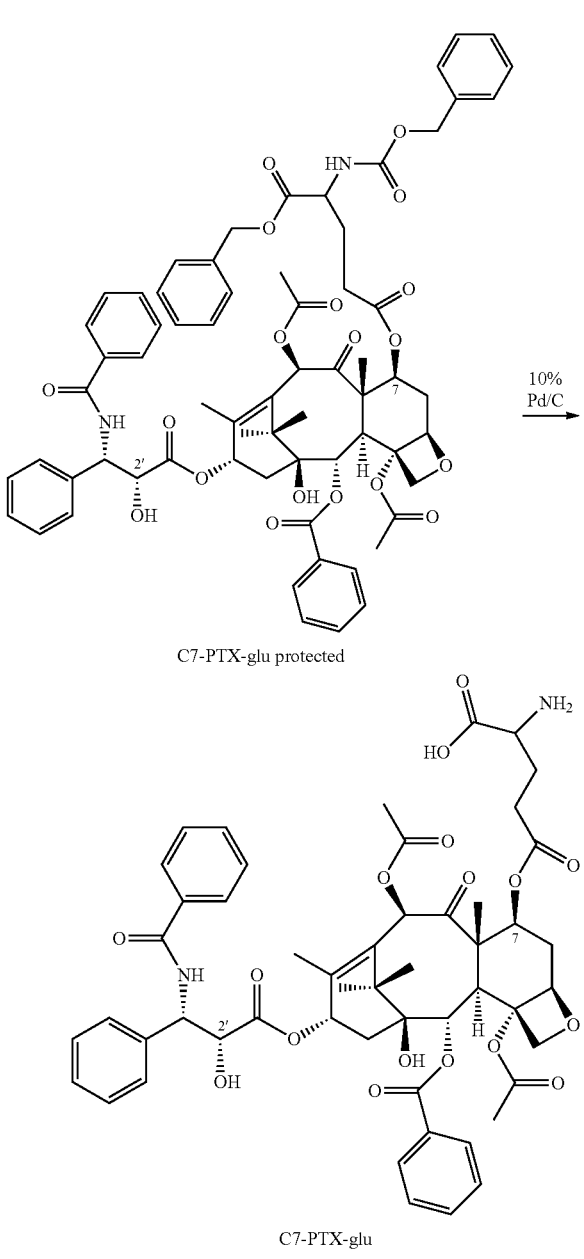

C7-PTX-glu protected

C7-PTX-glu

Figure 11:
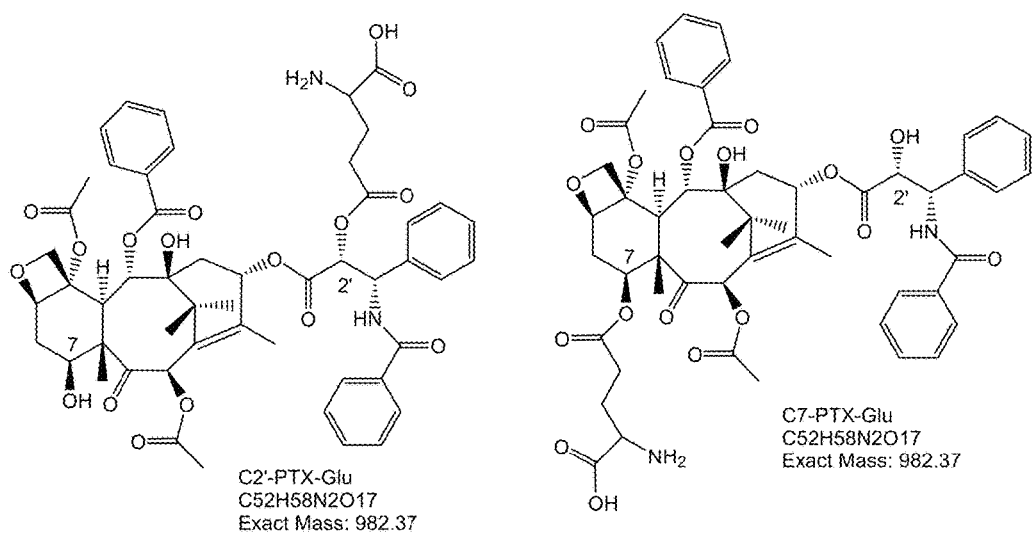
FIG. 11 illustrates the chemical structures of C2'-paclitaxel-glutamic acid and C7-paclitaxel-glutamic acid, and their HPLC and LC-MS times.

C2'-PTX-Glu protected (2.2 g) and 10% Pd/C (0.20 g) were stirred in deoxygenated methanol (150 mL). Hydrogen gas was introduced using a balloon. The reaction was hydrogenated for four hours. TLC verified the reaction went to completion. The solution was filtered through 0.2-μm filter. The solution was clear and the methanol was removed by rotary evaporation. The crude product was further purified by reverse-phase HPLC using gradient water and acetonitrile. C2'-PTX-Glu (600 mg) was obtained after HPLC purification and freeze-dried, and the product was confirmed by LC-MS. The result is shown in FIG. 11. C2'-PTX-glu had an HPLC time of about 32 minutes and an LC-MS time of about 6.2 minutes.

C7-PTX-Glu protected (250 mg) and 10% Pd/C (0.20 g) were stirred in a solution of deoxygenated methanol (150 mL). Hydrogen gas was introduced into the solution using a balloon, and the reaction was hydrogenated for four hours. After reaction went to completion as shown by TLC measurement, the solution was filtered through a 0.2-μm filter. The solution was clear and, the methanol was removed by rotary evaporation. The crude product was further purified by reverse-phase HPLC using gradient water and acetonitrile. C7-PTX-Glu (30 mg) was obtained after HPLC purification and freeze-dried, and the product was confirmed by LC-MS. The result is shown in FIG. 11. C7-PTX-glu had an HPLC time of about 35 minutes and an LC-MS time of about 6.4 minutes.

Example 14

Figure 12:
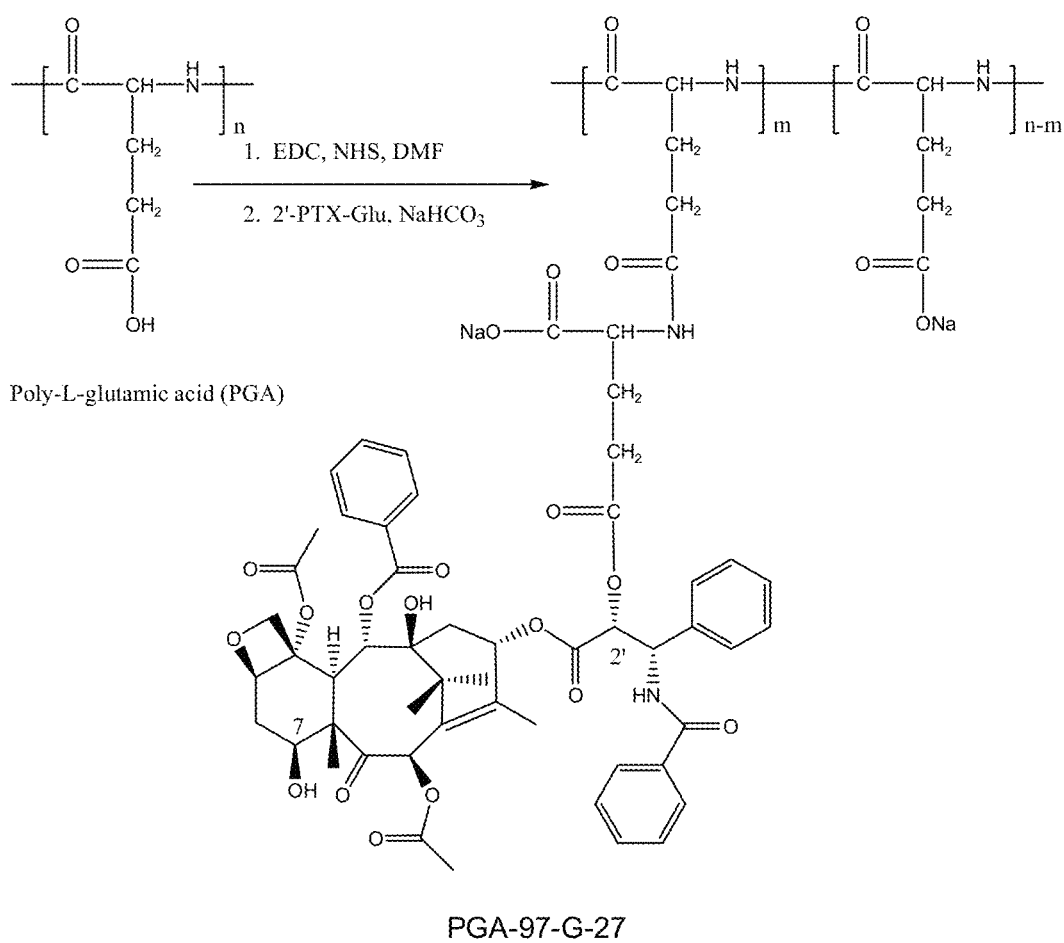
FIG. 12 illustrates a reaction scheme for the preparation of PGA-97-G-27.

The polymer conjugate referred to herein as PGA-97-G-27 was prepared according to the general scheme illustrated in FIG. 12 as follows:

Poly-L-glutamic acid (210 mg) was dissolved in DMF (10 mL). EDC (65% by mole) and NHS (65% by mole) were added to the mixture and it was stirred for 15 hours. A solution of C2'-PTX-Glu (105 mg) in DMF (2 mL) was then added to the mixture. Next, a 0.5 M sodium bicarbonate solution (3 mL) was added. The reaction mixture was stirred for 3 hours, and then poured into a diluted 0.2N hydrochloric acid solution (300 mL). A precipitate formed and was collected after centrifugation at 10,000 rpm.

The residue was then re-dissolved in a 0.5 M sodium bicarbonate solution. The polymer solution was dialyzed in deionized water using a cellulose membrane (cut-off 10,000 daltons) in reverse-osmosis water (4 time water changes) for 1 day. A clear solution was obtained and freeze-dried. The resulting product was PGA-97-G-27 (250 mg), and was confirmed by $^1$H NMR. The content of paclitaxel in PGA-97-G-27 was determined by UV spectrometry as 27% by weight to weight.

Example 15

Synthesis of PGA-97-G-Doxorubicin

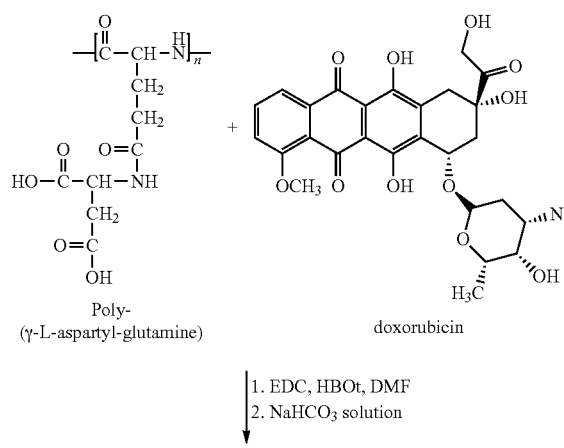

Poly-(γ-L-aspartyl-glutamine) (70 mg), doxorubicin (30 mg), EDC (50 mg), HOBt (15 mg) were dissolved in DMF (4 mL). The mixture was placed in a microwave at 120° C. for 10 minutes, and then was poured into a solution of 0.2N hydrochloric acid. A precipitate formed and was collected. The residue was re-dissolved in a diluted 0.5M sodium bicarbonate solution and dialyzed in deionized water using a cellulose membrane (cut-off 10,000 daltons) in reverse-osmosis water (4 time water changes) for 1 day. A clear red solution was obtained and freeze-dried. The structure of the resulting product of PGA-97-G-Doxorubicin (80 mg) was confirmed by $^1$H NMR.

Example 16

Synthesis of PGA-97-G-Camptothecin

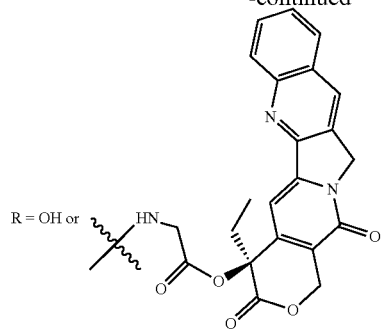

Poly-(γ-L-aspartyl-glutamine) (70 mg), glycyl-camptothecin (30 mg), EDC (50 mg), HOBt (15 mg) were dissolved in DMF (4 mL). The mixture was heated in a microwave at 120° C. for 10 minutes. The mixture was poured into DCM (150 mL), and a precipitate formed. The residue was sonificated in a solution of diluted 0.2N hydrochloric acid for 15 minutes. The resulting solid was filtered, washed with distilled water, and then freeze-dried. PGA-97-G-Camptothecin was collected as light yellow solid (50 mg).

Example 17

Solubility

The solubility of various polymers was tested at different pH levels and compared to a control of Poly-L-glutamic acid (PGA-19,800), average molecular weight of 19,800 daltons. The polymers tested were Poly-(γ-glutamyl)-poly-L-glutamine (PGPG-19,800), with average molecular weight of 19,800 daltons; Poly-(γ-glutamyl)-poly-L-glutamine (PGPG-37,400), with average molecular weight of 37,400 daltons; Poly-L-glutamate-paclitaxel-20% (PGA(32k)-PTX-20), which was prepared from starting polymer PGA-19,800 and having a content of paclitaxel of 20% weight by weight; PGA-21-G-20, which was prepared from a starting polymer of poly-(γ-glutamyl)-poly-L-glutamine-19,800 and having a content of paclitaxel of 20% weight by weight; and PGA-32-G-20, which was prepared from a starting polymer of poly-(γ-glutamyl)-poly-L-glutamine-37,400 and having a content of paclitaxel of 20% weight by weight.

Each polymer (5 mg) was added into a pH buffer (1 mL) and the mixture was sonificated for 2 minutes. Then the mixture was allowed to settle at room temperature for 30 minutes. Solubility was observed by eye and recorded on the scale of 1 to 10, where 1 is highly insoluble, 5 is a cloudy suspension, and 10 is a highly clear solution. The results are shown in the following Table 1.

TABLE 1

| | Solubility | | | | | | |
|---|---|---|---|---|---|---|---|
| | pH | | | | | | |
| Polymer | 2 | 3 | 4 | 5 | 6 | 7 | 7.4 |
| PGA-19,800 | 1 | 1 | 2 | 4 | 10 | 10 | 10 |
| PGPG-19,800 | 10 | 10 | 10 | 10 | 10 | 10 | 10 |
| PGPG-37,400 | 10 | 10 | 10 | 10 | 10 | 10 | 10 |
| PGA(32k)-PTX-20 | 1 | 1 | 2 | 10 | 10 | 10 | 10 |
| PGA-21-G-20 | 2 | 4 | 10 | 10 | 10 | 10 | 10 |
| PGA-32-G-20 | 2 | 4 | 10 | 10 | 10 | 10 | 10 |

Example 18a

Cell Culture and Preparation:

B16F0 cells were purchased from ATCC (CRL-6322, ATCC American Type Culture Collection, Rockville, Md.) and were grown in Dulbecco's modified Eagle's medium (DMEM) with 10% fetal bovine serum and 100 units/mL penicillin. The cells were grown at 37° C. in 5% $CO_2$ environment. The culture medium was removed and discarded. The cells were rinsed with Dulbecco Phosphate Buffer Solution (DPBS), Trypsin-ethylenediaminetetra-acetic acid (EDTA) solution (0.5 ml) was added, and the cells were observed under an inverted microscope to make sure that they were dispersed. Complete growth medium (6.0 to 8.0 ml) was added, and the cells were aspirated by gently pipetting. The cell suspension in appropriate aliquots was transferred to new culture plates. The cells were allowed to grow at 37° C. in 5% $CO_2$ for 24 hours before further experiments.

Example 18b

In Vitro Cellular Uptake Studies

PGA-97-A-Texas Red and Texas Red dye (TR) were separately dissolved in DPBS. Both solutions containing the dye were added to the cells at the final concentration of 0.1 μM to 10 μM. The cells with the compounds were incubated at 37° C. for 8-24 hours, after which the cells were washed 3 times with DPBS. The treated cells were examined under an OLYMPUS fluorescence microscope, and the excitation and emission wavelengths were measured at 591 and 612 nm, respectively. The results show that the cells did uptake the Texas red dye from PGA-97-A-Texas Red but not from Texas Redalone.

Three sample containers containing approximately the same number of B16F0 melanoma cells were incubated with PGA-97-A-Texas Red at 1 μM, PGA-97-A-Texas Red at 0.1 μM, and Texas Red alone at 10 μM, respectively, for 24 hours. Photographs of the in vitro cellular uptake of each container were taken with the camera on an Olympus fluorescence microscope system. In the photograph of the sample with PGA-97-A-Texas Red at 1 μM, approximately 30% of the cells were red. In the photograph of the sample with PGA-97-A-Texas Red at 0.1 μM, approximately 10% of the cells were red. In the photograph of the sample Texas Red alone at 10 μM, 0% of the cells were red. These results show that the cells uptake dye from PGA-97-A-Texas Red, but do not uptake dye from the Texas red dye alone. The polymer conjugate is effective for intercellular drug delivery.

Example 18c

The cellular uptake was also confirmed by confocal microscopy (Olympus FV1000). Nuclei of the cells were stained with Hoechst 33342 for 5-20 minutes, washed with DPBS 2-3 times, and observed under a laser scan confocal microscope. The excitation and emission wavelengths of Hoechst 33342 were measured at 405 and 461 nm, respectively. Texas Red (TR) was excited with a 543 nm laser, and detected at 615 nm under the environment of 5% $CO_2$ at 37° C. The results show that the Texas red dye from PGA-97-A-Texas Red was up taken by B16F0 cells after 24 hrs exposure. The Texas red dye from PGA-97-A-Texas Red was found in cytoplasma and excluded from the nucleus.

Photographs showing in vitro cellular uptake of PGA-97-A-Texas Red at 1 μM from confocal microscopy (Olympus FV100) were taken to compare uptake in the cytoplasm and uptake in the nucleus. The photographs show that PGA-97-A-Texas Red was up taken by B16F0 cells after 24 hrs exposure. PGA-97-A-Texas Red was found in cytoplasm and excluded from the nucleus.

Example 19

Syngeneic Tumor Model

Animals: Nu/nu mice, female, 6-8 weeks (22-25 g). Solitary tumors were produced by injecting $2 \times 10^5$ murine melanoma cells (B16F0) to the right thigh subcutaneously. 5-7 days later when the tumor reached about 500 mm$^3$, the PGA-97-A-Texas Red or Texas Red dye was injected intravenously to the tumor.

Example 20

PGA-97-A-Texas Red or TR Administration and Cryostat Section

PGA-97-A-Texas Red and Texas Red were separately dissolved in DPBS and were filtrated through a 0.2 μm filter before being administrated to the animals. 100 μl of PGA-97-A-Texas Red (TR loading at 2.5%) or Texas Red at 0.1-10 mM was intravenously injected to the tumor using the syngeneic tumor model in Example 19. Tumors were dissected, embedded under optimal cutting temperature and frozen in liquid nitrogen. Cryostat sections (6-15 μm) were made and were fixed with 4% paraformaldehyde with 0.03M of sucrose on ice for 10-30 min. The sections were washed 2 times with DPBS, stained with Hoechst 33342 (1 μg/ml) for 10 minutes, and washed again with DPBS. The sections were then mounted with a fluorescent mounting medium (DakoCytomation) and covered with a coverslip. The cryostat sections of the tumor were observed under laser scan confocal microscopy. The images showed that Texas red dye from PGA-97-A-Texas Red accumulated into the tumor cells in vivo after 24 hours of intravenous administration of the PGA-97-A-Texas Red but not with Texas Red dye alone Photographs of the cryostat cross-section of in vivo tumor tissue uptake of PGA-97-A-Texas Red and Texas Red dye alone were taken. For each, three different cross-sections were taken for a total of six images. Three photographs of different cross-sections of the Texas Red dye alone were observed as green, orange-yellow, and essentially black. Three photographs of different cross sections of the PGA-97-A-Teas Red were observed as green, orange-yellow, and some red area. Texas Red dye from PGA-97-A-Texas Red was observed in tumor tissues in one of the photographs. On the other hand, Texas Red dye was not observed in the similar photograph of Texas Red alone. These results show that Texas red dye from PGA-97-A-Texas Red accumulated into the tumor cells in vivo after 24 hours of intravenous administration of the PGA-97-A-Texas Red, but did not with Texas Red dye alone.

Additionally, the Texas red dye from PGA-97-A-Texas Red could also be seen in the endothelial cells along the blood vessel of the tumor. Additional photographs were taken of another cryostat cross-section of the tumor tissue. Red dye was observed along the blood vessel after 24 hours of tail vein intravenous administration of the PGA-97-A-Texas Red. The results show the PGA-97-A-Texas Red could be seen in the endothelial cells along the blood vessel of the tumor Example 21

In Vitro Cytotoxicity MTT Studies

Figure 13:
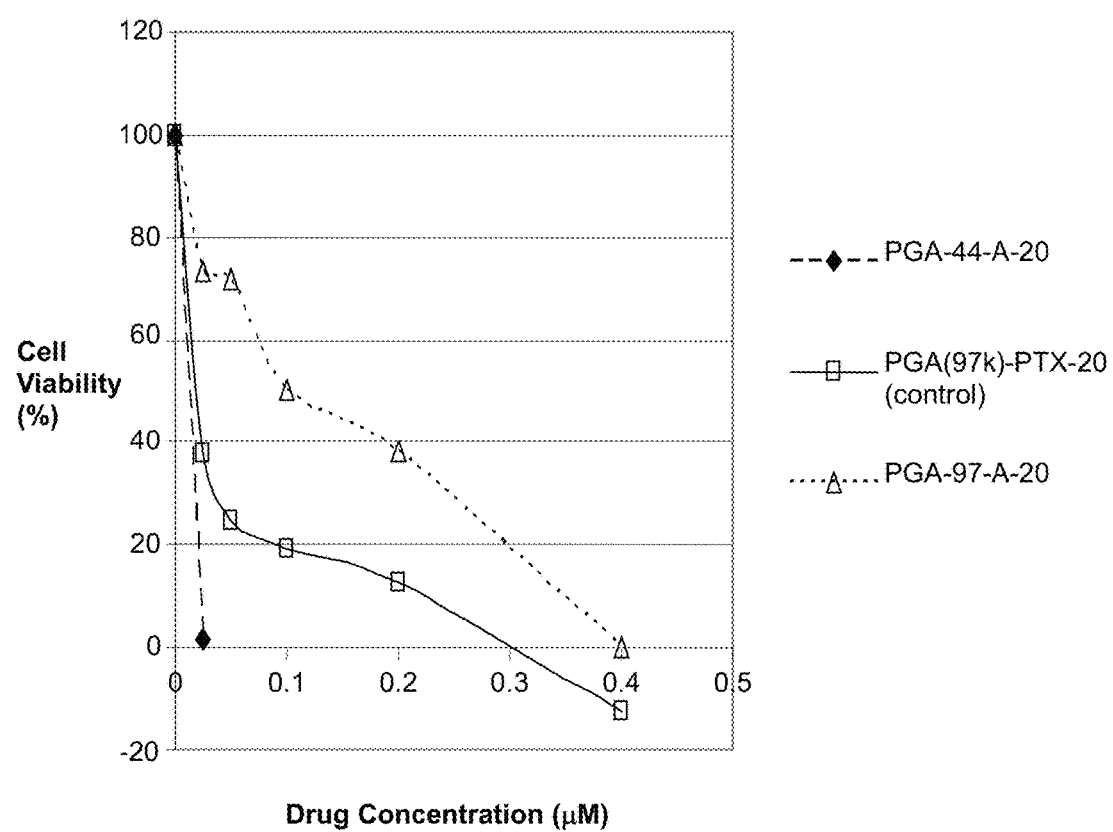
FIG. 13 shows a plot that illustrates the effect of PGA-44-A-20, PGA-97-A-20, and PGA(97k)-PTX-20 (control) on the proliferation of B16F0 melanoma cells at several different concentrations of the drug.

Polymers conjugates described herein containing paclitaxel were evaluated for their effect on the proliferation of B16F0 melanoma cells at several different concentrations of the drug. Cytotoxic MTT assay was carried out as reported in Monks et al. *JNCI* 1991, 83, 757-766, which is hereby incorporated by reference in its entirety. PGA-44-A-20 was prepared as in Examples 10a, from poly(γ-L-aspartyl-glutamine) having an average molecular weight of 39,700 daltons based on the Heleos system with MALS detector, and the weight percentage of paclitaxel in the polymer was 20% weight by weight. PGA-97-A-20 was prepared as in Example 10, from poly(γ-L-aspartyl-glutamine) having an average molecular weight of 99,400 daltons based on the Heleos system with MALS detector, and the weight percentage of paclitaxel in the polymer was 20% weight by weight. PGA(97k)-PTX-20 was used as the control polymer of this example and was prepared according to the previous literature procedure from poly-L-glutamic acid having average molecular weight of 49,000 daltons based on the Heleos system with MALS detector, the weight percentage of paclitaxel in the polymer is 20% weight by weight (See Li et al., "Complete Regression of Well-established tumors using a novel water soluble poly(L-glutamic acid)-paclitaxel conjugate." *Cancer Research* 1998, 58, 2404-2409). The results are shown in FIG. 13. The viability of the melanoma cells decreased with increased drug concentration as shown in FIG. 13. These results indicate that PGA-44-A-20 and PGA-97-A-20 are effective anti-cancer agents.

Example 22

In Vitro Cytotoxicity MTT Studies

A polymer conjugate containing paclitaxel was compared to a control polymer, a polymer not containing paclitaxel, and a control of Taxol without polymer to view their effect on proliferation of B16F0 melanoma cells at several different concentrations of the drug. Cytotoxic MTT assay was carried out as reported in Monks et al. *JNCI* 1991, 83, 757-766. PGA-97-A-10 was prepared as in Example 9, from poly(γ-L-aspartyl-glutamine) with average molecular weight of 99,400 daltons based on the Heleos system with MALS detector, and the weight percentage of paclitaxel in the polymer was 10%. PGA(97k)-PTX-10 used as the control polymer of this example was prepared according to the previous literature (Li et al. "Complete Regression of Well-established tumors using a novel water soluble poly(L-glutamic acid)-paclitaxel conjugate." *Cancer Research* 1998, 58, 2404-2409), from poly-L-glutamic acid with average molecular weight of 49,000 daltons based on the Heleos system with MALS detector, the weight percentage of paclitaxel in the polymer is 10%. The polymer not containing paclitaxel was poly-(γ-L-aspartyl-glutamine) sodium salt.

Figure 14:
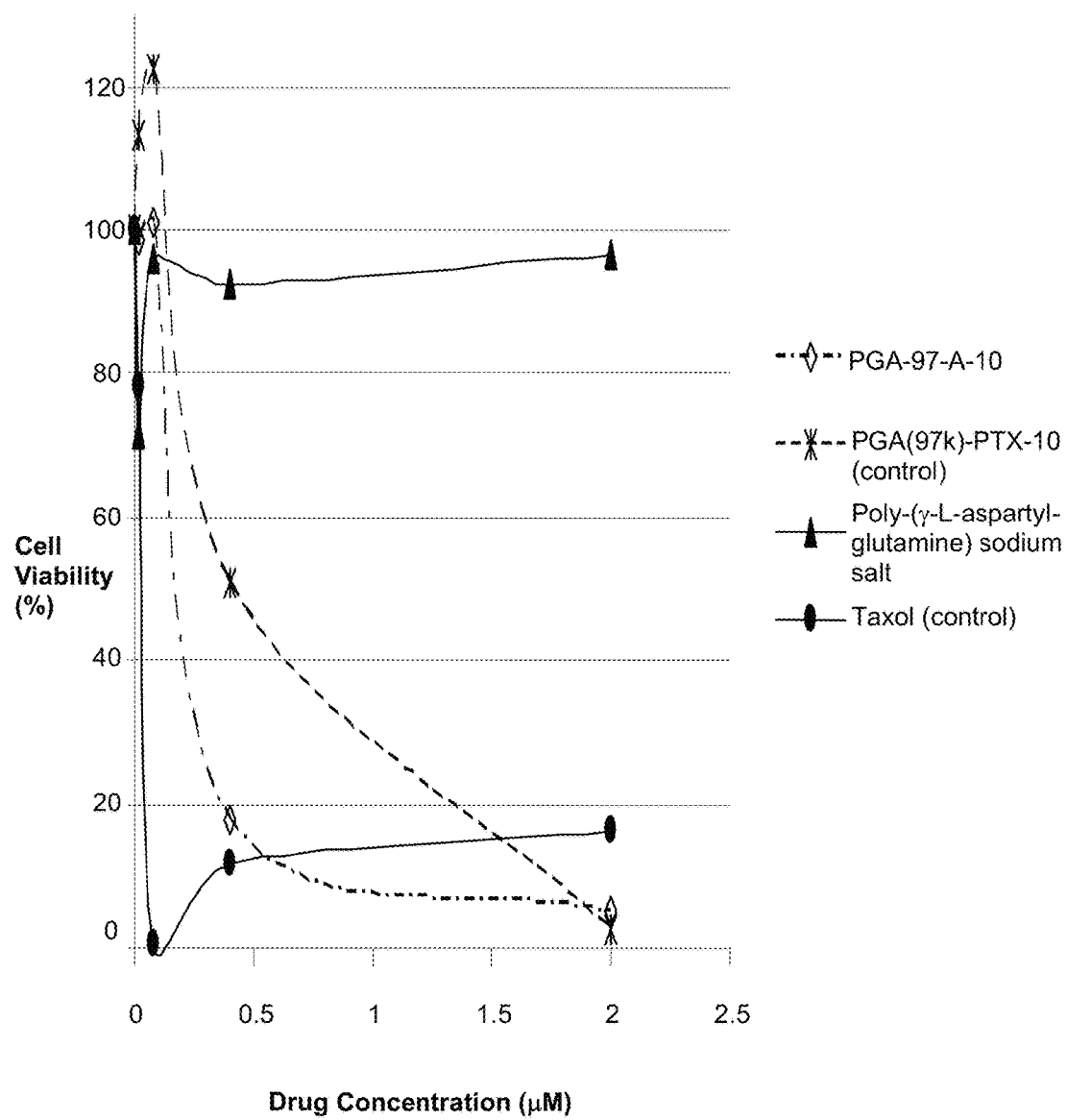
FIG. 14 shows a plot that illustrates the effect of PGA-97-A-10, PGA(97k)-PTX-10, poly-(γ-L-aspartyl glutamine) sodium salt, and Taxol on the proliferation of B16F0 melanoma cells at several different concentrations of the drug.

The results are shown in FIG. 14. The sodium salt polymer having no anti-tumor drug had little effect on the viability of the melanoma cell. Additionally, PGA-97-A-10 compared favorably to the control polymer containing the anti-tumor drug. As shown by FIG. 14, PGA-97-A-10 acts as an effective anti-cancer agent.

Example 23

Animals and Tumor Models for Pharmacokinetic Studies

Nude mice (6-7 weeks old, body weight 25-30 grams, female) were purchased from Charles River Lab (Willington, Mass.). B16F0 cell lines were purchased from ATCC (CRL-6322, ATCC American Type Culture Collection, Rockville, Md.). The B16F0 cells were cultured in DMEM supplemented with 10% Fetal bovine serum, 2 µM Glutamine, 1 mM non-essential amino acids, 1 mM sodium pyruvate, 100 U/ml penicillin and 100 ug/ml streptomycin. The B16F0 cells harvested from tissue culture were counted and re-suspended to a concentration of $5 \times 10^6$ per mL. Using a TB syringe, 0.4 mL (a total of $2 \times 10^6$ cells) was administered via subcutaneous injection into each mouse. Four tumors were inoculated per animal at the right shoulder, the left shoulder, the right hip, and left hip.

Example 23a

At the point when the mean tumor volume for the entire population of mice from Example 23 had reached 200-300 mm$^3$ (6-8 mm diameter), each tumor bearing animal received a single IV bolus injection of $^3$H-Taxol (control) or PGA-44-A-19 via a tail vein.

Figure 15:
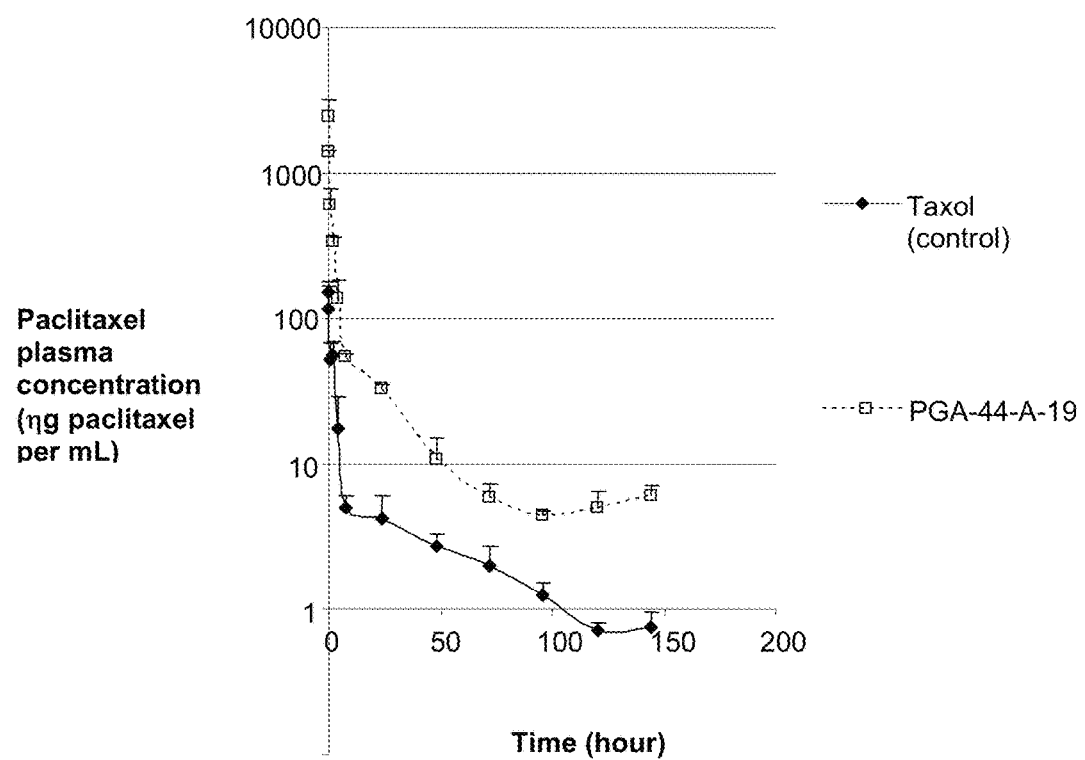
FIG. 15 shows a plot that illustrates the paclitaxel plasma concentrations of PGA-44-A-19 and Taxol on B16F0 melanoma tumors in nude nu/nu mice over time.

PGA-44-A-19 was prepared as in Example 10c, from poly(γ-L-aspartyl-glutamine) with an average molecular weight of 39,700 daltons based on the Heleos system with MALS detector, and the weight percentage of paclitaxel in the polymer was 19% weight by weight. The control for this example was Taxol. The dose of free $^3$H-Taxol (control) and PGA-44-A-19 was 20 mg paclitaxel equivalents/kg. For each drug, groups of 4 mice were anesthetized at various time points (each unit is in hours): 0 (i.e. as quickly as possible after the IV injection), 0.083, 0.25, 1.0, 2.0, 4.0, 8.0, 48, 72, 96, 120, and 144. A collection of 0.5 ml of blood obtained by cardiac or retro-orbital puncture was made into heparinized tubes. Thereafter, mice were sacrificed before recovering from anesthesia. The blood samples of each mouse were centrifuged at 11,000 rpm. The supernatant plasma (0.2-0.3 mL) from the blood samples were collected and transferred into a new vial. 0.1 mL of the plasma of each sample was separately transferred into a new 10-mL vial, and a liquid scintillation solution (5 mL) was added to the vial. The content of paclitaxel was analyzed using a liquid scintillation LS6500 counting system (Beckman) and calculated from the standard curve of each sample. The results are shown in FIG. 15. The paclitaxel concentration of PGA-44-A-19 remained much higher over a longer period of time. These results indicate that paclitaxel in PGA-44-A-19 has longer term effectiveness in blood circulation than compared to Taxol alone.

Example 24

At the point when the mean tumor volume for the entire population of mice from Example 23 had reached 200-300 mm$^3$ (6-8 mm diameter), each tumor bearing animal (nude nu/nu mice) received a single IV bolus injection of $^3$H-Taxol (control) or PGA-44-A-19 via a tail vein.

Figure 16:
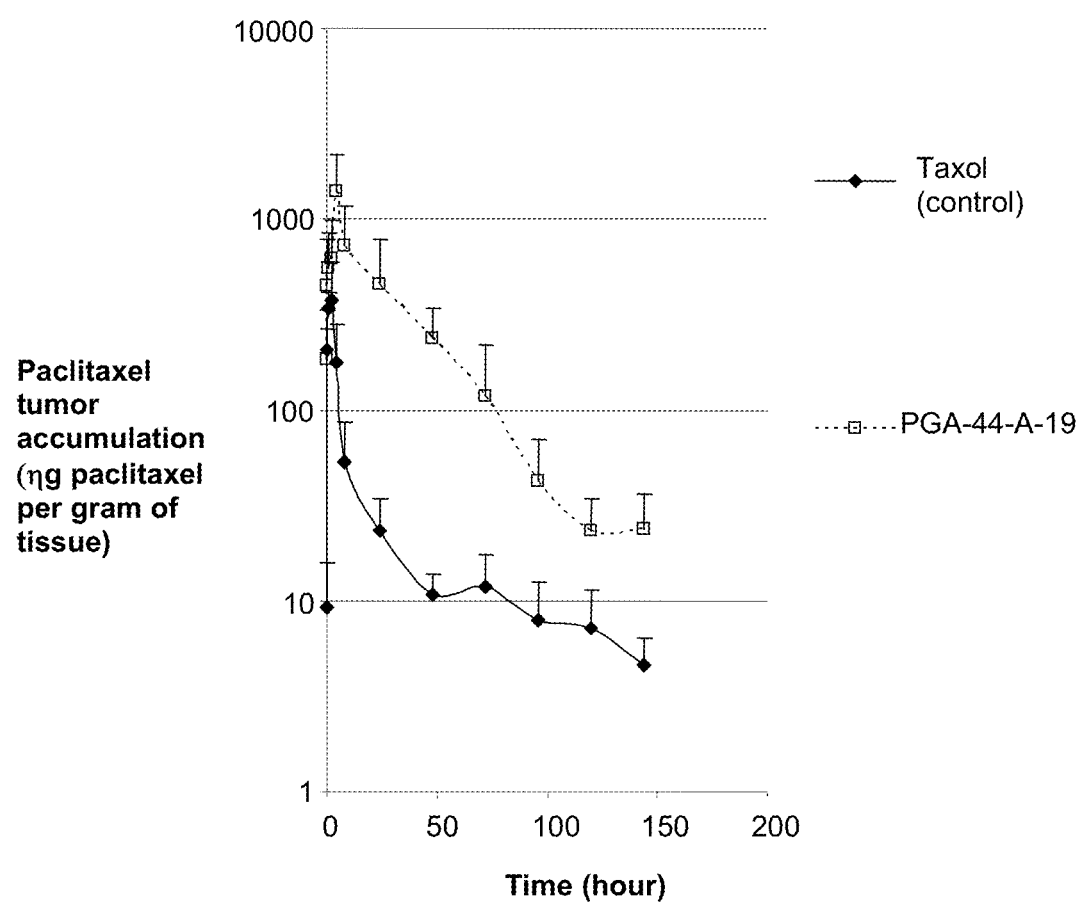
FIG. 16 shows a plot that illustrates the paclitaxel tumor concentrations of PGA-44-A-19 and Taxol on B16F0 melanoma tumors in nude nu/nu mice over time.

PGA-44-A-19 was prepared as in Example 10c, from poly(γ-L-aspartyl-glutamine) with average molecular weight of 39,700 daltons based on the Heleos system with MALS detector, and the weight percentage of paclitaxel in the polymer was 19%. The dose of free $^3$H-Taxol (control) and PGA-44-A-19 was 20 mg paclitaxel equivalents/kg. For each drug, groups of 4 mice were anesthetized at various time points (each unit is in hours): 0 (i.e. as quickly as possible after the IV injection), 0.083, 0.25, 1.0, 2.0, 4.0, 8.0, 48, 72, 96, 120, and 144. Tumors from the two hips and the two shoulders were harvested independently. Thereafter, the mice were sacrificed before recovering from anesthesia. Approximately 80-180 mg of each tumor was placed in a scintillation vial, and the tumor was digested with Soluene (tissue solubilizer) (1 mL). Then, 0.1 mL of digested tissue was transferred into a 10-mL vial, and a liquid scintillation cocktail (5 mL) was added to the vial. The content of paclitaxel was analyzed using a liquid scintillation LS6500 counting system (Beckman) and calculated from the standard curve of each sample. PGA-44-A-19 was compared to the Taxol control. The results are shown in FIG. 16. The paclitaxel tumor accumulation of PGA-44-A-19 remained much higher over a longer period of time. These results indicate that the paclitaxel from PGA-44-A-19 has improved accumulation in tumors compared to Taxol alone.

Example 25

Animals and Tumor Models for In Vivo Efficacy Studies

Nude mice (6-8 weeks old, body weight 21-25 grams, male) were purchased from Charles River Lab (Willington, Mass.). B16-F0-EGFP stable cells were maintained in a cell culture grown in DMEM supplemented with 10% Bovine Serum, 100 U/ml of penicillin and 100 of µg/ml streptomycin. Cells were split 48 hours before inoculation so that they were in a log phase growth upon being harvested. Cells were harvested from the tissue culture using trypsin-EDTA and the number of viable cells was determined by counting in a hemocytometer in the presence of trypan blue. The cells were suspended to a concentration of $5 \times 10^6$ per ml in a DMEM media without serum. The tumor cell suspension was inoculated using a 1 cc insulin syringe at a concentration of $5 \times 10^6$ per ml over each shoulder and each hip by injecting 0.1 ml of tumor cell suspension (4 sites/mouse).

On the day of tumor inoculation, mice were sequentially placed into one of 6 groups and housed 3 mice to a cage with a total number of 12 cages. Each mouse was ear punched while under anesthesia at the time of tumor inoculation so that it could be uniquely identified throughout the experiment. Each cage was labeled with the drug, drug dose administered to the animals it contained, and the number of animals it contained.

Example 25a

Figure 17:
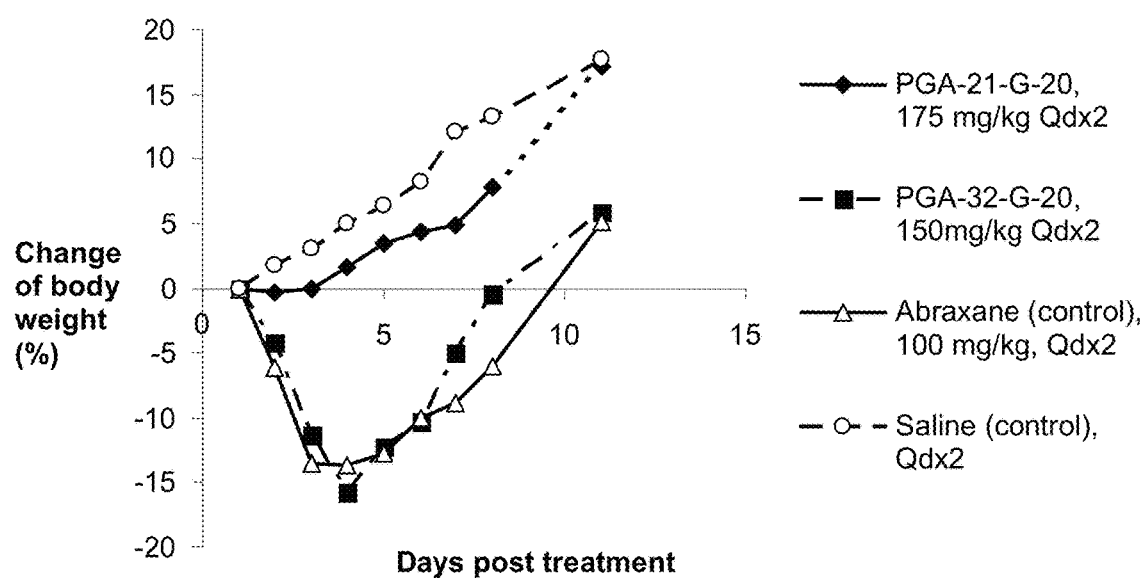
FIG. 17 shows a plot that illustrates the change in body weight (%) upon treatment with PGA-21-G-20, PGA-32-G-20, Abraxane, and saline at their respective maximum tolerance doses on nude nu/nu mice over time.

The weight loss toxicity at the maximum tolerance dose (MTD) of polymers made in accordance with Examples 11a-11c was measured. MTD is defined herein as the dose that produces a maximum 15% body weight loss within 2 weeks. PGA-21-G-20 and PGA-32-G-20 were prepared as disclosed in Examples 11c and 11b, respectively, from starting poly(γ-L-glutamyl-glutamine) polymers with average molecular weight of 19,800 and 37,400 daltons, respectively, based on the Heleos system with MALS detector, and the weight percentage of paclitaxel in each of polymers was 20%. PGA-21-G-20 and PGA-32-G-20 were dissolved in saline at 50 mg per mL. The control anti-cancer drug for this example was Abraxane, which is FDA-approved as an anti-cancer drug. Saline was also used as a negative control with no anti-tumor drug. The actual amount of drug injected was determined from the body weight of each animal. The first dose of drug was given to the mice when the average tumor size of the entire population of mice reached about 15 to about 50 mm$^3$ (tumor size was estimated from the formula ($w^2 \times l$)/2 where "l" is the longest diameter of the tumor and "w" is the diameter perpendicular to the longest diameter measured in millimeters). Mice received 2 doses of drug on the two consecutive days via tail vein injection administered without anesthesia. Stock solutions were prepared fresh on the day of injection. Drug stock solutions were drawn into a 1-cc syringe and injected intravenously. Mice were weighed to the nearest 0.1 g. Nude nu/nu mice were injected with higher dosage amounts of both PGA-21-G-20 at a dose of 175 mg/kg and PGA-32-G-20 at a dose of 150 mg/kg as compared to Abraxane at dose of 100 mg/kg paclitaxel equivalence. The change of body weight (%) upon treatment of each drug was independently observed and recorded over time (days). The results are shown in FIG. 17. PGA-21-G-20 shows little body weight loss at a much higher dosage. PGA-32-G-20 showed a comparable body weight loss to Abraxane at a much higher dosage. These results indicate that preferred polymers of the present invention conjugated with anti-cancer drug are less toxic to mice.

Example 26

In Vivo Efficacy Studies

Figure 18:
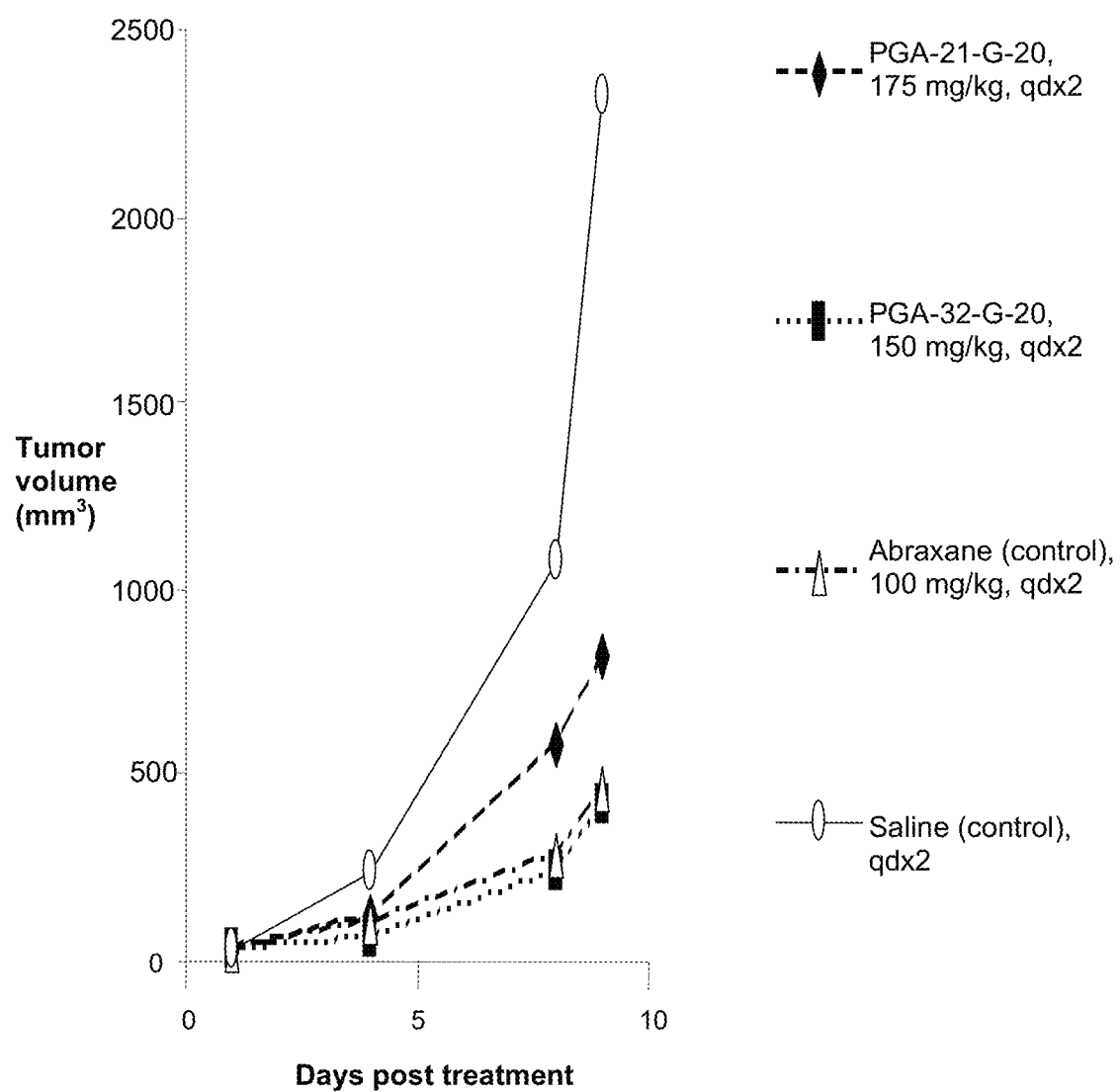
FIG. 18 shows a plot that illustrates the antitumor effect of PGA-21-G-20, PGA-32-G-20, Abraxane, and saline at their respective maximum tolerance doses on B16F0 transformed EGF melanoma tumors in nude nu/nu mice over time.

The antitumor effects of PGA-21-G-20, PGA-32-G-20, and Abraxane, at the maximum tolerance dose (MTD) on B16F0-EGF melanoma tumors in nude nu/nu mice as described in Example 25 over time with saline as a negative control were measured. PGA-21-G-20 and PGA-32-G-20 were dissolved in saline at 50 mg per mL. The control anti-cancer drug for this example was Abraxane, which is FDA-approved as an anti-cancer drug. Saline was used as another control with no anti-tumor drug. The actual amount of drug injected was determined from the body weight of each animal. The first dose of drug was given to the mice when the average tumor size of the entire population of mice in the study reached 15 to 50 mm³. Mice received 2 doses of drug on the two consecutive days via tail vein intravenously administered without anesthesia. Stock solutions were prepared fresh on the day of injection. The drug stock solutions were drawn into a 1-cc syringe and injected intravenously. The tumor size was measured to the nearest 0.1 mm. Nude nu/nu mice were injected with higher dosage amounts of both PGA-21-G-20 at a dose of 175 mg/kg and PGA-32-G-20 at a dose of 150 mg/kg as compared to the Abraxane control at dose of 100 mg/kg paclitaxel equivalence. The change of tumor volume upon treatment of each drug was independently observed and recorded over time (days). The results are shown in FIG. 18. Both PGA-21-G-20 and PGA-32-G-20 significantly inhibited the tumor growth. These results indicate that preferred polymers of the present invention conjugated with anti-cancer drug are effective anti-cancer agents.

Example 27

Figure 19:
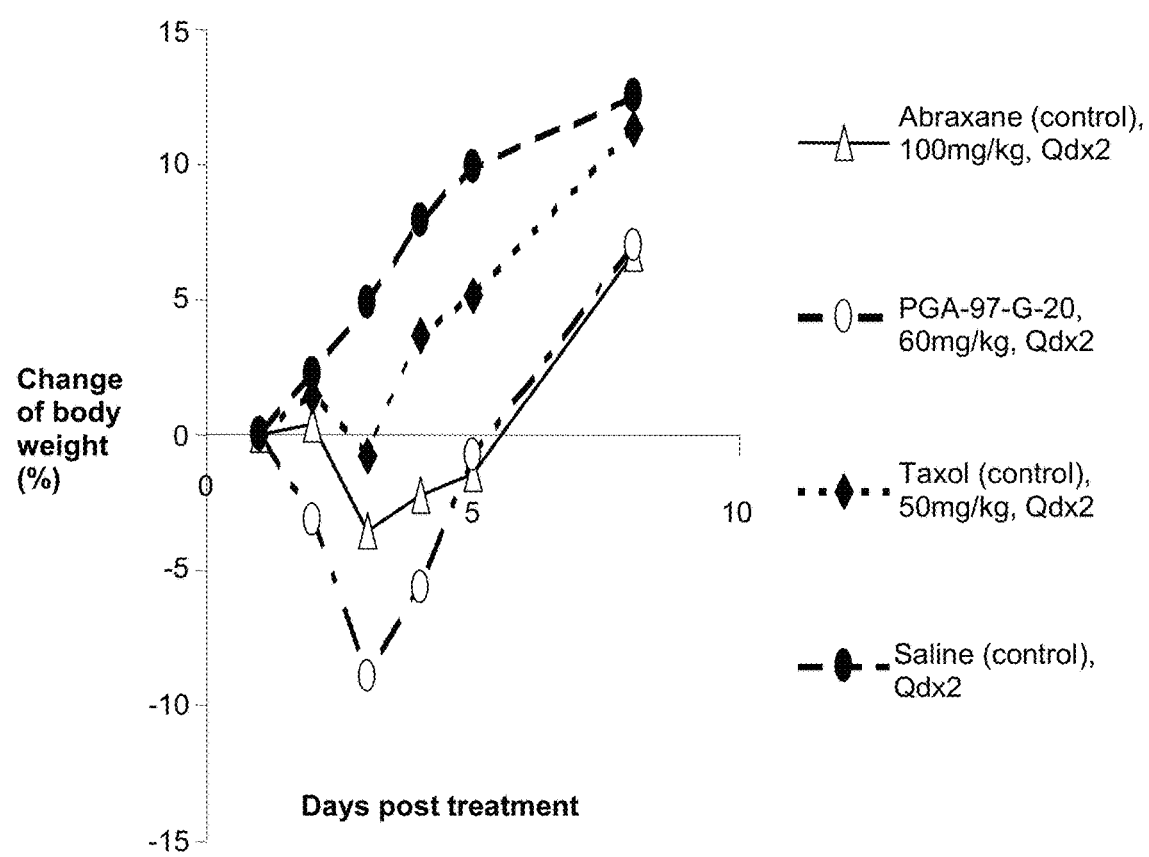
FIG. 19 shows a plot that illustrates the change in body weight (%) upon treatment with PGA-97-G-20, Taxol, Abraxane, and saline at their respective maximum tolerance doses on nude nu/nu mice over time.

The weight loss toxicity at the MTD was measured of a polymer made in accordance with Example 11. PGA-97-G-20 was prepared according to the procedure described in Example 11. The starting material was poly(γ-L-glutamyl-glutamine) with an average molecular weight of 110,800 daltons based on our the Heleos system with MALS detector. The weight percentage of paclitaxel in the polymer was 20%. PGA-97-G-20 was dissolved in saline at 50 mg per mL. The control anti-cancer drugs for this example were Taxol and Abraxane, which are FDA-approved as anti-cancer drugs. Saline was used as a negative control with no anti-tumor drug. The actual amount of drug injected was determined from the body weight of each animal. The first dose of drug was administered when the average tumor size of the entire population of mice in the study reached 15 to 50 mm³. The mice received 2 doses of drug in the two consecutive days via tail vein injection without anesthesia. Stock solutions were prepared fresh on the day of injection. Drug stock solutions were drawn into a 1-cc syringe and injected intravenously. The mice were weighed to the nearest 0.1 g. Nude nu/nu mice were injected with higher dosage amounts of PGA-97-G-20 (60 mg/kg) as compared to Abraxane (100 mg/kg) and Taxol (50 mg/kg) at their paclitaxel equivalence. The change of body weight (%) upon treatment of each drug was independently observed and recorded over time (days). The results are shown in FIG. 19. As shown in FIG. 19, PGA-97-G-20 showed a comparable body weight loss to the control at a much higher dosage. These results indicate that preferred polymers of the present invention conjugated with anti-cancer drug have comparable toxicity to a clinically-approved drug.

Example 28

In Vivo Efficacy Studies

Figure 20:
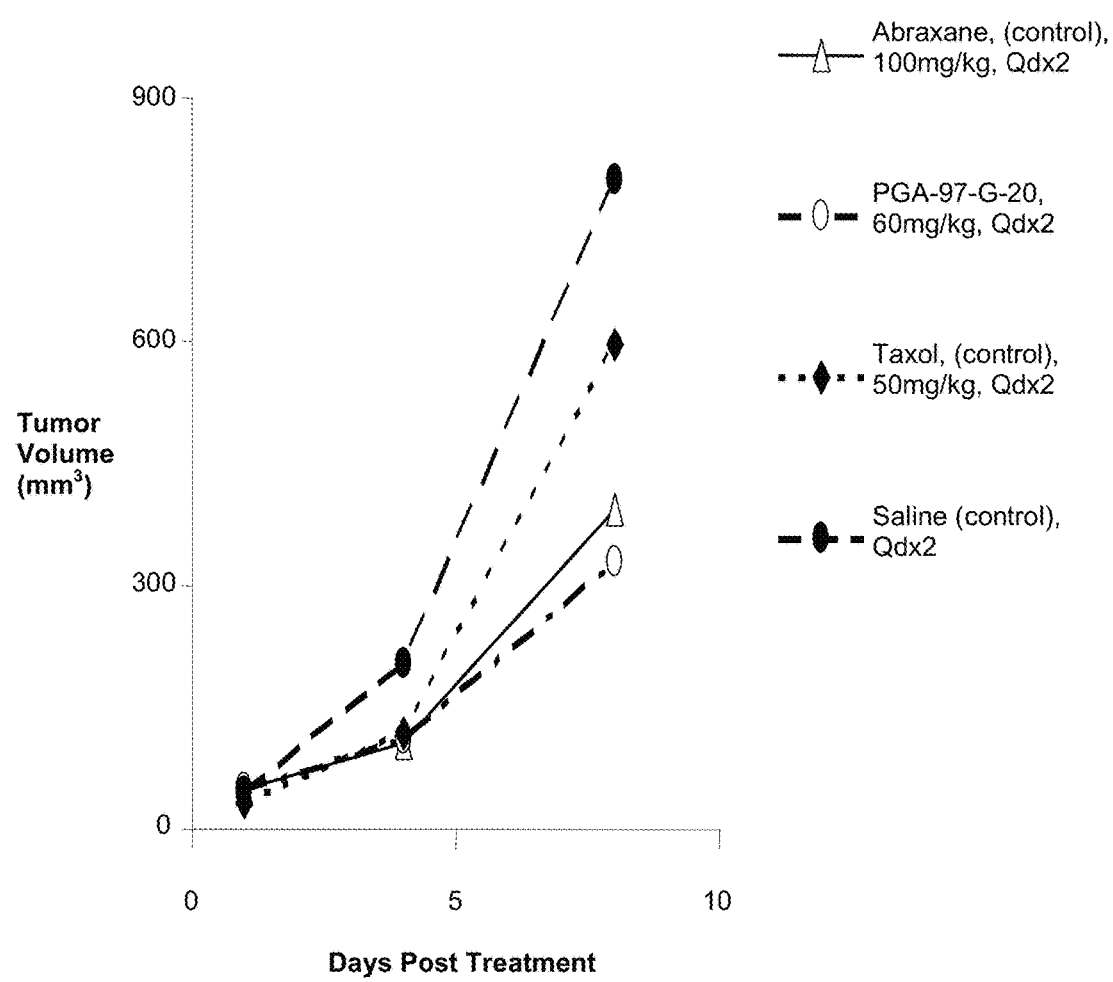
FIG. 20 shows a plot that illustrates the antitumor effect of PGA-97-G-20, Taxol, Abraxane, and saline at their respective maximum tolerance doses on B16F0 transformed EGF melanoma tumors in nude nu/nu mice over time.

The antitumor effects of PGA-97-G-20, Taxol, and Abraxane, at the maximum tolerance dose (MTD) on B16F0-EGF melanoma tumors in nude nu/nu mice over time with saline as a negative control were measured. PGA-97-G-20 was dissolved in saline at 50 mg per mL. The control anti-cancer drugs for this example were Taxol and Abraxane, which are FDA-approved as an anti-cancer drug. Saline was used as a negative control with no anti-tumor drug. The actual amount of drug injected was determined from the body weight of each animal. The first dose of drug was administered when the average tumor size of the entire population of mice in the study reached 15 to 50 mm³. The mice received 2 doses of drug via IV tail vein injection without anesthesia on the next day. Stock solutions were prepared fresh on the day of injection. The drug stock solutions were drawn into a 1-cc syringe and injected intravenously. Tumor size was measured to the nearest 0.1 mm. Nude nu/nu mice were injected with higher dosage amounts of PGA-97-G-20 at dose of 60 mg/kg as compared to Abraxane at dose of 100 mg/kg and Taxol 50 mg/kg at their paclitaxel equivalence. The change of tumor volume upon treatment of each drug was independently observed and recorded over time (days). The results are shown in FIG. 20. As shown in FIG. 20, PGA-97-G-20 had a significant effect on the tumor growth and better performance than both Taxol and Abraxane. These results indicate that preferred polymers of the present invention conjugated with anti-cancer drug are effective anti-cancer agents.

Example 29

The weight loss toxicity at maximum tolerance dose of polymer conjugates containing paclitaxel to polyglutamic acid conjugated with paclitaxel was measured. PGA-32-G-20 was prepared in accordance with the procedure from Example 11b. The starting material was poly(γ-L-glutamyl-glutamine) polymer with average molecular weight of 37,400 daltons based on the Heleos system with MALS detector, and the weight percentage of paclitaxel in each of polymers was 20%. PGA-32-G-20 was compared to a control of polyglutamic acid with a molecular weight of 19,450 daltons (based on the Heleos system with MALS) conjugated to paclitaxel such that the weight percentage of paclitaxel in the polymer is 20% (PGA(32k)-PTX-20).

Figure 21:
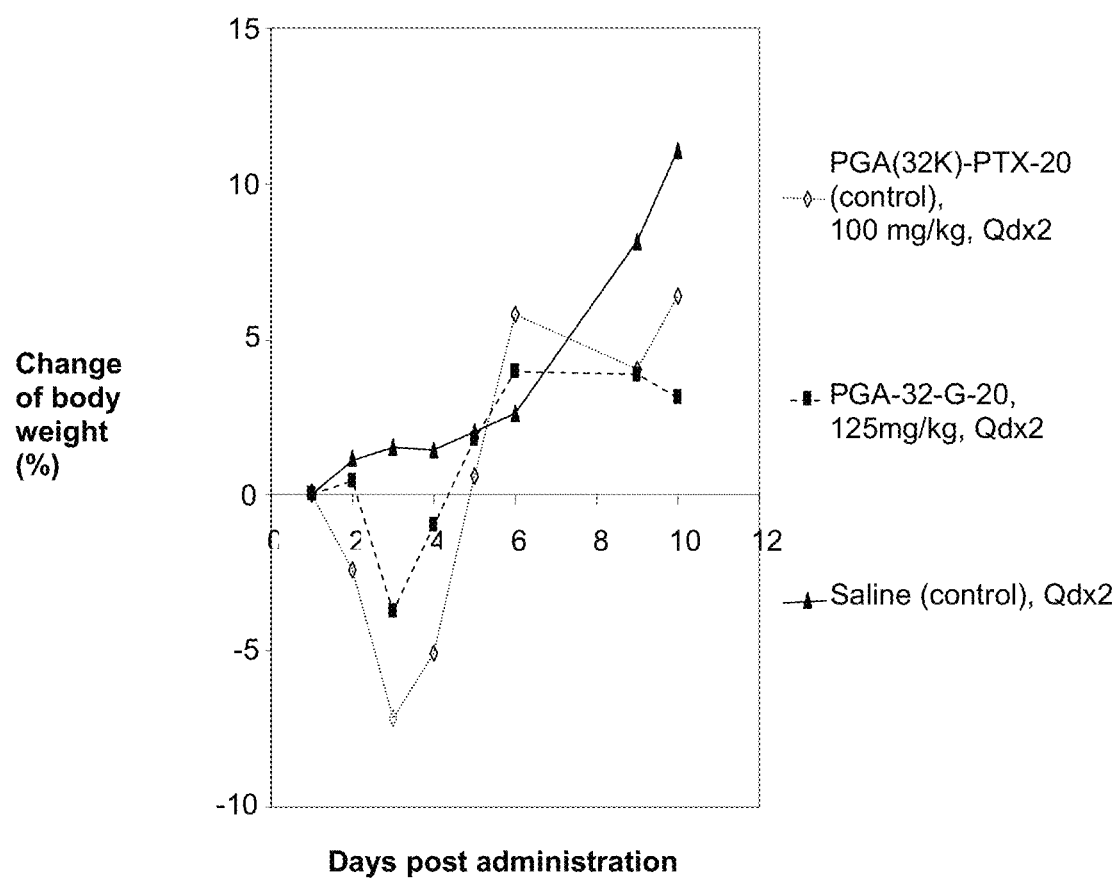
FIG. 21 shows a plot that illustrates the change of body weight (%) upon treatment with PGA-32-G-20, PGA(32k)-PTX-20, and saline at their respective maximum tolerance doses on nude nu/nu mice over time.

Saline was used as a base control with no anti-tumor drug. Both PGA-32-G-20 and PGA(32k)-PTX-20 were dissolved in saline at 50 mg per mL. Saline was used as a control with no anti-tumor drug. The actual amount of drug injected was determined from the body weight of each animal. The first dose of drug was administered when the average tumor size of the entire population of mice in the study reached 15 to 50 mm$^3$. The mice received 2 doses of drug via IV tail vein injection administered without anesthesia on the next day. Stock solutions were prepared fresh on the day of injection. The drug stock solutions were drawn into a 1-cc syringe and injected intravenously. The mice were weighed to the nearest 0.1 g. Nude nu/nu mice were injected with higher dosage amounts of PGA-32-G-20 at a dose of 125 mg/kg as compared to PGA(32k)-PTX-20 at a dose of 100 mg/kg paclitaxel equivalence. The change of body weight (%) upon treatment of each drug was independently observed and recorded over time (days). The results are shown in FIG. 21. PGA-32-G-20 showed a comparable body weight loss to the control at a much higher dosage. These results indicate that preferred polymers of the present invention conjugated with anti-cancer drug have comparable toxicity to an investigational drug.

Example 30

In Vivo Efficacy Studies

Figure 22:
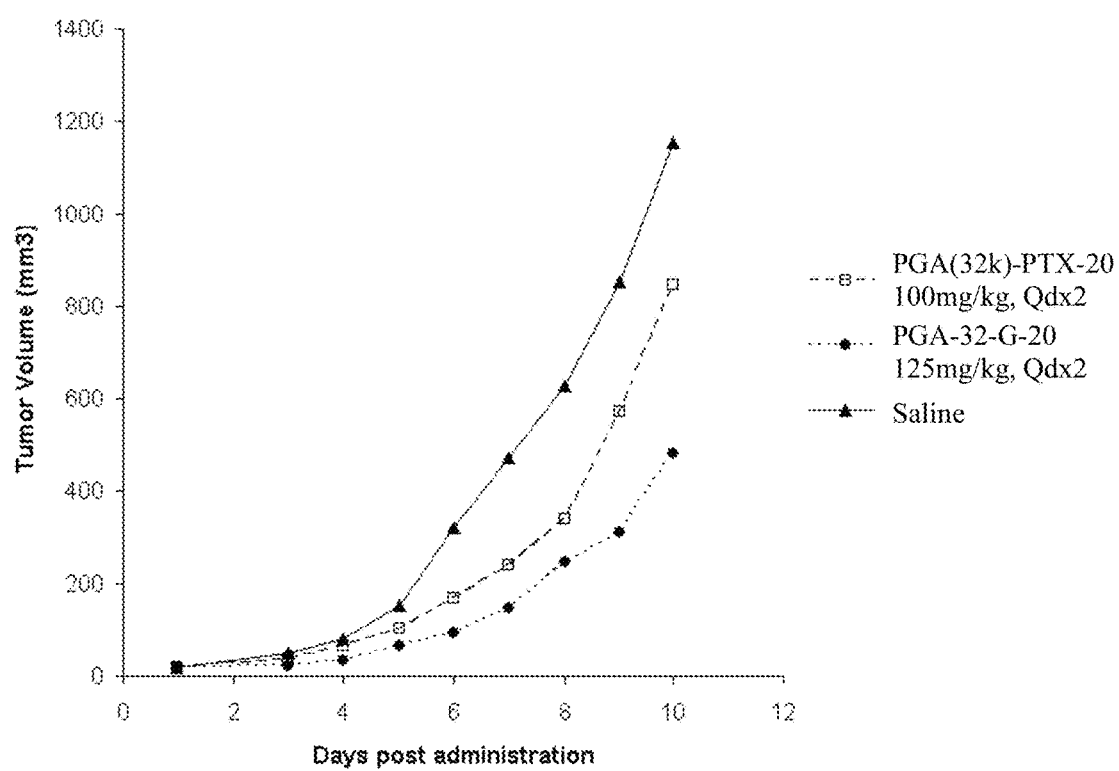
FIG. 22 shows a plot that illustrates antitumor effect of PGA-32-G-20, PGA(32k)-PTX-20, and saline at their respective maximum tolerance doses on B16F0 transformed EGF melanoma tumors in nude nu/nu mice over time.

The antitumor effects of PGA-32-G-20 and PGA(32k)-PTX-20, at the maximum tolerance dose (MTD) on B16F0-EGF melanoma tumors in nude nu/nu mice over time with saline as a negative control were measured. Both PGA-32-G-20 and PGA(32k)-PTX-20 were dissolved in saline at 50 mg per mL. The actual amount of drug injected was determined from the body weight of each animal. The first dose of drug was administered when the average tumor size of the entire population of mice in the study reached 15 to 50 mm$^3$. The mice received 2 doses of drug via IV tail vein injection administered without anesthesia on the next day. Stock solutions were prepared fresh on the day of injection. The drug stock solutions were drawn into a 1-cc syringe and injected intravenously. The mice were weighed to the nearest 0.1 g. Nude nu/nu mice were injected with higher dosage amounts of PGA-32-G-20 at a dose of 125 mg/kg as compared to PGA(32k)-PTX-20 at a dose of 100 mg/kg paclitaxel equivalence. Tumor size was measured to the nearest 0.1 mm. The change of tumor volume upon treatment of each drug was independently observed and recorded over time (days). The results are shown in FIG. 22. PGA-32-G-20 had a significant effect on the tumor growth and better performance than PGA(32k)-PTX-20. These results indicate that preferred polymers of the present invention conjugated with anti-cancer drug are effective anti-cancer agents.

Example 31

Figure 23:
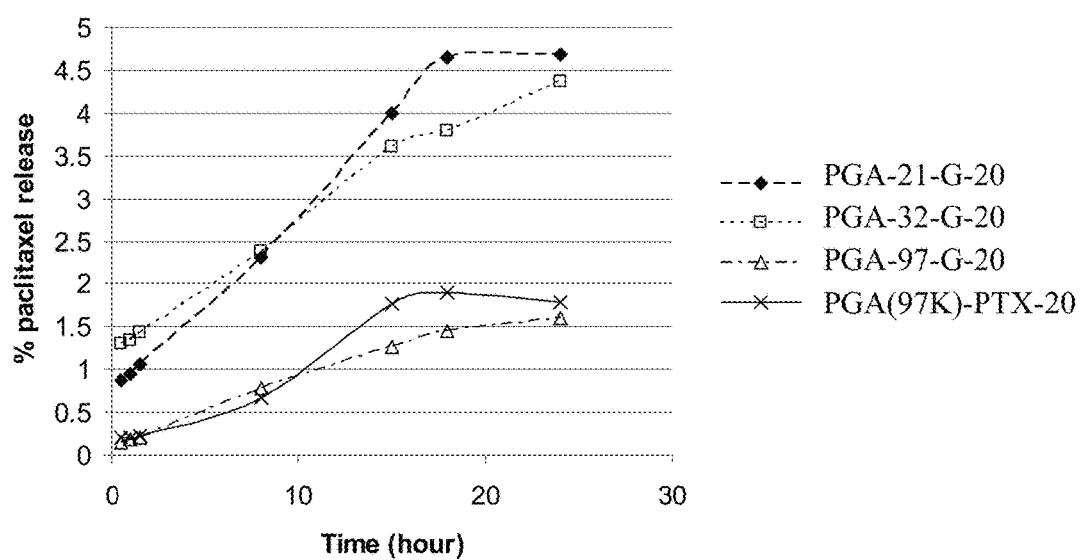
FIG. 23 shows a plot that illustrates paclitaxel release over time at a concentration of 2 mg per mL of polymer-paclitaxel conjugates in phosphate buffers.

Polymer conjugates were tested to determine the rate at which paclitaxel is released in relation to selecting different molecular weights of the polymers. PGA-21-G-20, PGA-32-G-20, PGA-97-G-20, and a control of PGA(97k)-PTX-20 were placed in phosphate buffers at a concentration of 2 mg per mL and the rate of release was measured. The solution of polymer-paclitaxel conjugates was incubated at 37° C. An aliquot of 50 μl was taken out at different time points and was frozen. All aliquots were then analyzed by LC-MS. Integration area of released drug peak on the HPLC profile was measured. The amount of released paclitaxel was calculated from standard curve. The results are illustrated in FIG. 23, and show that as the molecular weight of the polymer conjugates increased, the percentage of paclitaxel released decreased. These results indicate that the rate of release of the paclitaxel can be controlled by selecting different molecular weights for the polymer.

Example 32

Animals and Tumor Models for Pharmacokinetic Studies

Nude mice (6-7 weeks old, body weight 25-30 grams, female) were purchased from Charles River Lab (Willington, Mass.). B16F0 cell lines were purchased from ATCC (CRL-6322, ATCC American Type Culture Collection, Rockville, Md.). The B16F0 cells were cultured in DMEM supplemented with 10% Fetal bovine serum, 2 μM Glutamine, 1 mM non-essential amino acids, 1 mM sodium pyruvate, 100 U/ml penicillin and 100 ug/ml streptomycin. The B16F0 cells harvested from tissue culture were counted and re-suspended to a concentration of 5×10$^6$ per mL. Using a TB syringe, 0.4 mL (a total of 2×10$^6$ cells) was administered via subcutaneous injection into each mouse. Four tumors were inoculated per animal at the right shoulder, the left shoulder, the right hip, and left hip.

Example 32a

Various drug-conjugated polymers were tested against a control of Taxol to determine the paclitaxel concentration in plasma over time. At the point when the mean tumor volume for the entire population of mice from Example 32 had reached 200-300 mm$^3$ (6-8 mm diameter), each tumor bearing animal received a single IV bolus injection of $^3$H-Taxol (control), PGA-21-A-19, PGA-32-A-19, PGA-97-A-24 via a tail vein.

PGA-21-G-19 was prepared from the reactant polymer poly-(γ-L-glutamyl-glutamine) where the molecular weight was 19,800 daltons, and the weight percentage of paclitaxel in the polymer was 19%. PGA-32-G-19 was prepared from the reactant polymer poly-(γ-L-glutamyl-glutamine) where the molecular weight was 37,400 daltons, and the weight percentage of paclitaxel in the polymer was 19%. PGA-97-G-24 was prepared from the reactant polymer poly-(γ-L-glutamyl-glutamine) where the molecular weight was 110,800 daltons, and the weight percentage of paclitaxel in the polymer was 24%.

Figure 24:
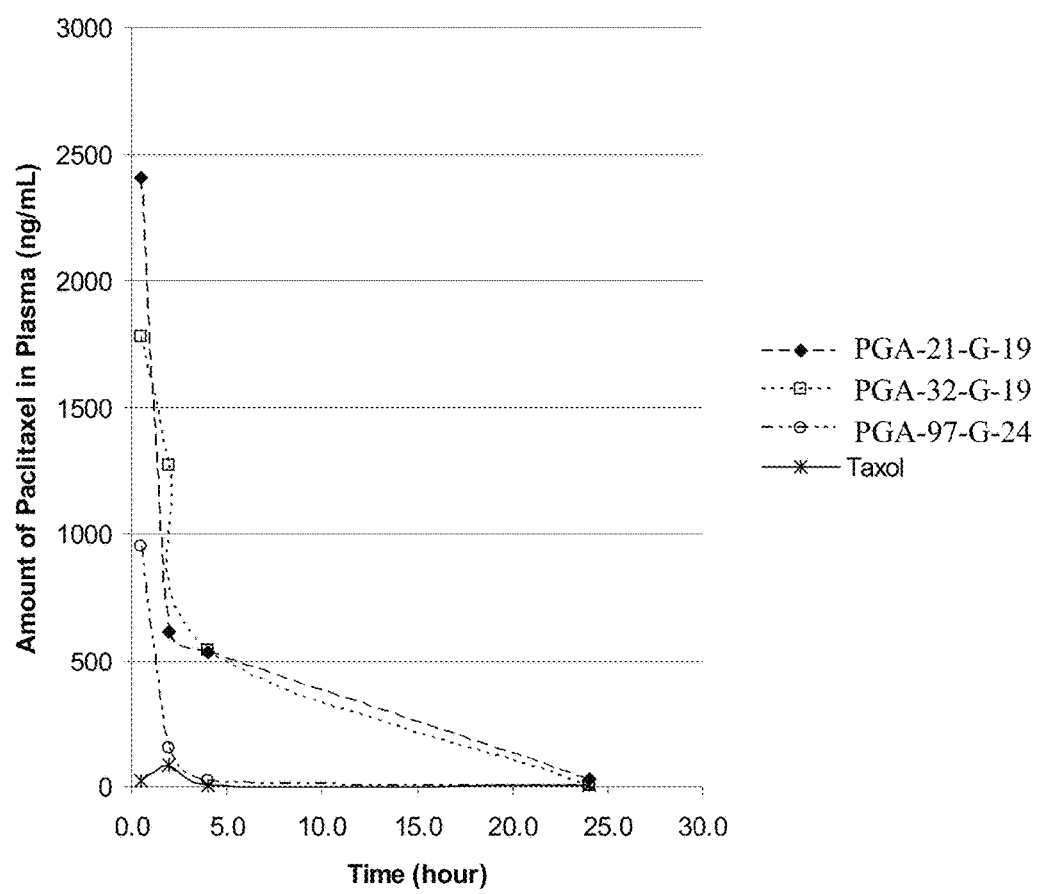
FIG. 24 shows a plot that illustrates paclitaxel concentration in plasma of PGA-21-G-19, PGA-32-G-19, PGA-97-G-24, and Taxol over time.

The dose of free $^3$H-Taxol (control), PGA-21-A-19, PGA-32-A-19, and PGA-97-A-24 was 20 mg paclitaxel equivalents/kg. For each drug, groups of 4 mice were anesthetized at various time points (each unit is in hours): 1.0, 2.0, 4.0, and 24. A collection of 0.5 ml of blood obtained by cardiac or retro-orbital puncture was made into heparinized tubes. Thereafter, mice were sacrificed before recovering from anesthesia. The blood samples of each mouse were centrifuged at 11,000 rpm. The supernatant plasma (0.2-0.3 mL) from the blood samples were collected and transferred into a new vial. 0.1 mL of the plasma of each sample was separately transferred into a new 10-mL vial, and a liquid scintillation solution (5 mL) was added to the vial. The content of paclitaxel was analyzed using a liquid scintillation LS6500 counting system (Beckman) and calculated from the standard curve of each sample. The results are shown in FIG. 24. These results show that the paclitaxel drug in preferred polymer conjugates of the present invention have a longer duration in plasma as compared to Taxol.

Example 33

Various drug-conjugated polymers were tested against a control of Taxol to determine the paclitaxel concentration present in a tumor over time. At the point when the mean tumor volume for the entire population of mice from Example 32 had reached 200-300 mm$^3$ (6-8 mm diameter), each tumor bearing animal received a single IV bolus injection of $^3$H-Taxol (control), PGA-21-A-19, PGA-32-A-19, PGA-97-A-24 via a tail vein.

PGA-21-G-19 was prepared from the reactant polymer poly-(γ-L-glutamyl-glutamine) where the molecular weight was 19,800 daltons, and the weight percentage of paclitaxel in the polymer was 19%. PGA-32-G-19 was prepared from the reactant polymer poly-(γ-L-glutamyl-glutamine) where the molecular weight was 37,400 daltons, and the weight percentage of paclitaxel in the polymer was 19%. PGA-97-G-24 was prepared from the reactant polymer poly-(γ-L-glutamyl-glutamine) where the molecular weight was 110,800 daltons, and the weight percentage of paclitaxel in the polymer was 24%.

Figure 25:
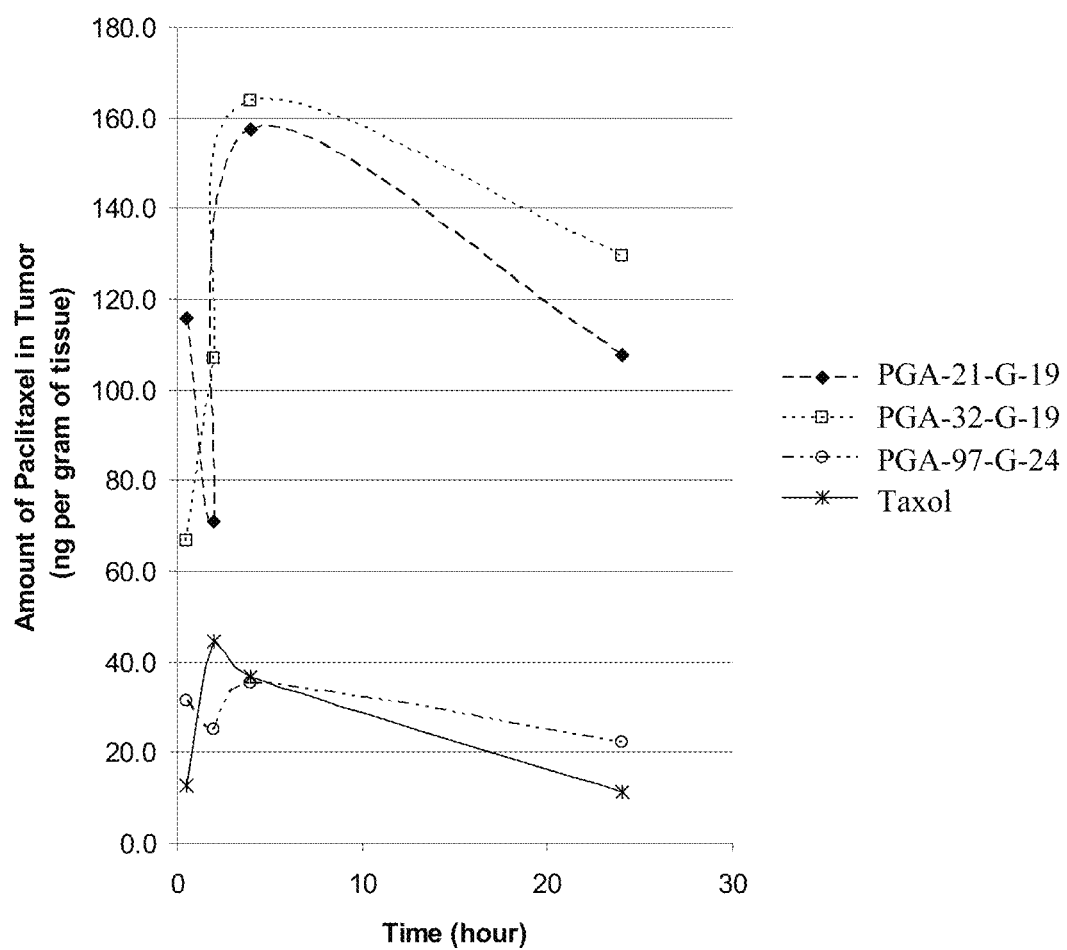
FIG. 25 shows a plot that illustrates paclitaxel concentration in a tumor of PGA-21-G-19, PGA-32-G-19, PGA-97-G-24, and Taxol over time.

The dose of free $^3$H-Taxol (control), PGA-21-A-19, PGA-32-A-19, and PGA-97-A-24 was 20 mg paclitaxel equivalents/kg. For each drug, groups of 4 mice were anesthetized at various time points (each unit is in hours): 1.0, 2.0, 4.0, and 24. Tumors from the two hips and the two shoulders were harvested independently. Thereafter, the mice were sacrificed before recovering from anesthesia. Approximately 80-180 mg of each tumor was placed in a scintillation vial, and the tumor was digested with Soluene (tissue solubilizer) (1 mL). Then, 0.1 mL of digested tissue was transferred into a 10-mL vial, and a liquid scintillation cocktail (5 mL) was added to the vial. The content of paclitaxel was analyzed using a liquid scintillation LS6500 counting system (Beckman) and calculated from the standard curve of each sample. The results are shown in FIG. 25. These results show that the paclitaxel drug in preferred polymer conjugates of the present invention are more concentrated in a tumor over the course of time as compared to Taxol.

Example 34

Animals and Tumor Models

Nude mice (6-7 week old, body weight 25-30 g, male) were purchased from Charles River Lab (Willington, Mass.). B16 cell line was purchased from ATCC (CRL-6322, ATCC American Type Culture Collection, Rockville, Md.). The B16 cells were cultured in RMPI 1640 supplemented with 10% Fetal bovine serum, 2 µM Glutamine, 1 mM non-essential amino acids, 1 mM sodium pyruvate, 100 U/ml penicillin and 100 ug/ml streptomycin. The B16 cells harvested from tissue culture were counted and re-suspended to a concentration of 5×10$^6$ per mL. Using a TB syringe, 0.2 mL (a total of 1×10$^6$ cells) was administered via subcutaneous injection into each mouse. One tumor was inoculated per animal at the right hip. The site of tumor inoculation was shaved prior to inoculation to make it easier to measure the tumor as it grows.

Example 35

Magnetic Resonance Imaging for Tumor Accumulation

Images of mice were acquired on a GE 3T MR scanner using a knee coil pre- and post-contrast. The following imaging parameters were TE: minful, TR=250 ms, FOV: 8 and 24 slices/slab, and 1.0 mm coronal slice thickness. PGA-97-A-DTPA-Gd(III) was prepared as in examples 7-8, from poly(γ-L-aspartyl-glutamine) with average molecular weight of 99,400 daltons based on the Heleos system with MALS detector. The control material for this Example was Omniscan-Gd(III)-(DTPA-BMA (0.1 mmol Gd(III)/kg).

Figure 26:
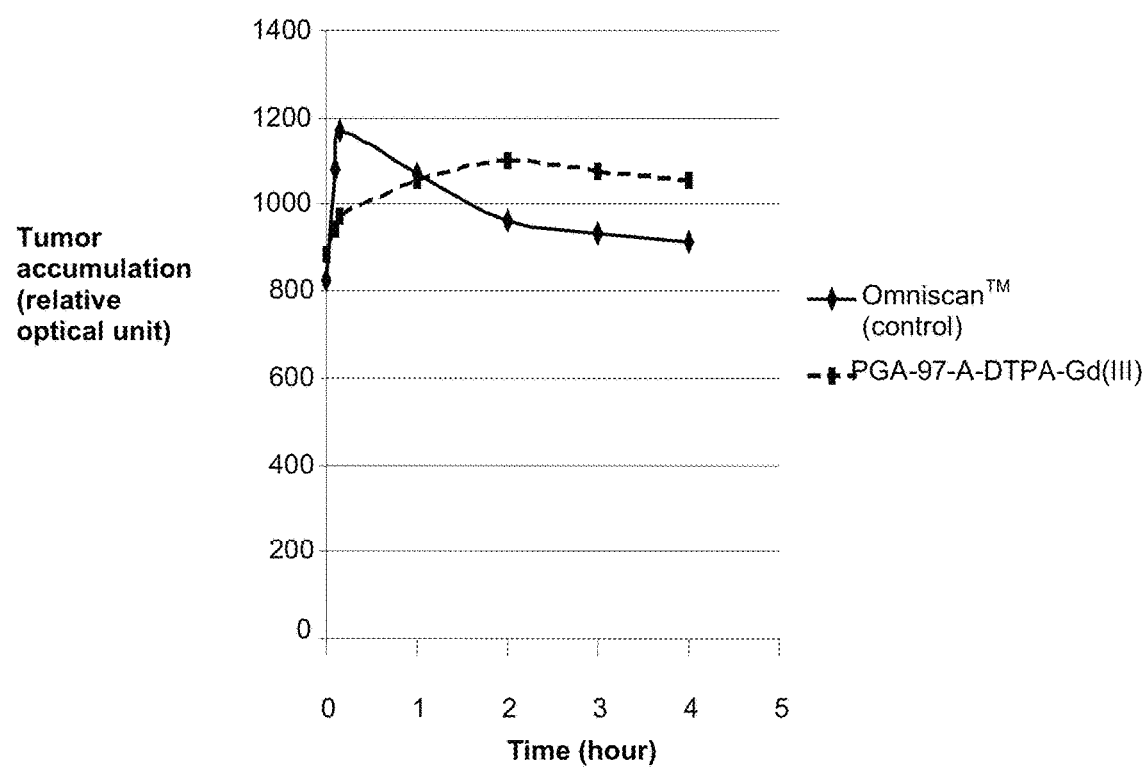
FIG. 26 shows a plot that illustrates the tumor accumulation effect of PGA-97-A-DTPA-Gd(III) and Omniscan™ (gadodimide) on B16F0 melanoma tumors in nude nu/nu mice over time.

The dose of injection of PGA-97-A-DTPA-Gd(III) was 0.1 mmol Gd(III)/kg. The dose of injection of Omniscan™ was 0.1 mmol Gd(III)/kg. The two compounds were injected via a tail vein into anesthetized mice and images were acquired at pre-injection and at 6 minutes to 4 hours post-injection of the contrast agents. The results of the MRI are shown in FIG. 26. As shown by FIG. 26, the amount of PGA-97-A-DTPA-Gd(III) chelate that accumulated in the tumor tissue is greater than the small molecule Omniscan-Gd(III). These results indicate the PGA-97-A-DTPA-Gd(III) chelates have increased specificity and retention.

Example 36

Studies of Nano-Particle Formation

A various solution (filtered through 0.2 µm filter) was added onto poly-(g-aspartyl-glutamine) where the molecular weight was 99,400 daltons) at 1 mg/mL excepted where it is indicated. All the solutions were homogenously dissolved. The particle size, polydispersity and baseline index were measured by light scattering ZetaIPals (Brookhaven Instrument Corporation). The results were summarized in Table 2. MilliQ water means water which was filtered through transfer system with 0.2 µm filter.

TABLE 2

Polyglutamate-Aspartic acid Forms Nano-Particles

|  | Effective diameter | Polydispersity | Baseline Index |
| --- | --- | --- | --- |
| MilliQ water | 244.8 nm | 0.264 | 9.6 |
| MilliQ water (0.1 mg/mL) | 198.0 nm | 0.176 | 8.6 |
| MilliQ water (0.1M NaNO$_3$) | 169.4 nm | 0.336 | 10.0 |
| PBS (pH 7.4) | 138.8 nm | 0.345 | 7.8 |
| PBS (pH 5.0) | 141.0 nm | 0.325 | 9.9 |

Example 37

Formation of Nanoparticles of PGA-97-A-10.

PGA-97-A-10 was dissolved in deionized water at various concentrations. The particle size, polydispersity, and baseline index were measured by light scattering (ZetaIPals, Brookhaven Instruments Corporation). The results are shown in the following Table 3.

TABLE 3

Nano-Particle Formation of PGA-97-A-10 in Deionized Water

| Conc. (µg/mL) | Size (nm) | Polydispersity | Baseline Index |
| --- | --- | --- | --- |
| 722 | 438.9 | 0.133 | 9.7 |
| 289 | 379.0 | 0.169 | 8.8 |
| 100 | 357.5 | 0.226 | 9.1 |
| 50 | 309.4 | 0.215 | 9.5 |
| 10 | 209.6 | 0.220 | 9.3 |
| 5 | 194.9 | 0.208 | 8.1 |
| 1 | 178.0 | 0.172 | 7.4 |
| 0.5 | N/A | 0.122 | 0 |

Example 38

Figure 27:
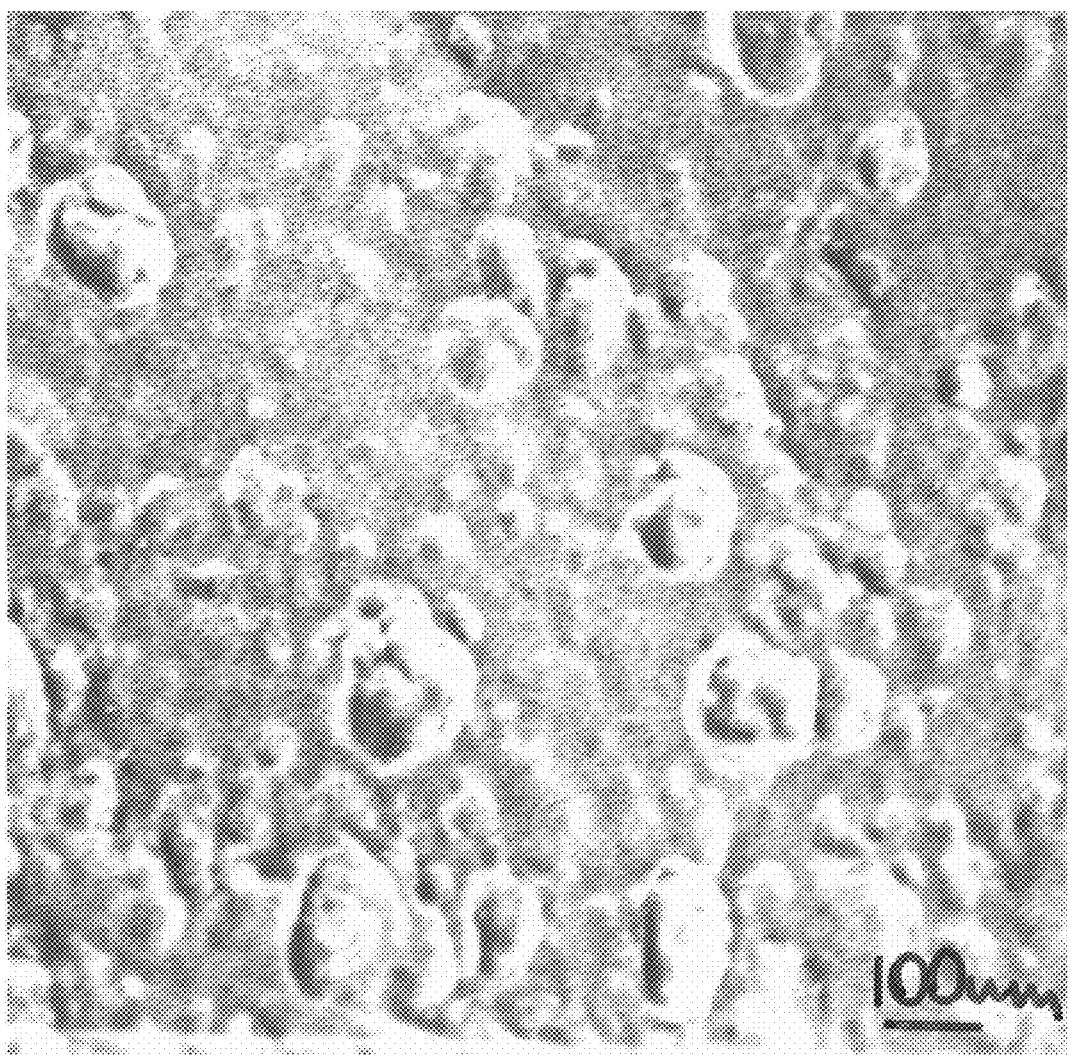
FIG. 27 illustrates a copy of a photograph of the freeze-fractured electron microscopic image of PGA-44-A-20.

A freeze fracture electron microscopic image of drug-conjugated polymer was taken by Nano Analytical Laboratory (San Francisco, Calif.). The polymer was PGA-44-A-20 which was prepared from poly-(g-L-aspartyl-glutamine)

where the molecular weight was 39,700 daltons, and the weight percentage of paclitaxel in the polymer was 20%. It was made into a concentration of 1 mg/mL in saline after sonication (~5 min). After that, it was wrapped in parafilm, and sent to the company right away (overall about one day in transit. Upon arrival, it was stored at 4 C. The polymer was then placed in an aqueous saline solution to determine if nanoparticles would form. A reproduction of the electron microscopic image is shown in FIG. 27. As can be seen in the image, nanoparticles of a preferred drug-conjugated polymer of the present invention formed when the polymer conjugate was placed in an aqueous solution.

Example 39

Figure 28:
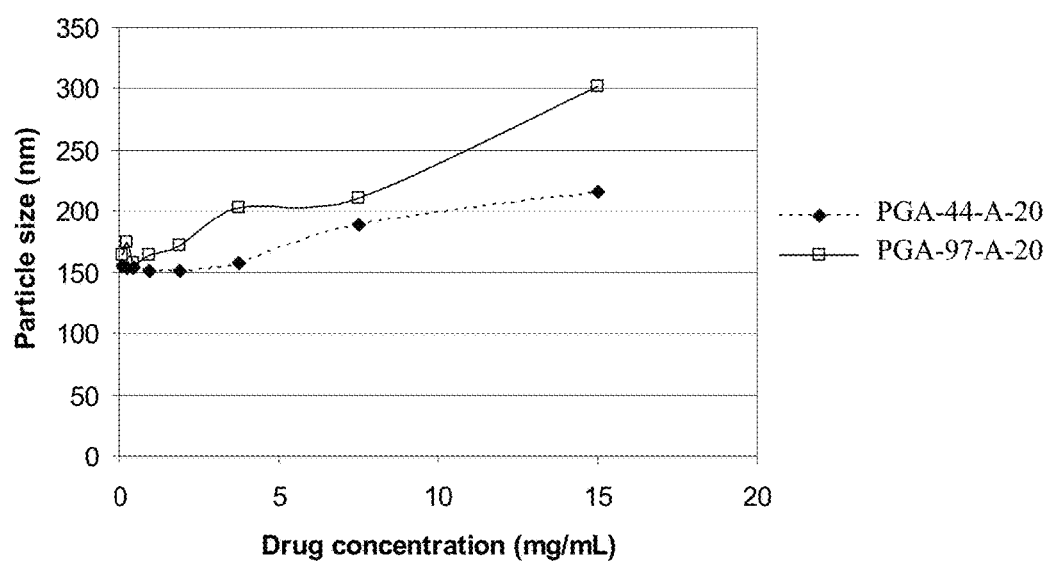
FIG. 28 shows a plot that illustrates static light scattering (particle size) versus concentration of PGA-44-A-20 and PGA-97-A-20.

Particles of the drug-conjugated polymers were tested to determine stability at various drug concentrations. PGA-44-A-20 and PGA-97-A-20 were formed into particles at various drug concentrations and the particle sizes were measured. The results are shown in FIG. 28. The particles remained in the nanoparticle size range and were stable even with increased drug concentration. These results indicate that stable nanoparticles can be formed over a broad range of drug concentration.

Example 40

Figure 29:
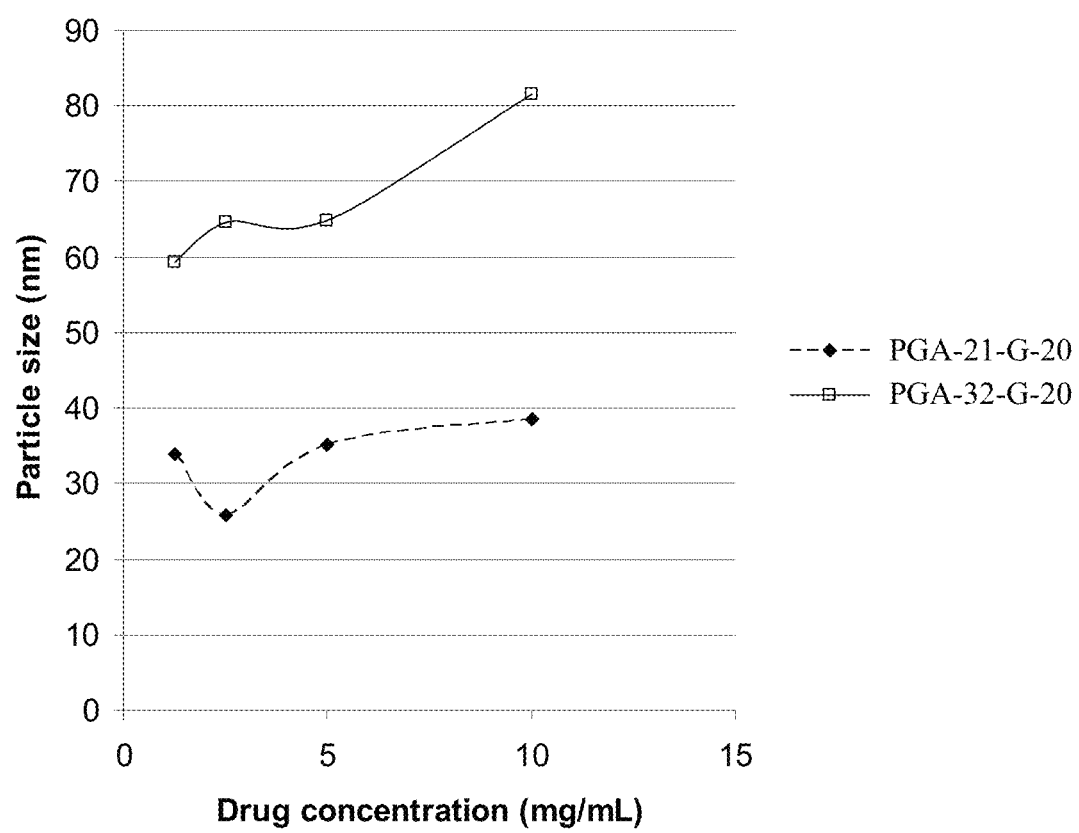
FIG. 29 shows a plot that illustrates static light scattering (particle size) versus concentration of PGA-21-G-20 and PGA-32-G-20.

Particles of the drug-conjugated polymers were tested to determine stability at various drug concentrations. PGA-21-G-20 and PGA-32-G-20 were formed into particles at various drug concentrations and the particle sizes were measured. The results are shown in FIG. 29. The particles remained in the nanoparticle size range and were stable even with increased drug concentration. These results further indicate that stable nanoparticles can be formed over a broad range of drug concentration.

It will be understood by those of skill in the art that numerous and various modifications can be made without departing from the spirit of the present invention. Therefore, it should be clearly understood that the forms of the present invention are illustrative only and not intended to limit the scope of the present invention.

What is claimed is:

1. A pharmaceutical composition comprising particles of an insoluble polymer conjugate dispersed in an aqueous solution, said insoluble polymer conjugate comprising a recurring unit of the formula (I) and a recurring unit of the formula (II):

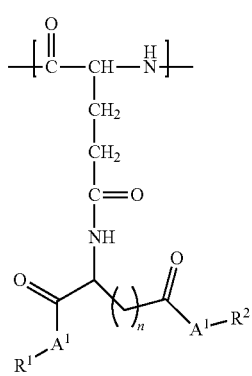

(I)

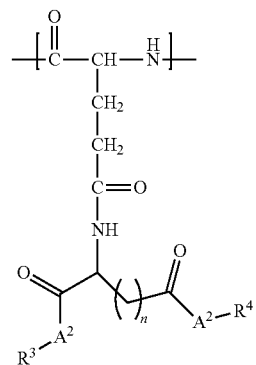

(II)

wherein:
each n is independently 1 or 2;
each $A^1$ is oxygen or $NR^5$;
each $A^2$ is oxygen;
$R^1$ and $R^2$ are each independently selected from the group consisting of $C_{1-10}$ alkyl, $C_{6-20}$ aryl, ammonium, alkali metal, a polydentate ligand, a polydentate ligand precursor with protected oxygen atoms, and a compound that comprises an agent;
wherein the agent is selected from the group consisting of an anticancer drug, a targeting agent, an optical imaging agent, and a magnetic resonance imaging agent;
wherein at least one of $R^1$ and $R^2$ is a group that comprises an agent;
$R^3$ and $R^4$ are each independently selected from the group consisting of hydrogen, ammonium, and an alkali metal;
wherein the polymer conjugate comprises an amount of the agent in the range of about 1 to about 50% (weight/weight) based on the mass ratio of the agent to the polymer conjugate; and
$R^5$ is hydrogen or $C_{1-4}$ alkyl.

2. The pharmaceutical composition of claim 1, the insoluble polymer conjugate, further comprising a recurring unit of the formula (III):

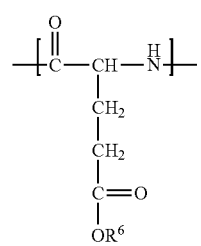

(III)

wherein $R^6$ is hydrogen, ammonium, or an alkali metal.

3. The pharmaceutical composition of claim 1, wherein the compound that comprises the agent further comprises a linker group.

4. The pharmaceutical composition of claim 1, wherein the agent is an optical imaging agent.

5. The pharmaceutical composition of claim 4, wherein the optical imaging agent is selected from the group consisting of an acridine dye, a coumarine dye, a rhodamine dye, a xanthene dye, cyanine dye, and a pyrene dye.

6. The pharmaceutical composition of claim 1, wherein the agent is an anticancer drug.

7. The pharmaceutical composition of claim 6, wherein the anticancer drug is selected from the group consisting of a taxane, camptothecin, and doxorubicin.

8. The pharmaceutical composition of claim 7, wherein the taxane is selected from the group consisting of paclitaxel and docetaxel.

9. The pharmaceutical composition of claim 8, wherein paclitaxel is conjugated to the recurring unit of formula (I) at the oxygen atom attached to the C7-carbon.

10. The pharmaceutical composition of claim 8, wherein paclitaxel is conjugated to the recurring unit of formula (I) at the oxygen atom attached to the C7-carbon.

11. The pharmaceutical composition of claim 1, wherein the agent is a magnetic resonance imaging agent.

12. The pharmaceutical composition of claim 11, wherein the magnetic resonance imaging comprises a Gd(III) compound.

13. The pharmaceutical composition of claim 12, wherein the Gd(III) compound comprises:

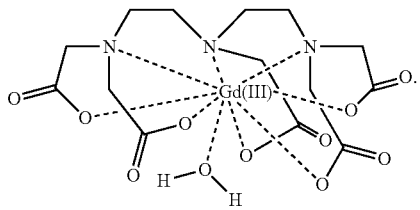

14. The pharmaceutical composition of claim 1, wherein the polydentate ligand comprises:

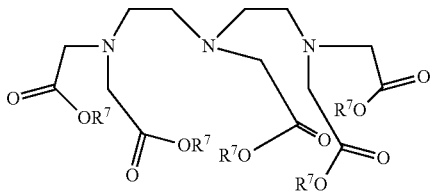

wherein each $R^7$ is independently hydrogen, ammonium, or an alkali metal.

15. The pharmaceutical composition of claim 1, wherein the polydentate ligand precursor with protected oxygen atoms comprises:

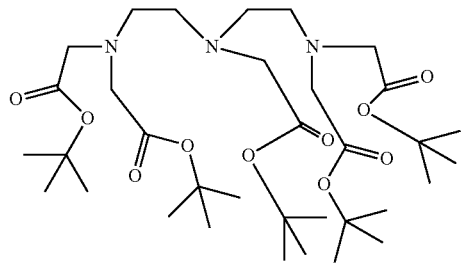

16. The pharmaceutical composition of claim 1, wherein at least one n is 1.

17. The pharmaceutical composition of claim 1, wherein at least one n is 2.

18. The pharmaceutical composition of claim 1, wherein the alkali metal is sodium.

19. The pharmaceutical composition of claim 1 further comprising at least one selected from a pharmaceutically acceptable excipient, a carrier, and a diluent.

20. A method of treating, ameliorating, or diagnosing a disease or condition comprising administering an effective amount of the pharmaceutical composition of claim 1 to a mammal in need thereof.

21. The pharmaceutical composition of claim 1, wherein:
n is 2;
each $A^1$ is oxygen;
each $A^2$ is oxygen;
$R^1$ is paclitaxel; and
$R^2$, $R^3$ and $R^4$ are each independently hydrogen or an alkali metal.

22. The pharmaceutical composition of claim 21, wherein the paclitaxel is conjugated to the recurring unit of formula (I) at the oxygen atom attached to the C2'-carbon.

23. The pharmaceutical composition of claim 21, wherein the paclitaxel is conjugated to the recurring unit of formula (I) at the oxygen atom attached to the C7-carbon.

24. A method of treating a cancer, comprising administering an effective amount of the pharmaceutical composition of claim 21 to a mammal in need thereof.

* * * * *